US009447029B2

(12) United States Patent
Pevarello

(10) Patent No.: US 9,447,029 B2
(45) Date of Patent: Sep. 20, 2016

(54) FLUORINATED ARYLALKYLAMINOCARBOXAMIDE DERIVATIVES

(75) Inventor: Paolo Pevarello, Pavia (IT)

(73) Assignee: NEWRON PHARMACEUTICALS S.P.A., Bresso (MI) (IT)

( * ) Notice: Subject to any disclaimer, the term of this patent is extended or adjusted under 35 U.S.C. 154(b) by 59 days.

(21) Appl. No.: 14/115,723

(22) PCT Filed: May 29, 2012

(86) PCT No.: PCT/EP2012/060006

§ 371 (c)(1), (2), (4) Date: Nov. 5, 2013

(87) PCT Pub. No.: WO2013/000651

PCT Pub. Date: Jan. 3, 2013

(65) Prior Publication Data

US 2014/0088074 A1 Mar. 27, 2014

(30) Foreign Application Priority Data

Jun. 27, 2011 (EP) .................................... 11171522

(51) Int. Cl.

| | |
|---|---|
| ***C07C 237/06*** | (2006.01) |
| ***C07D 277/24*** | (2006.01) |
| ***A61K 31/426*** | (2006.01) |
| ***C07D 209/08*** | (2006.01) |
| ***C07D 217/06*** | (2006.01) |
| ***C07D 265/36*** | (2006.01) |
| ***C07D 295/182*** | (2006.01) |
| ***C07D 295/185*** | (2006.01) |
| ***C07C 237/14*** | (2006.01) |
| ***C07C 237/20*** | (2006.01) |
| ***A61K 31/165*** | (2006.01) |
| ***A61K 31/397*** | (2006.01) |
| ***A61K 31/40*** | (2006.01) |
| ***A61K 31/4453*** | (2006.01) |
| ***A61K 31/47*** | (2006.01) |
| ***A61K 31/495*** | (2006.01) |
| ***A61K 31/5375*** | (2006.01) |
| ***A61K 31/538*** | (2006.01) |
| ***C07D 205/04*** | (2006.01) |
| ***C07D 207/06*** | (2006.01) |

(52) U.S. Cl.

CPC ........... *C07C 237/06* (2013.01); *A61K 31/165* (2013.01); *A61K 31/397* (2013.01); *A61K 31/40* (2013.01); *A61K 31/426* (2013.01); *A61K 31/4453* (2013.01); *A61K 31/47* (2013.01); *A61K 31/495* (2013.01); *A61K 31/538* (2013.01); *A61K 31/5375* (2013.01); *C07C 237/14* (2013.01); *C07C 237/20* (2013.01); *C07D 205/04* (2013.01); *C07D 207/06* (2013.01); *C07D 209/08* (2013.01); *C07D 217/06* (2013.01); *C07D 265/36* (2013.01); *C07D 277/24* (2013.01); *C07D 295/182* (2013.01); *C07D 295/185* (2013.01); *C07C 2101/14* (2013.01)

(58) Field of Classification Search

None

See application file for complete search history.

(56) References Cited

FOREIGN PATENT DOCUMENTS

| | | |
|---|---|---|
| WO | 2007071311 | 6/2007 |
| WO | 2008151702 | 12/2008 |

OTHER PUBLICATIONS

Danziger et al., Automated Site-directed Drug Design: A General Algorithm for Knowledge Acquisition about Hydrogen-Bonding Regions at Protein Surfaces, Mar. 22, 1989, The Royal Society, Proceedings of the Royal Society of London.Series B, Biological Sciences, vol. 236, No. 1283, p. 101-113.*

International Search Report issued in counterpart PCT Application No. PCT/EP2012/060006.

Written Opinion of International Searching Authority issued in counterpart PCT Application No. PCT/EP2012/060006.

* cited by examiner

*Primary Examiner* — San-Ming Hui
*Assistant Examiner* — Andrew Lee
(74) *Attorney, Agent, or Firm* — Silvia Salvadori, P.C.; Silvia Salvadori

(57) ABSTRACT

Fluorinated arylalkylaminocarboxamide derivatives of formula (I) are described wherein W, J, n, $R^1$, $R^2$, $R^3$, $R^4$, $R^5$ and $R^6$ have the meanings as defined in the specification and pharmaceutically salts thereof, pharmaceutical compositions containing them as active ingredients and their use as sodium and/or calcium channel modulators useful in preventing, alleviating and curing a wide range of pathologies, including neurological, psychiatric, cardiovascular, inflammatory, ophthalmic, urological, and gastrointestinal diseases, where the above mechanisms have been described as playing a pathological role.

I

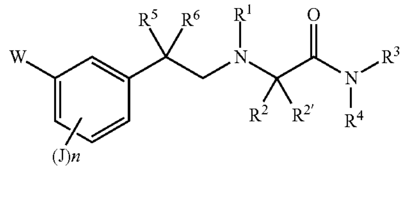

24 Claims, No Drawings

FLUORINATED ARYLALKYLAMINOCARBOXAMIDE DERIVATIVES

This application is a U.S. national stage of PCT/EP2012/060006 filed on May 29,2012, which claims priority to and the benefit of European Application No. 11171522.3 filed on Jun. 27,2011, the contents of which are incorporated herein by reference in their entirety.

The present invention relates to fluorinated arylalkylaminocarboxamide derivatives, pharmaceutically acceptable salts thereof, pharmaceutical compositions containing them and their use as sodium and/or calcium channel modulators.

The fluorinated arylalkylaminocarboxamide derivatives, object of the invention, are active as ion channel (in particular as sodium and/or calcium channel) modulators, and therefore useful in preventing, alleviating and curing a wide range of pathologies, including but not limited to neurological, psychiatric, cardiovascular, inflammatory, ophthalmic, urogenital and gastrointestinal diseases where the above mechanisms have been described as playing a pathological role.

BACKGROUND OF THE INVENTION

Chemical Background

WO 2007/071311 describes, substituted 2-phenylethylamino derivatives as voltage-gated calcium and/or sodium channels modulators of general formula I

I

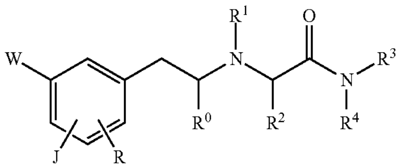

wherein:

(a)

J is a group A—[(CH$_2$)$_n$—O]$_r$— in para position with respect to the ethylamino chain wherein:

n is zero or 1;

r is 1; and

A is trifluormethyl; cyclopentyl; or phenyl optionally substituted with a halo group;

W is $(C_1-C_4)$alkoxy;

R is hydrogen;

$R^0$ is hydrogen; or $(C_1-C_2)$alkyl;

$R^1$ is hydrogen; $(C_1-C_4)$alkyl optionally substituted with a hydroxy group; cyclopropylmethyl; 2-propyn-1-yl; benzyl optionally substituted with one or two $(C_1-C_2)$alkoxy groups on the benzene ring; thiazolyl; a 5-6 membered saturated heterocyclyl containing a nitrogen atom, optionally substituted with a $(C_1-C_2)$alkyl group; or heterocyclylmethyl wherein the heterocyclyl group is a 5-6 membered heterocylyl containing 1 to 3 hetero atoms selected from nitrogen, oxygen and sulfur, optionally substituted with one or two groups selected from $(C_1-C_2)$alkyl, hydroxymethyl and $(C_1-C_2)$alkoxy;

$R^2$ is hydrogen; $(C_1-C_4)$alkyl; or phenyl;

$R^3$ is hydrogen; or $(C_1-C_4)$alkyl; and $R^4$ is hydrogen; $(C_1-C_4)$alkyl optionally substituted with a group selected from amino, $(C_1-C_4)$alkylamino, di-$(C_1-C_4)$alkylamino, imidazolyl and pyrrolidinyl wherein the imidazolyl and the pyrrolidinyl group is optionally substituted with a $(C_1-C_2)$alkyl group; or benzyl; or $R^3$ and $R^4$, taken together with the adjacent nitrogen atom, form a pyrrolidinyl, morpholinyl or piperazinyl ring optionally substituted with a $(C_1-C_2)$alkyl group;

or (b)

J is a group A—[(CH$_2$)$_n$—O]$_r$— in para position with respect to the ethylamino chain wherein:

n is 1;

r is 1; and

A is phenyl; or phenyl substituted with a halo group;

W is hydrogen;

R is hydrogen;

$R^0$ is $(C_1-C_2)$alkyl;

$R^1$ is hydrogen;

$R^2$ is $(C_1-C_2)$alkyl;

$R^3$ is hydrogen; or $(C_1-C_4)$ alkyl; and $R^4$ is hydrogen; or $(C_1-C_4)$alkyl;

or (c)

J is hydrogen;

W is a group A—[(CH$_2$)$_n$—O]$_r$— wherein:

n is zero, 1 or 2;

r is zero or 1; and

A is $(C_1-C_4)$alkyl, trifluoromethyl; cyclopropyl; cyclopentyl; phenyl optionally substituted with a group selected from halo, methyl, methoxy, trifluoromethyl, acetylamino, and dimethylaminomethyl; thienyl optionally substituted with a chloro group; furanyl; isoxazolyl optionally substituted with one or two methyl groups; piperidinyl; morpholinyl; pyridinyl or pyrimidinyl, the pyridinyl and pyrimidinyl ring being optionally substituted with one or two methoxy groups;

R is hydrogen; or fluoro;

$R^0$ is hydrogen; or $(C_1-C_2)$alkyl;

$R^1$ is isopropyl; cyclopropylmethyl; furanylmethyl; tetrahydrofuranyl; or tetrahydrofuranylmethyl;

$R^2$ is hydrogen; or $(C_1-C_4)$alkyl;

$R^3$ is hydrogen; or $(C_1-C_4)$alkyl; and $R^4$ is hydrogen; $(C_1-C_4)$alkyl optionally substituted with a group selected from $(C_1-C_2)$alkoxy, amino, $(C_1-C_4)$alkylamino and di-$(C_1-C_4)$alkylamino; or heterocyclyl wherein the heterocyclyl is selected from isoxazolyl, pyrazolyl, imidazolyl, thiazolyl and 1,3,4 thiadiazolyl and may be optionally substituted with a $(C_1-C_2)$alkyl group; or $R^3$ and $R^4$ taken together with the adjacent nitrogen atom form a pyrrolidine ring;

with the proviso that when A is $(C_1-C_4)$alkyl, trifluoromethyl, cyclopropyl or cyclopentyl, then r is 1; and with the further proviso that when $R^1$ is isoproryl, then A is trifluoromethyl and n is 1;

used for the manufacture of a medicament active as calcium and/or sodium channel modulators against disorders caused by dysfunctions of voltage gated calcium and/or sodium channels.

WO 2008/151702 describes substituted 2-[2-(phenyl)-ethylamino]alkaneamide derivatives as voltage-gated calcium and/or sodium channels modulators of general formula (I)

(I)

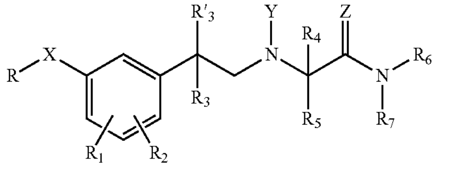

wherein:

X is —O—, —S— or —$SO_2$—;

Y is hydrogen, OH or $O(C_1-C_4)$alkyl;

Z is =O or =S;

R is $(C_3-C_{10})$alkyl; ω-trifluoro$(C_3-C_{10})$alkyl;

$R_1$ and $R_2$ are, independently, hydrogen, hydroxy, $(C_1-C_8)$ alkoxy, $(C_1-C_8)$ alkylthio, halo, trifluoromethyl or 2,2,2-trifluoroethyl; or one of $R_1$ and $R_2$ is in ortho position to R—X— and, taken together with the same R—X—, represents a

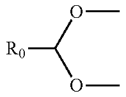

group where $R_0$ is $(C_2-C_9)$alkyl;

$R_3$ and $R'_3$ are, independently, hydrogen or $(C_1-C_4)$alkyl;

$R_4$ and $R_5$ are, independently, hydrogen, $(C_1-C_4)$alkyl; or $R_4$ is hydrogen and $R_5$ is a group selected from —$CH_2$—OH, —$CH_2$—O—$(C_1-C_6)$alkyl, —$CH(CH_3)$—OH, —$(CH_2)_2$—S—$CH_3$, benzyl and 4-hydroxybenzyl; or $R_4$ and $R_5$, taken together with the adjacent carbon atom, form a $(C_3-C_6)$cycloalkyl residue;

$R_6$ and $R_7$ are independently hydrogen or $(C_1-C_6)$alkyl; or taken together with the adjacent nitrogen atom form a 5-6 membered monocyclic saturated heterocycle, optionally containing one additional heteroatom chosen among —O—, —S— and —$NR_8$— where $R_8$ is hydrogen or $(C_1-C_6)$ alkyl;

with the proviso that when X is —S— or —$SO_2$—, then Y is not OH or $O(C_1-C_4)$ alkyl;

if the case, either as single optical isomer in the isolated form or mixture thereof in any proportion and its pharmaceutically acceptable salts.

The fluorinated compounds described in this application are not comprised by either WO 2007/071311 or WO 2008/151702.

Biological Background

Sodium channels play an important role in the neuronal network by transmitting electrical impulses rapidly throughout cells and cell networks, thereby coordinating higher processes ranging from locomotion to cognition. These channels are large transmembrane proteins, which are able to switch between different biophysical states to enable selective permeability for sodium ions. For this process to occur an action potential is needed to depolarize the membrane, and hence these channels are said voltage-gated.

Voltage-gated sodium channels were originally classified based on their sensitivity to tetrodotoxin, from low nanomolar (Tetrodotoxin sensitive, TTXs) to high micromolar (Tetrodotoxin resistant, TTXr). So far, 10 different sodium channel α subunits have been identified and classified as Nav1.1 to Nav1.9.

Nav1.1 to Nav1.4, Nav1.6 and Nav1.7 are TTXs, whereas Nav1.5, Nav1.8 and Nav1.9 are TTXr, with different degrees of sensitivity. Nav1.1 to Nav1.3 and Nav1.6, are primarily expressed in the CNS, whereas Nav1.4 and Nav1.5 are mainly expressed in muscle (skeletal and heart, respectively) and Nav1.8 and Nav1.9 are predominantly expressed in small dorsal root ganglions (DRG).

Nav1.3, a TTX-s sodium channel normally absent in adult neurons, is up-regulated following nerve injury as observed in the sensory neurons and spinal cord neurons of rodents following chronic nerve injuries (Waxman S. G., Kocsis J. D., Black J. A.: "Type III sodium channel mRNA is expressed in embryonic but not in adult spinal sensory neurons, and is reexpressed following axotomy". J. Neurophysiol. 72, 466-470 (1994). Haim B. C., Klein J. P., Saab C. Y. et al.: "Upregulation of sodium channel Nav1.3 and functional involvement in neuronal hyperexcitability associated with central neuropathic pain after spinal cord injury". J. Neurosci. 23, 8881-8892 (2003). Haim B. C., Saab C. Y., Klein J. P. et al.: "Altered sodium channel expression in second-order spinal sensory neurons contributes to pain after peripheral nerve injury". J. Neurosci. 24, 4832-4839 (2004)) and confirmed in human injured nerves after peripheral axotomy (Coward K., Aitken A., Powell A. et al.: "Plasticity of TTX-sensitive sodium channels PNI and brain III in injured human nerves". Neuroreport 12, 495-500 (2001)) and in human painful neuromas (Black J. A., Nikolajsen L., Kroner K. et al.: "Multiple sodium channel isoforms and mitogen-activated protein kinases are present in painful human neuromas". Ann. Neurol. 64(6), 644-653 (2008)). Nav1.3 channels exhibit several properties that can contribute to neuronal hyperexcitability. The rapid recovery from inactivation, and the ability to produce persistent current and ramp responses to small/slow depolarizations can support high-frequency firing. Interestingly, increased recovery rates have been described after nerve injury that would contribute to increase neuronal excitability in pain conditions (Cummins T. R., Waxman S. G.: "Downregulation of Tetrodotoxin resistant sodium currents and upregulation of a rapidly repriming tetrodotoxin-sensitive sodium current in small spinal sensory neurons after nerve injury". J. Neurosci. 17, 3503-3514 (1997). Cummins T. R., Aglieco F., Renganathan M. et al.: "Nav1.3 sodium channels: rapid repriming and slow closed-state inactivation display quantitative differences after expression in a mammalian cell line and in spinal sensory neurons". J. Neurosci. 21, 5952-5961 (2001). Lampert A., Haim B. C., Waxman S. G.: "Upregulation of persistent and ramp sodium current in dorsal horn neurons after spinal cord injury". Exp. Brain Res. 174, 660-666 (2006)).

Overall the specific expression and the biophysical properties of the Nav1.3 would implicate this channel in the generation of the TTX-sensitive ectopic discharges associated with chronic pain.

Nav1.7 channel is a TTX-s channel preferentially expressed in the primary DRG nociceptor neurons and in sympathetic ganglion neurons. It displays slow kinetics of transition to and from the inactivation state, that determine the possibility of generating currents in response to small subthreshold depolarizations and allow the channel to act as a threshold channel, thus amplifying generator potentials (Catterall W. A., Goldin A. L., Waxman S. G.: "International Union of Pharmacology. XLVII. Nomenclature and Structure-Function Relationships of Voltage-Gated Sodium Channels". Pharmacol. Rev. 57, 397-409 (2005)). Over the past few years, Nav1.7 has gained a prominent role in pain research because human genetic studies have directly linked single point mutations of the SCN9A gene encoding for Nav1.7 to specific pain syndromes. Gain of function mutations, that lower the threshold for channel activation, are associated to a dominant-inherited neuropathy, inherited erythromelalgia (IEM) whose hallmark symptom is severe burning pain in the feet and hands in response to mild warmth and exercise (Dib-Hajj S. D., Rush A. M., Cummins T. R. et al.: "Gain-of-function mutation in Nav1.7 in familial erythromelalgia induces bursting of sensory neurons". Brain 128(8), 1847-1854 (2005). Dib-Hajj S. D., Rush A. M., Cummins T. R., Waxman S. G.: "Mutations in the sodium channel Nav1.7 underlie inherited erythromelalgia". Drug Discovery Today: Disease Mechanisms 3(3), 343-350 (2006)).

One of the most compelling evidence that encouraged many companies to pursue research programs towards Nav1.7 specific inhibitors, has been the discovery that loss of function mutations of Nav1.7 gene determines a congenital insensitivity to pain (CIP) (Cox J. J., Reimann F., Nicholas A. K. et al.: "An SCN9A channelopathy causes congenital inability to experience pain". Nature 444, 894-8 (2006).

The TTX-r channel Nav1.8 is exclusively expressed in the peripheral sensory neurons. Slow inactivation kinetic, rapid repriming, depolarized threshold of activation and inactivation, make it ideal for maintaining action potential firing in depolarized fibers (Elliott A. A., Elliott J. R.: "Characterization of TTX-sensitive and TTX-resistant sodium currents in small cells from adult rat dorsal root ganglia". J. Physiol. 463, 39-56 (1993). Akopian A. N., Souslova V., England S. et al.: "The tetrodotoxin-resistant sodium channel SNS has a specialized function in pain pathways". Nat. Neurosci. 2, 541-548 (1999). Renganathan M., Cummins T. R., Waxman S. G.: "Contribution of Nav1.8 sodium channels to action potential electrogenesis in DRG neurons". J. Neurophysiol. 86, 629-640 (2001)). However, the specific translocation and redistribution of Nav1.8 protein at the peripheral site of injury observed in immunohistochemical studies in animals and recently in humans (Novakovic S. D., Tzoumaka E., McGivern J. G. et al.: "Distribution of the tetrodotoxin-resistant sodium channel PN3 in rat sensory neurons in normal and neuropathic conditions". J. Neurosci. 15, 18(6) 2174-2187 (1998). Black J. A., Nikolajsen L., Kroner K. et al.: "Multiple sodium channel isoforms and mitogen-activated protein kinases are present in painful human neuromas". Ann. Neurol. 64(6), 644-653 (2008)), or the redistribution and alterations of its activity in the remaining uninjured neurons (Gold M., Weinreich D., Kim C. S. et al.: "Redistribution of Nav 1.8 in uninjured axons enables neuropathic pain". J. Neurosci. 23, 158-166 (2003)), suggests a dynamic involvement of this channel in the generation and maintenance of nociceptive impulses.

Another TTX-r channel, Nav1.9, is exclusively expressed in small-diameter DRG neurons. It is still one of the least understood members of the voltage gated sodium channels (VGSC) family, due to the difficulty to express the recombinant form in heterologous expression systems. Characterization of the biophysical properties of this channel was done in sensory neurons from Nav 1.8-null mice (Cummins T. R., Dib-Hajj S. D., Black J. A. et al.: "A novel persistent tetrodotoxin-resistant sodium current in SNS-null and wild-type small primary sensory neurons". J. Neurosci. 19 (24): RC43 (1999)). These neurons were shown to express a persistent (non-inactivating) TTX-r current, with substantial overlap between activation and steady-state inactivation centered close to resting potential (Roza C., Laird J. M. A., Souslova V. et al.: "The tetrodotoxin-resistant Na+ channel Nav1.8 is essential for the expression of spontaneous activity in damaged sensory axons of mice". J. Physiol. 550, 921-926 (2003)). As a result of these properties, Nav1.9 channels behave as strong regulators of excitability in cells in which they are present, playing a key role in setting the resting membrane potential as well as contributing to subthreshold electrogenesis in small DRG neurons.

It has become clear that a number of drugs having a previously unknown mechanism of action actually act by modulating sodium channel conductance, including local anesthetics (LA), class I antiarrhythmics and anticonvulsants. Neuronal sodium channel blockers have found application with their use in the treatment of epilepsy (phenyloin and carbamazepine), bipolar disorder (lamotrigine), preventing neurodegeneration, and in reducing neuropathic pain. Various anti-epileptic drugs that even through other mechanisms of action, stabilize neuronal excitability are approved for different forms of neuropathic pain (gabapentin, pregabalin and carbamazepine).

In addition, an increase in sodium channel expression and/or activity has also been observed in several models of inflammatory pain, suggesting a role of sodium channels in inflammatory pain.

Calcium channels are membrane-spanning, multi-subunit proteins that allow controlled entry of calcium ions into cells from the extracellular fluid. Commonly, calcium channels are voltage dependent and are referred to as voltage-gated calcium channels (VGCC). VGCCs are found throughout the mammalian nervous system, where they regulate the intracellular calcium ion levels that are important for cell viability and function. Intracellular calcium ion concentrations are implicated in a number of vital processes in animals, such as neurotransmitter release, muscle contraction, pacemaker activity and secretion of hormones. All "excitable" cells in animals, such as neurons of the central nervous system (CNS), peripheral nerve cells, and muscle cells, including those of skeletal muscles, cardiac muscles and venous and arterial smooth muscles, have voltage dependent calcium channels.

Calcium channels are a large family with many genetically, physiologically, and pharmacologically distinct subtypes. Based on the biophysical properties of calcium currents recorded from individual neurons, two super-families have been described: High Voltage Activated (HVA) and Low Voltage Activated (LVA) calcium channels. Calcium currents referred as L-type, P-type, Q-type, N-type, R-type are HVA and as T-type are LVA. In particular, the term "L-type" was originally applied to channels with a large single channel conductance and long open time, and "T-type" was applied to channels with a tiny single channel conductance and a transient open time. Further exploration of functional calcium channel diversity identified the "N-type" channel expressed in neurons and the "P-type" channel, which is the dominant type expressed in cerebellar Purkinje neurons and is pharmacologically resistant to known blockers of L-type and N-type calcium channels. From the molecular identity, ten distinct calcium channel subtypes have been identified, cloned and expressed and grouped in three families: Cav1 family (Cav 1.1, 1.2, 1.3, 1.4) is functionally related to the L-type Ca current; Cav2 family (Cav 2.1, 2.2, 2.3) is functionally related to the P/Q, N, R-type currents and Cav3 (Cav 3.1, 3.2, 3.3) family is functionally related to the T-type current.

It is believed that calcium channels are relevant in certain disease states. A number of compounds useful in treating various cardiovascular diseases in mammals, including humans, are thought to exert their beneficial effects by modulating functions of voltage dependant calcium channels present in cardiac and/or vascular smooth muscle. Compounds with activity against calcium channels have also been implicated for the treatment of pain. In particular N-type calcium channels (Cav2.2), responsible for the regulation of neurotransmitter release, are thought to play a significant role in nociceptive transmission, both due to their tissue distribution as well as from the results of several pharmacological studies. N-type calcium channels were found up-regulated in the ipsilateral dorsal horn in neuropathic pain models of injury (Cizkova D., Marsala J., Lukacova N., Marsala M., Jergova S., Orendacova J., Yaksh T. L. Exp. Brain Res. 147: 456-463 (2002)). Specific N-type calcium channel blockers were shown to be effective in reducing pain responses in neuropathic pain models (Mattews E. A., Dickenson A. H. Pain 92: 235-246 (2001)), in the phase II of the formalin test (Diaz A., Dickenson A. H. Pain 69: 93-100 (1997)) and the hyperalgesia initiated by knee joint inflammation (Nebe J., Vanegas H., Schaible H. G. Exp. Brain Res. 120: 61-69 (1998)). Mutant mice, lacking the N-type calcium channels, were found to have a decreased response to persistent pain as seen by a decrease in pain response during phase II of the formalin test (Kim C., Jun K., Lee T., Kim S. S., Mcenery M. W., Chin H., Kim H. L, Park J. M., Kim D. K., Jung S. J., Kim J., Shin H. S. Mol. Cell. Neurosci. 18: 235-245 (2001); Hatakeyama S., Wakamori M., Ino M., Miyamoto N., Takahashi E., Yoshinaga T., Sawada K., Imoto K., Tanaka I., Yoshizawa T., Nishizawa Y., Mori Y., Nidome T., Shoji S, Neuroreport 12: 2423-2427 (2001)) as well as to neuropathic pain, assessed by a decrease in mechanical allodynia and thermal hyperalgesia in the spinal nerve ligation model (Yamamoto T., Takahara A.: "Recent updates of N-type calcium channel blockers with therapeutic potential for neuropathic pain and stroke". Curr. Top. Med. Chem. 9, 377-395 (2009)). Interestingly, mice also showed lower levels of anxiety when compared to wild type (Saegusa H., Kurihara T., Zong S., Kazuno A., Matsuda Y. Nonaka T., Han W., Toriyama H., Tanabe T., EMBO J. 20: 2349-2356 (2001)). The involvement of N-type calcium channels in pain has been further validated in the clinic by ziconotide, a peptide derived from the venom of the marine snail, *Conus Magnus*. (Williams J. A., Day M., Heavner J. E.: "Ziconotide: an update and review". Expert Opin. Pharmacother. 9(9), 1575-1583 (2008)). A limitation in the therapeutic use of this peptide is that it has to be administered intrathecally in humans (Bowersox S. S, and Luther R. Toxicon, 36: 1651-1658 (1998); Vitale V., Battelli D., Gasperoni E., Monachese N.: "Intrathecal therapy with ziconotide: clinical experience and consideration on its use". Minerva Anestesiol. 74, 727-733 (2008)).

A comprehensive review on the role and usefulness of ion channel modulators in neuropathic pain treatment has recently been published. (E. Colombo et al.: "Ion channel modulators for the treatment of neuropathic pain". Future Medicinal Chemistry, 2(5): 803-842 (2010)).

All together these findings indicate that compounds able to block sodium and/or calcium channels have an important therapeutic potential in preventing, alleviating and curing a wide range of pathologies, including neurological, psychiatric, cardiovascular, urogenital gastrointestinal and inflammatory diseases, where the above mechanisms have been described as playing a pathological role.

There are many papers and patents which describe sodium channel and/or calcium channel modulators or antagonists for the treatment or modulation of a plethora of disorders, such as their use as local anaesthetics, antiarrhythmics, antiemetics, antimanic anti-depressants, agents for the treatment of unipolar depression, anxiety, cardiovascular diseases, urinary incontinence, diarrhea, inflammation, epilepsy, neurodegenerative conditions, nerve cell death, neuropathic pain, migraine, acute hyperalgesia and inflammation, renal disease, allergy, asthma, bronchospasm, dysmenorrhea, esophageal spasm, glaucoma, urinary tract disorders, gastrointestinal motility disorders, premature labour, obesity, immune and endocrinological system disorders, including multiple sclerosis.

A non-exhaustive list of patents/patent applications describing sodium and/or calcium channel blockers and uses thereof includes the references shown below.

U.S. Pat. No. 5,051,403 relates to a method of reducing neuronal damage associated with an ischemic condition, such as stroke, by administration of binding/inhibitory omega-conotoxin peptide wherein the peptide is characterized by specific inhibition of voltage-gated calcium channel currents selectively in neuronal tissues.

U.S. Pat. No. 5,587,454 relates to compositions and methods of producing analgesia particularly in the treatment of pain and neuropathic pain.

U.S. Pat. No. 5,863,952 relates to calcium channel antagonists for the treatment of ischaemic stroke.

U.S. Pat. No. 6,011,035 relates to calcium channel blockers, useful in the treatment of conditions such as stroke and pain.

U.S. Pat. No. 6,117,841 relates to calcium channel blockers and their use in the treatment of stroke, cerebral ischemia, pain, head trauma or epilepsy.

U.S. Pat. No. 6,362,174 relates to N-type calcium channel blockers in the treatment of stroke, cerebral ischemia, pain, epilepsy, and head trauma.

U.S. Pat. No. 6,380,198 concerns the use of the calcium channel blocker flunarizine for the topical treatment of glaucoma.

U.S. Pat. No. 6,420,383 and U.S. Pat. No. 6,472,530 relate to novel calcium channel blockers, useful for treating and preventing a number of disorders such as hypersensitivity, allergy, asthma, bronchospasm, dysmenorrhea, esophageal spasm, glaucoma, premature labor, urinary tract disorders, gastrointestinal motility disorders and cardiovascular disorders.

U.S. Pat. No. 6,458,781 relates to compounds that act to block calcium channels and their use to treat stroke, cerebral ischemia, pain, head trauma or epilepsy.

U.S. Pat. No. 6,521,647 relates to the use of calcium channel blockers in the treatment of renal disease in animals, especially chronic renal failure.

WO 97/10210 relates to tricyclic heterocyclic derivatives, and their use in therapy, in particular as calcium channel antagonists, e.g. for the treatment of ischaemia, in particular ischaemic stroke.

WO 03/018561 relates to quinoline compounds as N-type calcium channel antagonists and methods of using such compounds for the treatment or prevention of pain or nociception.

WO 03/057219 relates to sodium channel blockers useful as agents for treating or modulating a central nervous system disorder, such as neuropathic pain, inflammatory pain, inflammation-related pain or epilepsy.

WO 99/14199 discloses substituted 1,2,3,4,5,6-hexahydro-2,6-methano-3-benzazocines-10-oles as potent sodium channel blockers useful for the treatment of several diseases, such as stroke, neurodegenerative disorders, Alzheimer's Disease, Parkinson's Disease and cardiovascular disorders.

WO 01/74779 discloses new aminopyridine sodium channel blockers and their use as anticonvulsants, local anesthetics, as antiarrythmics, for the treatment or prevention of neurodegenerative conditions, such as amyotrophic lateral sclerosis (ALS), for the treatment or prevention of both, acute or chronic pain, and for the treatment or prevention of diabetic neuropathy.

WO 04/087125 discloses amino acid derivatives as inhibitors of mammalian sodium channels, useful in the treatment of chronic and acute pain, tinnitus, bowel disorders, bladder dysfunction and demyelinating diseases.

WO 06/028904 relates to quinazolines useful as modulators of ion channels, and their preparation, pharmaceutical compositions, and use as inhibitors of voltage-gated sodium channels, which is useful in treatment of various diseases.

WO 06/024160 discloses the preparation of piperazine-1-carboxamide derivatives as calcium channel blockers.

WO 06/110917 describes spiro-oxindole compounds and their preparation, pharmaceutical compositions and use as sodium channel blockers.

WO 06/027052 describes the use of selected (R)-2-[(halobenzyloxy)benzylamino]-propanamides and the pharmaceutically acceptable salts thereof for the manufacture of medicaments that are selectively active as sodium and/or calcium channel modulators and therefore useful in preventing, alleviating and curing a wide range of pathologies, including pain, migraine, peripheral diseases, cardiovascular diseases, inflammatory processes affecting all body systems, disorders affecting skin and related tissues, disorders of the respiratory system, disorders of the immune and endocrinological systems, gastrointestinal, urogenital, metabolic and seizure disorders, where the above mechanisms have been described as playing a pathological role.

WO 07/145,922 discloses the preparation of benzazepinone amino acids as sodium channel blockers.

WO 07/021,941 relates to the preparation of N-thiazolyl benzenesulfonamides as inhibitors of voltage-gated sodium channels.

WO 08/141,446 discloses amino acid derivatives as calcium channel blockers.

WO 09/005,460 describes the preparation and applications of Nav1.7 sodium channel inhibitors for treatment of pain disorders.

WO 09/039,328 discloses pyridyl-sulfonamides as modulators of sodium channels, their preparation, pharmaceutical compositions, and use in treating various diseases.

WO 09/045,381 relates to N-substituted oxindoline derivatives as calcium channel blockers.

WO 10/007,073 discloses the preparation of piperazine derivatives as Cav2.2 calcium channel modulators.

WO 10/014,257 describes the preparation of tetrahydropyridine and dihydropyrrole compounds as calcium channel blockers for treatment of pain and other disorders.

The cytochrome P450 superfamily (abbreviated as CYP) is a large and diverse group of enzymes and the function of most CYP enzymes is to catalyze the oxidation of organic substances. The substrates of CYP enzymes include xenobiotic substances such as drugs and other toxic chemicals. CYPs are the major enzymes involved in drug metabolism and bioactivation, accounting for at least 75% of the total metabolism. Human CYPs are primarily membrane-associated proteins, located either in the inner membrane of mitochondria or in the endoplasmic reticulum of cells (Smith G., Stubbins M. J. Xenobiotica 28 (12): 1129-65 (1998)). Many drugs may increase or decrease the activity of various CYP isozymes either by inducing the biosynthesis of an isozyme (enzyme induction) or by directly inhibiting the activity of the CYP (enzyme inhibition). This is a major source of adverse drug interactions, since changes in CYP enzyme activity may affect the metabolism and clearance of various drugs. For example, if one drug inhibits the CYP-mediated metabolism of another drug, the second drug may accumulate within the body to toxic levels. Hence, avoiding drug interactions may necessitate dosage adjustments or the choice of drugs that do not interact with the CYP system.

Cytochrome P450 2D6 (CYP2D6), a member of the cytochrome P450 mixed-function oxidase system, is one of the most important enzymes involved in the metabolism of xenobiotics in the body (Wolf C. R., Smith G. IARC Sci. Publ.; 148: 209-29 (1999)). Whilst CYP2D6 is involved in the oxidation of a wide range of substrates of all the CYPs, there is considerable variability in its expression in the liver. The gene is located near two cytochrome P450 pseudogenes on chromosome 22q13.1. Alternatively spliced transcript variants encoding different isoforms have been found for this gene.

CYP2D6 shows the largest phenotypical variability among the CYPs, largely due to genetic polymorphism. The genotype accounts for normal, reduced, and non-existent CYP2D6 function in subjects.

The CYP2D6 function in any particular subject may be described as one of the following:

- poor metabolizers—these subjects have little or no CYP2D6 function
- intermediate metabolizers—these subjects metabolize drugs at a rate somewhere between the poor and extensive metabolizers
- extensive metabolizers—these subjects have normal CYP2D6 function
- ultrarapid metabolizers—these subjects have multiple copies of the CYP2D6 gene expressed, and therefore greater-than-normal CYP2D6 function.

Therefore, patients undergoing any therapeutical treatment may be classified according to the above subject definitions.

Many antipsychotic drugs used for schizophrenia treatment are CYP2D6 substrates: examples of these drugs include haloperidol, risperidone, perphenazine, thioridazine, aripiprazole and sertindole. If a drug is able to potently inhibit CYP2D6 the subject taking said drug may become a poor metabolizer, i.e. may experience an increase in plasma levels of a CYP2D6 metabolized drug taken concomitantly. Quinidine, paroxetine, bupropion and fluoxetine are powerful CYP2D6 inhibitors and the use of potent inhibitors can render a patient that is a CYP2D6 extensive metabolizer into a phenotypic poor metabolizer (De Leon J., Armstrong S. C., Cozza K. L. Psychosomatics; 47(1): 75-85 (2006)). A CYP2D6 poor metabolizer phenotype may have a major role in personalizing risperidone doses (De Leon J., Susce M. T., Pan R. M., Wedlun P. J., Orrego M. L., Diaz F. J. Pharmacopsychiatry; 40(3), 93-102 (2007)). As a further example, sertindole undergoes extensive hepatic metabolism by CYP2D6 and 3A4 to two principal metabolites. CYP2D6 poor metabolizers may have sertindole clearance reduced by 50-67%. The concomitant administration of sertindole and CYP2D6 inhibitors should be used with extreme caution (Murdoch D., Keating G. M. CNS Drugs; 20(3): 233-255 (2006)).

It is therefore highly desirable, in view of avoiding undue drug-drug interactions, to have compounds which are unable to inhibit the major human CYPs, in particular CYP2D6, for example in a psychosis and schizophrenia setting, but also in any pathology treated with a drug that is also a CYP2D6 substrate (Foster A. Mobley E., Wang Z. Pain Practice; 7(4): 352-356 (2007)).

DESCRIPTION OF THE INVENTION

The object of this invention is a new class of fluorinated arylalkylamino carboxamide derivatives which are highly potent as sodium and/or calcium channel modulators and therefore useful in preventing, alleviating and curing a wide range of pathologies, including, but not limited to psychiatric, neurological, cardiovascular, inflammatory, ophthalmic, urogenital, gastrointestinal diseases where the above mechanisms have been described as playing a pathological role. Said compounds are also characterized in that they are substantially free from any CYP2D6 inhibitory effect or exhibit a significantly reduced CYP2D6 inhibitory effect.

In this description and claims, the expression "sodium and/or calcium channel modulator(s)" means compounds able to block sodium and/or calcium currents in a voltage and/or use-dependent manner.

In this description and claims the expression "substantially free from any CYP2D6 inhibitory effect" means that the compound exhibits a $IC_{50}[\mu M]$ value in the in vitro cytochrome inhibition test according to Example 10 which is higher than 40 while the expression "reduced CYP2D6 inhibitory effect" means that the compounds exhibits a $IC_{50}[\mu M]$ value which is higher than 20.

In particular, the object of the present invention is a compound of general formula I

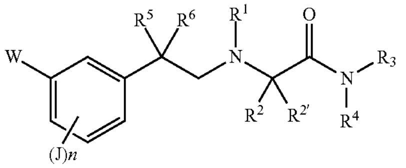

I wherein:

W is a group A—[$(CH_2)_m$—O]— wherein: m is zero, 1, 2, or 3; A is ($C_1$-$C_4$)alkyl optionally substituted with one to three fluorine atoms; ($C_3$-$C_6$)cycloalkyl; phenyl optionally substituted with a group selected from halo, methyl, methoxy, trifluoromethyl, acetylamino, and dimethylaminomethyl; thienyl optionally substituted with a chloro group; furanyl; isoxazolyl, thiazolyl; piperidinyl; morpholinyl; pyridinyl or pyrimidinyl, the pyridinyl and pyrimidinyl ring being optionally substituted with one or two methoxy groups;

J independently is hydrogen, ($C_1$-$C_4$)alkyl; ($C_1$-$C_4$)alkoxy; or an halo group;

n is 1 or 2;

$R^1$ is hydrogen; ($C_1$-$C_4$)alkyl optionally substituted with a hydroxy group or a ($C_1$-$C_4$)alkoxy group; or ($C_3$-$C_8$) cycloalkyl;

$R^2$ and $R^{2'}$ are independently hydrogen; ($C_1$-$C_4$)alkyl optionally substituted with a ($C_1$-$C_4$)alkoxy group; phenyl optionally substituted with a ($C_1$-$C_4$)alkyl, a ($C_1$-$C_4$) alkoxy or an halo group; benzyl optionally substituted with a ($C_1$-$C_4$)alkyl, a ($C_1$-$C_4$)alkoxy or an halo group on the benzene ring; or $R^2$ and $R^{2'}$ taken together with the adjacent carbon atom form a ($C_3$-$C_6$)cycloalkylidene group.

$R^3$ is hydrogen; or ($C_1$-$C_4$)alkyl;

$R^4$ is hydrogen; ($C_1$-$C_4$)alkyl; phenyl; cyclohexyl; or benzyl; or $R^3$ and $R^4$, taken together with the adjacent nitrogen atom, form an azetidinyl, pyrrolidinyl, morpholinyl, piperidinyl or piperazinyl ring, the piperidinyl ring being optionally substituted with one or two ($C_1$-$C_2$)alkyl group(s), and the piperazinyl ring being optionally substituted on the other N-atom with a ($C_1$-$C_4$)alkyl, benzyl, or phenylsulfonyl group; or a pyrrolidinyl, piperidinyl, morpholinyl or piperazinyl ring fused with a benzene ring;

$R^5$ is hydrogen or fluoro; and $R^6$ is fluoro;

if the case, either as single optical isomer in the isolated form or as a mixture thereof in any proportion and its pharmaceutically acceptable salt.

The term "($C_1$-$C_4$)alkyl" or the "($C_1$-$C_4$) alkyl" moiety in the other substitutents (e.g. in the terms alkoxy) as used in this description and claims, when no otherwise specified, identifies a straight or branched alkyl radical or moiety; examples of said radicals or moieties include, respectively: methyl, ethyl, propyl, isopropyl, butyl, isobutyl and tert-butyl or methoxy, ethoxy, propoxy, isopropoxy, butoxy isobutoxy and tert-butoxy.

The term "($C_1$-$C_4$)alkyl" when substituted with "one to three fluorine atoms" identifies a straight or branched alkyl radical of 1 to 4 carbon atoms wherein one to three hydrogen atoms attached to the same or different carbon atoms are independently substituted by fluorine. Preferred representative examples of this term are trifluoromethyl, 2,2,2-trifluoroethyl, 3,3,3-trifluoropropyl and 4,4,4-trifluorobutyl.

The terms "($C_3$-$C_6$)cycloalkyl" and "($C_3$-$C_6$)cycloalkylidene" as used in this description and claims, when not otherwise specified, identifies a cycle-forming alkyl or alkylidene radical or moiety; examples of said radicals or moieties include, respectively cyclopropyl, cyclobutyl, cyclopentyl, and cyclohexyl, or cyclopropylidene, cyclobutylidene, cyclopentylidene and cyclohexylidene.

The term "halo", when not otherwise specified herein, means an halogen atom radical such as fluoro, chloro, bromo and iodo.

Where the compounds of this invention contain at least one asymmetric carbon atom they can exist as single enantiomers or diastereoisomers or a mixture thereof, the invention includes within its scope all the possible single optical isomers in the isolated form of said compounds and the mixtures thereof in any proportion, e.g., the racemic mixtures.

Examples of pharmaceutically acceptable salts of the compounds of formula I are salts with organic and inorganic acids such as hydrochloric, hydrobromic, hydroiodic, nitric, sulfuric, phosphoric, acetic, propionic, tartaric, fumaric, citric, benzoic, succinic, cinnamic, mandelic, salicylic, glycolic, lactic, oxalic, malic, maleic, malonic, fumaric, tartaric, p-toluenesulfonic, methanesulfonic, glutaric acid and the like.

The compounds of formula I are active as calcium and/or sodium channel modulators and therefore useful in preventing alleviating and curing a wide range of pathologies, including but not limited to psychiatric, neurological, cardiovascular, inflammatory, ophthalmic, urogenital and gastrointestinal diseases where the above mechanisms have been described as playing a pathological role, said compounds being characterized in that they are substantially free from any CYP2D6 inhibitory effect or exhibit a significantly reduced CYP2D6 inhibitory effect.

A preferred group of compounds of formula I of this invention comprises a compound wherein:

W is a group A—[$(CH_2)_m$—O]— wherein: m is zero, 1, 2 or 3; A is ($C_1$-$C_4$)alkyl optionally substituted with one to three fluorine atoms; ($C_3$-$C_6$)cycloalkyl; phenyl optionally substituted with a halo group; or thiazolyl J independently is hydrogen; $C_1$-$C_4$ alkyl; chloro; or fluoro;

n is 1 or 2;

$R^1$ is hydrogen; ($C_1$-$C_4$)alkyl optionally substituted with a hydroxy group or a ($C_1$-$C_4$)alkoxy group; or ($C_3$-$C_6$) cycloalkyl;

$R^2$ is hydrogen; or ($C_1$-$C_4$)alkyl;

$R^{2'}$ is hydrogen; ($C_1$-$C_4$)alkyl optionally substituted with a ($C_1$-$C_4$)alkoxy; or a phenyl group, the phenyl group being optionally substituted with a ($C_1$-$C_4$)alkoxy group;

$R^3$ is hydrogen; or ($C_1$-$C_4$)alkyl;

$R^4$ is hydrogen; ($C_1$-$C_4$)alkyl; phenyl; or cyclohexyl; or $R^3$ and $R^4$, taken together with the adjacent nitrogen atom, form an azetidinyl, pyrrolidinyl, morpholinyl, piperidinyl or piperazinyl, the piperydinyl ring being optionally substituted with one or two ($C_1$-$C_2$)alkyl group(s) and the piperazinyl ring being optionally substituted on the other N-atom with a ($C_1$-$C_4$)alkyl, benzyl, or phenylsulfonyl group; or a pyrrolidinyl, piperidinyl, morpholinyl or piperazinyl ring fused with a benzene ring;

$R^5$ is hydrogen or fluoro; and $R^6$ is fluoro;

if the case, either as single optical isomer in the isolated form or as a mixture thereof in any proportion and its pharmaceutically acceptable salt.

A more preferred group of compounds of formula I comprises a compound wherein;

W is a group A—[$(CH_2)_m$—O]— wherein: m is 1 or 2; A is ($C_1$-$C_4$)alkyl optionally substituted with one to three fluorine atoms; phenyl optionally substituted with a chloro or fluoro group; or thiazolyl;

J independently is hydrogen; methyl; or fluoro;

n is 1 or 2

$R^1$ is hydrogen; ($C_1$-$C_4$)alkyl optionally substituted with a hydroxy group or a ($C_1$-$C_4$)alkoxy group;

$R^2$ is hydrogen; or methyl;

$R^{2'}$ is hydrogen; ($C_1$-$C_4$)alkyl optionally substituted with a methoxy; or a phenyl group, the phenyl group being optionally substituted with a methoxy group;

$R^3$ is hydrogen; or ($C_1$-$C_4$)alkyl;

$R^4$ is hydrogen; ($C_1$-$C_4$)alkyl; phenyl; or cyclohexyl; or $R^3$ and $R^4$, taken together with the adjacent nitrogen atom, form an azetidinyl, pyrrolidinyl, morpholinyl, piperidinyl, or piperazinyl ring, the piperidinyl ring being optionally substituted with one or two methyl group(s) and the piperazinyl ring being optionally substituted on the other N-atom with a methyl, benzyl or phenylsulfonyl group; or a pirrolidinyl, piperidinyl, morpholinyl, or piperazinyl ring fused with a benzene ring;

$R^5$ is hydrogen or fluoro; and $R^6$ is fluoro;

if the case, either as single optical isomer in the isolated form or as a mixture thereof in any proportion and its pharmaceutically acceptable salt.

Most preferably, a compound of formula I according to this invention is selected from the group consisting of:

2-[2,2-Difluoro-2-(3-butoxyphenyl)-ethylamino]-N,N-dimethyl-acetamide; (Example 1-1)

2-[2,2-Difluoro-2-(3-pentyloxyphenyl)-ethylamino]-N,N-dimethyl-acetamide (Example 1-2)

2-[2,2-Difluoro-2-(3-butoxyphenyl)-ethylamino]-N,N-dipropyl-acetamide (Example 1-3)

2-[2,2-Difluoro-2-(3-butoxy-4-methylphenyl)-ethylamino]-N,N-dimethyl-acetamide; (Example 1-4)

2-[2,2-Difluoro-2-(3-butoxyphenyl)-ethylamino]-N,N-dibutyl-acetamide; (Example 1-5)

2-[2,2-Difluoro-2-(3-hexyloxyphenyl)-ethylamino]-N,N-dimethyl-acetamide; (Example 1-6)

2-{2,2-Difluoro-2-[3-(4,4,4-trifluorobutoxy)-phenyl]-ethylamino}-N,N-dimethyl-acetamide; (Example 1-7)

2-[2,2-Difluoro-2-(3-pentyloxyphenyl)-ethylamino]-N,N-dipropyl-acetamide; (Example 1-8)

2-{2,2-Difluoro-2-[3-(3-(3-fluorophenyl)-propoxy)-phenyl]-ethylamino}-N,N-dimethyl-acetamide; (Example 1-9)

2-{2,2-Difluoro-2-[3-(3-(3-chlorophenyl)-propoxy)-phenyl]-ethylamino}-N,N-dimethyl-acetamide; (Example 1-10)

2-[2,2-Difluoro-2-(3-butoxy-2-fluorophenyl)-ethylamino]-N,N-dimethyl-acetamide; (Example 1-11)

2-{2,2-Difluoro-2-[3-(3-phenylpropoxy)-phenyl]-ethylamino}-N,N-dimethyl-acetamide; (Example 1-12)

2-{2,2-Difluoro-2-[3-(3-thiazol-2-yl-propoxy)-phenyl]-ethylamino}-N,N-dimethyl-acetamide; (Example 1-13)

2-[2,2-Difluoro-2-(3-benzyloxyphenyl)-ethylamino]-N,N-dimethyl-acetamide; (Example 1-14)

2-[2,2-Difluoro-2-(3-butoxyphenyl)-ethylamino]-1-(pyrrolidin-1-yl)-ethanone; (Example 1-15)

2-[2,2-Difluoro-2-(3-butoxyphenyl)-ethylamino]-N-methyl-N-phenyl-acetamide; (Example 1-16)

2-{2,2-Difluoro-2-[3-(3-phenylpropoxy)-phenyl]-ethylamino}-1-(pyrrolidin-1-yl)-ethanone; (Example 1-17)

2-{2,2-Difluoro-2-[3-(4,4,4-trifluorobutoxy)-phenyl]-ethylamino}-1-(pyrrolidin-1-yl)-ethanone; (Example 1-18)

2-[2,2-Difluoro-2-(3-benzyloxyphenyl)-ethylamino]-1-(morpholin-4-yl)-ethanone; (Example 1-19)

2-{2,2-Difluoro-2-[3-(3-phenylpropoxy)-phenyl]-ethylamino}-1-(morpholin-4-yl)-ethanone; (Example 1-20)

2-{2,2-Difluoro-2-[3-(4,4,4-trifluorobutoxy)-phenyl]-ethylamino}-1-(morpholin-4-yl)-ethanone; (Example 1-21)

2-[2,2-Difluoro-2-(3-butoxyphenyl)-ethylamino]-1-(2H-benzo[b][1,4]oxazin-4(3H)-yl)-ethanone; (Example 1-22)

2-[2,2-Difluoro-2-(3-benzyloxyphenyl)-ethylamino]-1-(pyrrolidin-1-yl)-ethanone; (Example 1-23)

2-{2,2-Difluoro-2-[3-(3-phenylpropoxy)-phenyl]-ethylamino}-N-methyl-N-phenyl-acetamide; (Example 1-24)

2-{2,2-Difluoro-2-[3-(4,4,4-trifluorobutoxy)-phenyl]-ethylamino}-N-methyl-N-phenyl-acetamide; (Example 1-25)

2-[2,2-Difluoro-2-(3-butoxyphenyl)-ethylamino]-1-(4-methylpiperazin-1-yl)-ethanone; (Example 1-26)

2-{2,2-Difluoro-2-[3-(3-phenylpropoxy)-phenyl]-ethylamino}-1-(4-methylpiperazin-1-yl)-ethanone; (Example 1-27)

2-{2,2-Difluoro-2-[3-(4,4,4-trifluorobutoxy)-phenyl]-ethylamino}-1-(4-methylpiperazin-1-yl)-ethanone; (Example 1-28)

2-[2,2-Difluoro-2-(3-butoxyphenyl)-ethylamino]-1-(piperidin-1-yl)-ethanone; (Example 1-29)

2-{2,2-Difluoro-2-[3-(3-phenylpropoxy)-phenyl]-ethylamino}-1-(piperidin-1-yl)-ethanone; (Example 1-30)

2-{2,2-Difluoro-2-[3-(4,4,4-trifluorobutoxy)-phenyl]-ethylamino}-1-(piperidin-1-yl)-ethanone; (Example 1-31)

2-[2,2-Difluoro-2-(3-butoxyphenyl)-ethylamino]-N,N-diethyl-acetamide; (Example 1-32);

2-{2,2-Difluoro-2-[3-(2-fluorobenzyloxy)-phenyl]-ethylamino}-N,N-dimethyl-acetamide; (Example 1-33)

2-[2,2-Difluoro-2-(3-butoxyphenyl)-ethylamino]-1-(cis-3,5-dimethylpiperidin-1-yl)-ethanone; (Example 1-34)

2-[2,2-Difluoro-2-(3-butoxyphenyl)-ethylamino]-1-(3,4-dihydroisoquinolin-2(1H)-yl)-ethanone; (Example 1-35)

2-[2,2-Difluoro-2-(3-butoxyphenyl)-ethylamino]-N,N-diisopropyl-acetamide; (Example 1-36)

2-[2,2-Difluoro-2-(3-butoxyphenyl)-ethylamino]-N-cyclohexyl-N-methyl-acetamide; (Example 1-37)

2-[2,2-Difluoro-2-(3-benzyloxyphenyl)-ethylamino]-1-(piperidin-1-yl)-ethanone; (Example 1-38)

2-[2,2-Difluoro-2-(3-butoxyphenyl)-ethylamino]-1-[4-(phenylsulfonyl)-piperazin-1-yl]-ethanone; (Example 1-39)

2-[2,2-Difluoro-2-(3-butoxyphenyl)-ethylamino]-1-(indolin-1-yl)-ethanone; (Example 1-40)

2-[2,2-Difluoro-2-(3-butoxyphenyl)-ethylamino]-1-(4-benzylpiperazin-1-yl)-ethanone; (Example 1-41)

2-[2,2-Difluoro-2-(3-butoxyphenyl)-ethylamino]-1-(azetidin-1-yl)-ethanone; (Example 1-42)

2-[2,2-Difluoro-2-(3-butoxyphenyl)-ethylamino]-N,N-dimethyl-propanamide; (Example 2-1)

2-[2,2-Difluoro-2-(3-butoxyphenyl)-ethylamino]-3-methoxy-N,N-dimethyl-propanamide; (Example. 2-2)

2-[2,2-Difluoro-2-(3-butoxyphenyl)-ethylamino]-3-(4-methoxyphenyl)-N,N-dimethyl-propanamide; (Example 2-3)

2-[2,2-Difluoro-2-(3-butoxyphenyl)-ethylamino]-2-N,N-trimethyl-propanamide; (Example 2-4)

2-[2,2-Difluoro-2-(3-butoxyphenyl)-ethylamino]-4-N,N-trimethyl-pentanamide; (Example 2-5)

2-{[2,2-Difluoro-2-(3-butoxyphenyl)-ethyl]-methylamino}-N,N-dimethyl-acetamide; (Example. 3-1)

2-{[2,2-Difluoro-2-(3-butoxyphenyl)-ethyl]-(3-methoxypropyl)-amino}-N,N-dimethyl-acetamide; (Example 3-2)

2-{[2,2-Difluoro-2-(3-butoxyphenyl)-ethyl]-(2-methoxyethyl)-amino}-N,N-dimethyl-acetamide; (Example 3-3)

2-[2-Fluoro-2-(3-butoxyphenyl)-ethylamino]-N,N-dimethyl-acetamide; (Example 4-1)

2-{2-Fluoro-2-[3-(3-chlorobenzyloxy)-phenyl]-ethylamino}-N,N-dimethyl-acetamide; (Example 4-2)

2-{2-Fluoro-2-[3-(3-fluorobenzyloxy)-phenyl]-ethylamino}-N,N-dimethyl-acetamide; (Example 4-3)

if the case, either as single optical isomer in the isolated form or as a mixture thereof in any proportion and its pharmaceutically acceptable salt.

The compounds of formula I, object of the present invention, are prepared according to a synthetic process which comprises:

a) the reaction of a compound of formula II

II

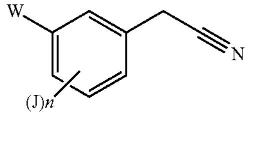

wherein

J, W, and n have the same meanings defined in formula I above, with a suitable fluorinating agent, such as N-fluorobenzenesulfonimide, to give a compound of formula III

III

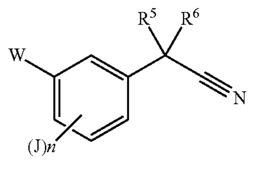

wherein

J, W, n, $R^5$ and $R^6$ have the same meanings as defined in formula I above b) reaction of a compound of formula III with a suitable reducing agent, such as lithium aluminium hydride, to give a compound of formula IV

IV

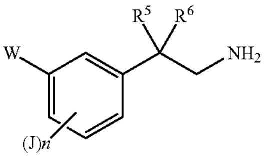

wherein

W, J, n, $R^5$ and $R^6$ have the same meanings as defined in formula I above;

c) protection of the amino group of a compound of formula IV with a suitable protecting agent, such as di-tert-butoxydicarbonate, to give a compound of formula V

V

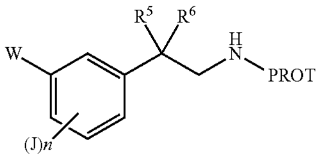

wherein

W, J, n, $R^5$ and $R^6$ have the same meanings as defined in formula I above and PROT is a suitable N-protecting group, for example a tert-butoxycarbonyl grup.

d) reacting a compound of formula V with a suitable haloalkylamide of formula VI

VI

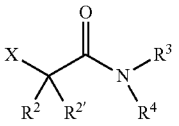

wherein X is a halogen atom and $R^2$, $R^{2'}$, $R^3$, and $R^4$ have the same meaning as defined in formula I above, whereby a compound of formula I is obtained wherein $R^1$ is hydrogen.

The compound of formula I wherein J, W, n, $R^2$, $R^{2'}$, $R^3$, $R^4$, $R^5$, and $R^6$ have the same meanings as above and $R^1$ has the same meanings as above, apart from hydrogen, can be prepared through the reaction of a compound of formula VII

VII

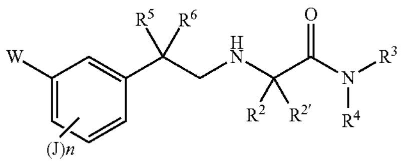

wherein

J, W, n, $R^2$, $R^{2'}$, $R^3$, $R^4$, $R^5$, and $R^6$, have the same meanings as in formula I above, with a compound $R^1$—Z, wherein $R^1$ has the meanings reported above apart from hydrogen and Z is a halogen atom or a good leaving group, e.g. methanesulfonyloxy, p-toluenesulfonyloxy or trifluoromethanesulfonyloxy in the presence of a base or with a carbonyl compound of the formula $R^7R^8CO$ in the presence of a reducing agent, wherein $R^7$ and $R^8$ both represent hydrogen or, taken together with the adjacent carbonyl group, represent a $(C_2-C_4)$aliphatic aldehyde or a $(C_3-C_4)$ aliphatic ketone, optionally substituted with a hydroxyl group or a $(C_1-C_4)$alkoxy group, or $R^7$ and $R^8$ taken together with the adjacent carbonyl group represent a $(C_3-C_8)$ alicyclic ketone.

A compound of the invention may be converted into another compound of the invention. For instance, a compound of formula I wherein W represents a benzyloxy radical may be transformed into the corresponding hydroxy-derivative by catalytic hydrogenation and then reacted with an appropriate reagent to replace the original benzyl moiety with a different group, e.g., a trifluoromethylbenzyl, phenylethyl, trifluoroethyl, cyclopentyl, and cyclopropylmethyl. If desired, a compound of the invention may be converted into a pharmaceutically acceptable salt and/or, if desired, a salt may be converted into a free compound and/or, if desired, a mixture of enantiomers or diastereoisomers of compounds of the invention may be separated into the corresponding single optical isomers.

The compounds of formula II and VI are commercially available or are prepared from commercially available compounds according to well-known methods.

When a compound of formula I is obtained wherein $R^1$ is hydrogen (i.e., a compound of formula VII) the introduction of a radical $R^1$ which is other than hydrogen defined above is carried out according to conventional methods for the preparation of secondary or tertiary amines such as alkylation or reductive amination techniques as described above.

According to a preferred embodiment of the invention said alkylation reaction is carried out in the presence of a base and, more preferably, said base is selected from $K_2CO_3$, triethylamine and diisopropylethylamine.

According to another preferred embodiment of the invention said reductive amination with a compound $R^7R^8CO$, wherein $R^7$ and $R^8$ have the same meanings as defined above is carried out in the presence of a reducing agent selected from $NaBH_4$, $NaBH_3CN$ and (polystyrylmethyl)-trimethylammonium cyanoborohydride.

In the preparation of the compounds of formula I and the starting materials and/or intermediates described herein it may be useful to protect certain groups which are sensitive to the reaction conditions.

The evaluation of the usefullness of the optional protection, as well as the selection of the suitable protecting agent, according to the reaction carried out in the preparation of the compounds of the invention and the functional group to be protected, are within the common knowledge of the skilled person.

The removal of the optional protective groups is carried out according to conventional techniques.

For a general reference to the use of protective groups in organic chemistry, see Theodora W. Greene and Peter G. M. Wuts "Protective groups in organic synthesis", John Wiley & Sons, Inc., II Ed., 1991.

The preparation of the salts of the compounds of formula I is carried out according to known methods.

For the preparation of a single enantiomers or diastereoisomers, if the case, of a compound of formula I, said compound may be obtained through a sterically controlled synthesis or by using reagents having the appropriate chirality or separating the desired isomer from the enantiomeric or diastereoisomeric mixture thereof according to conventional procedures. For instance, single optically active enantiomers may be obtained from their racemates by chiral chromatography or by converting them into a mixture of diastereoisomeric derivatives, separating the diastereoisomeric derivatives and restoring the respective enantiomers.

Diastereoisomers can be separated from their mixtures by means of conventional techniques based on their different physico-chemical properties, such as chromatography, distillation, or fractional crystallization.

Pharmacology

The compounds of the invention may be used for the manufacture of a medicament active as sodium and/or calcium channel modulators against disorders caused by dysfunctions of voltage gated calcium and/or sodium channels being characterized in that they are substantially free from any CYP2D6 inhibitory effect or exhibit a significantly reduced CYP2D6 inhibitory effect.

The sodium channel modulating activity of the fluorinated phenylalkylamino derivatives was measured through a fluorescence-based sodium influx assay (Table 1), through patch clamp techniques in constitutive and/or Nav 1.3 transfected cell lines (Table 2) and in cortical neurons.

The CYP2D6 inhibition was assessed by performing in vitro inhibition studies using Supersomes, microsomes derived from baculovirus infected insect cells; the baculoviruses have been engineered to express one or more drug metabolizing enzyme cDNAs (Table 3).

The in vivo analgesic activity of the above compounds was assessed in the "rat complete Freund's adjuvant model" and in the "Bennett model of neuropathic pain in rats".

The in vivo sodium channel blocking and anticonvulsant activity were measured using the "Maximal electroshock test" in mice (Table 4).

The anti mania activity was measured using the "Amphetamine and chlordiazepoxide-induced hyperlocomotion in mice" model.

The anti-schizophrenia and anti-addiction activities were assessed using the "Test of cognitive impairment in schizophrenia" and the "Cocaine-induced behavioural sensitization test" in rats.

"Acute bladder irritation by acetic acid in rats" and "Intermediate bladder irritation by cyclophosphamide in rats" tests were used as models for urological diseases.

The anti migraine activity was measured using the "migraine test" in rats.

Such substances exhibit also "use and frequency-dependency", i.e. an enhancement of the block during a high frequency stimulation when there is a large accumulation of channels in the inactivated state, such as in neuronal pathological conditions. Functionally, the use-dependent block results in depression of neuronal activity at high frequency firing and with lower blocking capacity at normal firing rate suggesting that the compounds of this invention may selectively depress abnormal activity of the calcium and/or sodium channels, leaving unaffected the physiological activity, thus decreasing CNS depressant effects (Catterall W. A., Trends Pharmacol. Sci. 8: 57-65 (1987)).

The compounds of the invention are active in vivo when orally or intraperitoneally administered in the range of 0.1 to 100 mg/kg in different animal models hereafter described.

In view of the above described mechanisms of action, the compounds of the present invention are useful in the prevention or treatment of neuropathic pain. Neuropathic pain syndromes include, and are not limited to: diabetic neuropathy; sciatica; non-specific lower back pain; multiple sclerosis pain; fibromyalgia; HIV-related neuropathy; neuralgia, such as post-herpetic neuralgia and trigeminal neuralgia, Morton's neuralgia, causalgia; and pain resulting from physical trauma, amputation, phantom limb, cancer, toxins or chronic inflammatory conditions; central pain such as the one observed in thalamic syndromes, mixed central and peripheral forms of pain such as complex regional pain syndromes (CRPS) also called reflex sympathetic dystrophies.

The compounds of the invention are also useful for the treatment of chronic pain. Chronic pain includes, and is not limited to, chronic pain caused by inflammation or an inflammatory-related condition, osteoarthritis, rheumatoid arthritis, acute injury or trauma, upper back pain or lower back pain (resulting from systematic, regional or primary spine disease such as radiculopathy), bone pain (due to osteoarthritis, osteoporosis, bone metastasis or unknown reasons), pelvic pain, spinal cord injury-associated pain, cardiac chest pain, non-cardiac chest pain, central post-stroke pain, myofascial pain, sickle cell pain, cancer pain, Fabry's disease, AIDS pain, geriatric pain or pain caused by headache, temporomandibular joint syndrome, gout, fibrosis or thoracic outlet syndromes, in particular rheumatoid arthritis and osteoarthritis.

The compounds of the invention are also useful in the treatment of acute pain caused by acute injury, illness, sport-medicine injuries, carpal tunnel syndrome, burns, musculoskeletal sprains and strains, musculotendinous strain, cervicobrachial pain syndromes, dyspepsia, gastric ulcer, duodenal ulcer, dysmenorrhea, endometriosis or surgery (such as open heart or bypass surgery), post operative pain, kidney stone pain, gallbladder pain, gallstone pain, obstetric pain or dental pain.

The compounds of the invention are also useful in the treatment of headaches such as migraine, tension type headache, transformed migraine or evolutive headache, cluster headache, as well as secondary headache disorders, such as the ones derived from infections, metabolic disorders or other systemic illnesses and other acute headaches, paroxysmal hemicrania and the like, resulting from a worsening of the above mentioned primary and secondary headaches.

The compounds of the invention are also useful for the treatment of neurological conditions such as epilepsy including simple partial seizure, complex partial seizure, secondary generalized seizure, further including absence seizure, myoclonic seizure, clonic seizure, tonic seizure, tonic clonic seizure and atonic seizure. The compounds of the invention are also useful for the treatment of neurodegenerative disorders of various origins such as Alzheimer's Disease and other dementia conditions such as Lewys body, fronto-temporal dementia and taupathies; amyotrophic lateral sclerosis, Parkinson's Disease and other parkinsonian syndromes; essential tremors; other spino cerebellar degeneration and Charcot-Marie-Toot neuropathy.

The compounds of the invention are also useful for the treatment of cognitive disorders and of psychiatric disorders. Psychiatric disorders include, and are not limited to major depression, dysthymia, mania, bipolar disorder (such as bipolar disorder type I, bipolar disorder type II), cyclothymic disorder, rapid cycling, ultradian cycling, mania, hypomania, schizophrenia, schizophreniform disorders, schizoaffective disorders, personality disorders, attention disorders with or without hyperactive behaviour, delusional disorders, brief psychotic disorders, shared psychotic disorders, psychotic disorder due to a general medical condition, substance-induced psychotic disorders or a psychotic disorder not otherwise specified, anxiety disorders such as generalised anxiety disorder, panic disorders, post-traumatic stress disorder, impulse control disorders, phobic disorders, dissociative states and moreover in smoke, drug addiction and alcoholism. In particular bipolar disorders, psychosis, anxiety and addiction.

Compounds of the invention are also useful in the treatment of diseases such as vertigo, tinnitus, muscle spasm, and other disorders including and not limited to cardiovascular diseases (such as cardiac arrhythmia, cardiac infarction or angina pectoris, hypertension, cardiac ischemia, cerebral ischemia) endocrine disorders (such as acromegaly or diabetes insipidus) diseases in which the pathophysiology of the disorder involves excessive or hypersecretory or otherwise inappropriate cellular secretion of an endogenous substance (such as catecholamine, a hormone or a growth factor).

The compounds of the invention are also useful in the selective treatment of liver disease, such as inflammatory liver diseases, for example chronic viral hepatitis B, chronic viral hepatitis C, alcoholic liver injury, primary biliary cirrhosis, autoimmune hepatitis, non-alcoholic steatohepatitis and liver transplant rejection.

The compounds of the invention inhibit inflammatory processes affecting all body systems. Therefore are useful in the treatment of inflammatory processes of the muscular-skeletal system of which the following is a list of examples but it is not comprehensive of all target disorders: arthritic conditions such as alkylosing spondylitis, cervical arthritis, fibromyalgia, gout, juvenile rheumatoid arthritis, lumbosacral arthritis, osteoarthritis, osteoporosis, psoriatic arthritis, rheumatic disease; disorders affecting skin and related tissues: eczema, psoriasis, dermatitis and inflammatory conditions such as sunburn; disorders of the respiratory system: asthma, allergic rhinitis and respiratory distress syndrome, lung disorders in which inflammation is involved such as asthma and bronchitis; chronic obstructive pulmonary disease; disorders of the immune and endocrinological systems: periarthritis nodosa, thyroiditis, aplastic anaemia, scleroderma, myasthenia gravis, multiple sclerosis and other demyelinizating disorders, encephalomyelitis, sarcoidosis, nephritic syndrome, Bechet's syndrome, polymyositis, gingivitis.

Compounds of the invention are also useful in the treatment of gastrointestinal (GI) tract disorders such as inflammatory bowel disorders including but not limited to ulcerative colitis, Crohn's disease, ileitis, proctitis, celiac disease, enteropathies, microscopic or collagenous colitis, eosinophilic gastroenteritis, or pouchitis resulting after proctocolectomy and post ileonatal anastomosis, and irritable bowel syndrome including any disorders associated with abdominal pain and/or abdominal discomfort such as pylorospasm, nervous indigestion, spastic colon, spastic colitis, spastic bowel, intestinal neurosis, functional colitis, mucous colitis, laxative colitis and functional dyspepsia; but also for treatment of atrophic gastritis, gastritis varialoforme, ulcerative colitis, peptic ulceration, pyrosis, and other damage to the GI tract, for example, by *Helicobacter pylori*, gastroesophageal reflux disease, gastroparesis, such as diabetic gastroparesis; and other functional bowel disorders, such as non-ulcerative dyspepsia (NUD); emesis, diarrhea, and visceral inflammation.

Compounds of the invention are also useful in the treatment of disorders of the genito-urinary tract such as overactive bladder, prostatitis (chronic bacterial and chronic non-bacterial prostatitis), prostadynia, interstitial cystitis, urinary incontinence and benign prostatic hyperplasia, annexitis, pelvic inflammation, bartholinitis and vaginitis. In particular overactive bladder and urinary incontinence.

The compounds of the invention are also useful in the treatment of ophthalmic diseases such as retinitis, retinopathies, uveitis and acute injury to the eye tissue, macular degeneration or glaucoma, conjunctivitis.

The compounds of the invention are also useful in the treatment of eating disorders such as anorexia nervosa including the subtypes restricting type and binge-eating/purging type; bulimia nervosa including the subtypes purging type and nonpurging type; obesity; compulsive eating disorders; binge eating disorder; and eating disorder not otherwise specified.

In consideration of the fact that the compounds of this invention are substantially free from any CYP2D6 inhibitory effect or exhibit a significantly reduced CYP2D6 inhibitory effect, the compounds of this invention are particularly useful for treating the above described disorders caused by dysfunctions of voltage gated sodium and/or calcium channel in patients that are defined as poor metabolizers or are assuming drugs which are CYP2D6 inhibitors.

It will be appreciated that the compounds of the invention may advantageously be used in conjunction with one or more other therapeutic agents. Examples of suitable agents for adjunctive therapy include a serotonin receptor modulator including a 5HT1B/1D agonist, such as a triptan (e.g. sumatriptan or naratriptan); an adenosine A1 agonist; an adenosine A2 antagonist; a purinergic P2X antagonist, an EP ligand; an NMDA modulator, such as a glycine antagonist; an AMPA modulator; a substance P antagonist (e.g. an NK1 antagonist); a cannabinoid; a nicotinic receptor agonist; an alpha-1 or 2 adrenergic agonist; acetaminophen or phenacetin; a 5-lipoxygenase inhibitor; a leukotriene receptor antagonist; a DMARD (e.g. methotrexate); gabapentin, pregabalin and related compounds; L-dopa and/or dopamine agonists; a catechol-O-methyltransferase inhibitor; a tricyclic antidepressant (e.g. amitryptiline); a neurone stabilising antiepileptic drug; a monoaminergic uptake inhibitor (e.g. venlafaxine); a matrix metalloproteinase inhibitor; a nitric oxide synthase (NOS) inhibitor, such as an iNOS or an nNOS inhibitor; a free radical scavenger; an alpha-synuclein aggregation inhibitor; a cholinesterase inhibitor, a cholesterol lowering agent; an alpha-secretase modulator; a beta-secretase modulator; a beta-amyloid aggregation inhibitor; an inhibitor of the release, or action, of tumor necrosis factor alpha; an antibody therapy, such as monoclonal antibody therapy; an antiviral agent, such as a nucleoside inhibitor (e.g. lamivudine) or an immune system modulator (e.g. interferon); an opioid analgesic, such as morphine; a vanilloid receptor antagonist; an analgesic, such as a cyclooxygenase-1 and/or cyclooxygenase-2 inhibitor; a local anaesthetic such as lidocaine and derivatives; a stimulant, including caffeine; an H2-antagonist (e.g. ranitidine); a proton pump inhibitor (e.g. omeprazole); an antacid (e.g. aluminium or magnesium hydroxide; an antiflatulent (e.g. simethicone); a decongestant (e.g. phenylephrine, phenylpropanolamine, pseudoephedrine, oxymetazoline, epinephrine, naphazoline, xylometazoline, propylhexedrine, or levo-desoxyephedrine, naphazoline, xylometazoline, propylhexedrine, or levo-desoxyephedrine); antitussive (e.g. codeine, hydrocodone, carmiphen, carbetapentane, or dextramethorphan); a diuretic; or a sedating or non-sedating antihistamine; an antipsychotic agent, including typical and atypical antipsychotics (e.g. haloperidol, risperidone, clozapine); an anti-depressant, such as a selective serotonin re-uptake inhibitors, serotonin and noradrenaline re-uptake inhibitors, MAO inhibitors and tryciclics antidepressant drugs; a mood stabilizer (e.g. lithium, lamotrigine, valproate); an anxyolitic agent (e.g. benzodiazepines, buspirone), beta-adrenergic receptors antagonists, morphine or morphine derivatives, other calcium or sodium channel blocker. It is to be understood that the present invention covers also the use of a compound of formula (I) or a pharmaceutically acceptable salt thereof in conjunction with one or more other therapeutic agents. For said use, the compounds of formula (I) and the other therapeutic agent(s) may be administered either jointly or sequentially.

The compounds of the present invention are useful in human and veterinary medicaments. It is to be understood that as used herein the terms "treatment" or "treating" whenever not specifically defined otherwise, include prevention, alleviation and cure of pathological affection, in particular, they include both treatment of established symptoms and prophylactic treatment. The compounds of the present invention for their therapeutic or preventive use in the above mentioned pathologies will be preferably used as active ingredients in a pharmaceutical composition.

Therefore, a further object of the present invention are pharmaceutical compositions containing a therapeutically effective amount of a compound of the invention or a salt thereof in admixture with a pharmaceutically acceptable carrier.

Accordingly, the expression "therapeutically effective" when referred to an "amount", a "dose" or "dosage" of the compounds of this invention is intended as an "amount", a "dose" or "dosage" of any said compounds sufficient for use in both treatment of the established symptoms and the prophylactic treatment of the above said pathological affections.

The pharmaceutical compositions object of the present invention may be administered in a variety of immediate and modified release dosage forms, e.g. orally, in the form of tablets, troches, capsules, sugar or film coated tablets, liquid solutions, emulsions or suspensions; rectally, in the form of suppositories; parenterally, e.g. by intramuscular and/or depot formulations; intravenous injection or infusion; locally and transdermally in form of patch and gel and cream.

Suitable pharmaceutically acceptable, therapeutically inert organic and/or inorganic carrier materials useful in the preparation of such composition include, for example, water, gelatin, arabic gum, lactose, starch, cellulose, magnesium stearate, talc, vegetable oils, cyclodextrins, polyalkyleneglycols and the like.

The composition comprising the fluorinated arylalkylaminocarboxamide derivatives of formula I as above defined can be sterilized and may contain further well known components, such as, for example, preservatives, stabilizers, wetting or emulsifying agents, e.g. paraffin oil, mannite monooleate, salts to adjust osmotic pressure, buffers and the like. For example, the solid oral forms may contain, together with the active ingredient, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disgregating agents, e.g. a starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The preparation of the pharmaceutical compositions object of the invention can be carried out according to common techniques.

The oral formulations comprise sustained release formulations that can be prepared in conventional manner, for instance by applying an enteric coating to tablets and granules.

The liquid dispersion for oral administration may be e.g. syrups, emulsions and suspensions.

The syrups may contain as carrier, for example, saccharose or saccharose with glycerine and/or mannitol and/or sorbitol.

Suspensions and emulsions may contain as a carrier, for example, a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusion may contain as carrier, for example, sterile water or preferably they may be in the form of sterile, aqueous, isotonic saline solutions.

The suppositories may contain, together with the active ingredient, a pharmaceutically acceptable carrier, e.g. cocoa butter, polyethylene glycol, a polyoxyethylene sorbitan fatty acid ester surfactant or lecithin.

The pharmaceutical compositions comprising the fluorinated arylalkylaminocarboxamide derivatives of formula I as above defined will contain, per dosage unit, e.g., capsule, tablet, powder injection, teaspoonful, suppository and the like from about 0.1 to about 500 mg of one or more active ingredients most preferably from 1 to 10 mg.

Optimal therapeutically effective doses to be administered may be readily determined by those skilled in the art and will vary, basically, with the strength of the preparation, with the mode of administration and with the advancement of the condition or disorder treated. In addition, factors associated with the particular subject being treated, including subject age, weight, diet and time of administration, will result in the need to adjust the dose to an appropriate therapeutically effective level.

Experimental Part

The $^{1}H$-NMR spectra are stored in solution of $CDCl_3$ or DMSO-$d_6$ with a Varian Gemini 200 MHz spectrometer. The chemical shifts are defined as d with $CDCl_3$ or DMSO-$d_6$ and $D_2O$ as internal standards.

The HPLC/MS analyses are performed with a Gilson instrument by utilizing a X-Terra RP18 column (5 μm, 4.6×50 mm) coupled to a UV detector (220 nm) and a Finnigan Aqa mass spectrometer (electron spray, positive ionization mode). General conditions utilized for the analyses: flow: 1.2 ml/min; column temperature: 50° C.; A/B elution gradient (eluent A: 0.1% formic acid in water; eluent B: 0.1% formic acid in acetonitrile): 5-95% of B from 0 to 8.0 minutes, 95% of B from 8.0 to 9.5 minutes.

Abbreviations which are used in the description of the schemes and the examples that follow are:

DCM: dichloromethane
EtAc: ethyl acetate
THF: tetrahydrofuran
PE: petroleum ether
DMF: dimethylformamide
DMSO: dimethylsulfoxide
DIPEA: diisopropylethylamine
NaH: sodium hydride
$LiAlH_4$: lithium aluminum hydride
LC/MS: Liquid Chromatography/Mass Spectrometry
TLC: Thin Layer Chromatography
RT: room temperature
$Boc_2O$: di-tert-butyl-dicarbonate

EXAMPLES

For better illustrating the invention the following examples are given.

Example 1-1

2-[2,2-Difluoro-2-(3-butoxyphenyl)-ethylamino]-N,N-dimethyl-acetamide, hydrochloride

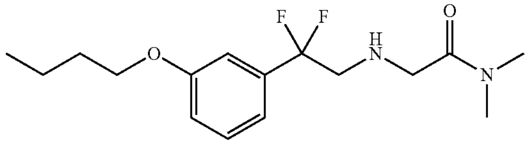 [SMILES: CCCCOc1cccc(C(F)(F)CNCC(=O)N(C)C)c1]

Formula: $C_{16}H_{2}4F_{2}N_{2}O_{2}$

MW: 314.36

Mass/charge ratio: 315.36 (MH+, ESI pos, 3.2KV, 25V, 350° C.)

$^{1}H$-NMR (300 MHz, DMSO-d6) δ ppm 9.58 (bs, 2H), 7.47 (t, 1H), 6.98-7.29 (m, 3H), 4.08 (s, 2H), 4.04 (t, 2H), 3.86 (t, 2H), 2.93 (s, 3H), 2.91 (s, 3H), 1.62-1.82 (m, 2H), 1.34-1.54 (m, 2H), 0.95 (t, 3H).

The above compound is synthesized according to Scheme 1

Scheme 1

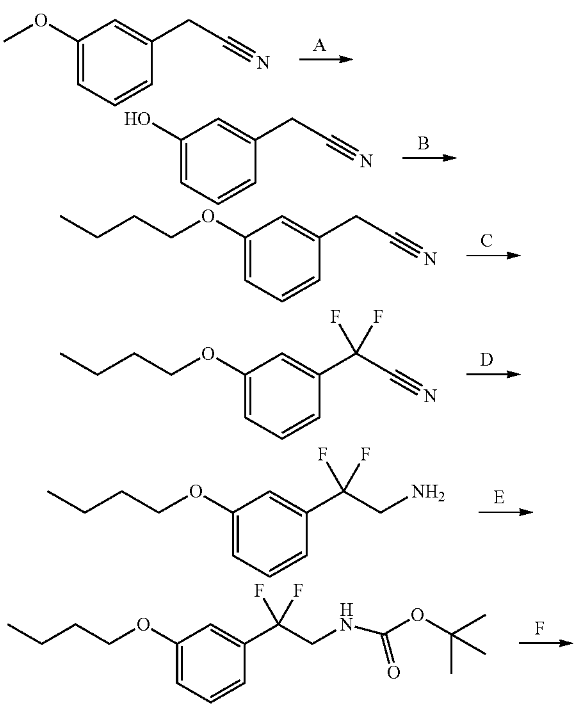

-continued

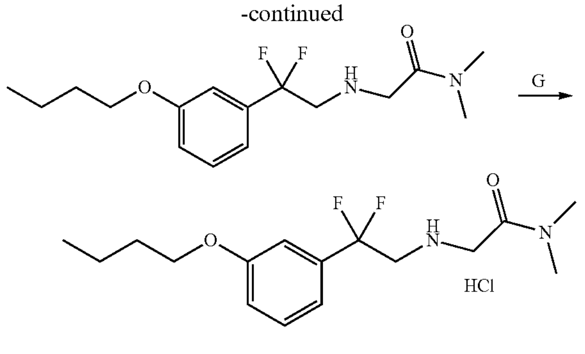

Step A

To a solution of 2-(3-methoxyphenyl)acetonitrile (2 g; 13.59 mmol) in 13 mL of dry DCM) cooled at 0° C. under nitrogen atmosphere, a 1M solution of $BBr_3$ in DCM (28.54 mmol; 28.54 mL) is slowly added dropwise. The mixture is stirred at room temperature for 20 hours. The reaction mixture is then poured into ice, water is added and the organic phase is extracted three times with DCM, washed with brine and dried over anhydrous $Na_2SO_4$. After evaporation, the crude mixture is chromatographed on silica gel using PE/EtAc (80/20) as an eluant, yielding 1.28 g (71%) of 2-(3-hydroxyphenyl)acetonitrile.

Step B

To a solution of 2-(3-hydroxyphenyl)acetonitrile (2.29 g; 17.11 mmol) in dry DMF (25 mL), $K_2CO_3$ (7.08 g; 51.33 mmol), KI (0.61 g; 3.70 mmol) and 1-bromobutane (4.69 g; 3.69 mL; 34.22 mmol) are added and the mixture is stirred at 60° C. for 5 hours and then at room temperature overnight. The reaction mixture is extracted with EtAc (150 mL) and washed with brine (150 mL): the aqueous phase is acidified with 0.1N HCl and extracted again with ethyl acetate. The combined organic phases are dried over anhydrous $Na_2SO_4$, filtered and evaporated. The crude mixture is purified by flash-chromatography (eluant: PE/EtAc 99/1) yielding, after evaporation, 3.07 g (95%) of 2-(3-butoxyphenyl)acetonitrile.

Step C

A solution of 2-(3-butoxyphenyl)acetonitrile (903 mg; 4.80 mmol) in dry THF (75 mL) is cooled at −78° C. and tert-butyllithium (1.6M in pentane; 6.6 mL; 10.56 mmol) is added dropwise while maintaining the internal temperature between −75° C. and −78° C. The solution is stirred for 10 minutes at −78° C. then a solution of N-fluorobenzenesulfonimide (N-FSI; 3.78 g; 12.00 mmol) in dry THF (12 mL) is added within 15 minutes. The reaction mixture is stirred at −78° C. for 2 hours then quenched with 0.01 N HCl at −78° C. and brought to room temperature. Ethyl acetate (50 mL) is then added and the mixture evaporated. 1.79 g of benzenesulfonamide side-product precipitate (white solid) is filtered off. The solution is washed with brine and dried over anhydrous $Na_2SO_4$. After evaporation, the crude residue is flash-chromatographed (eluant; petroleum ether/ethyl acetate, 99.5/0.5 then petroleum PE/EtAc, 99/1) to give 559 mg (52%) of pure 2,2-difluoro-[2-(-3-methoxphenyl)]acetonitrile and further 355 mg of the same product to be further purified.

Step D

A solution of $AlCl_3$ (400 mg; 3.00 mmol) in dry ethyl ether (6 mL) is stirred at 0° C. for 30

A pre-cooled (0° C.) suspension of $LiAlH_4$ (1M in THF; 3.00 mmol) is added to that mixture. After 5 minutes a pre-cooled (0° C.) solution of 2,2-difluoro-[2-(-3-methoxphenyl)]acetonitrile in dry THF (9 ml) is added. After 2 hours at 0° C. the reaction is completed. The solution is quenched with few drops of saturated $NaHCO_3$, extracted three times with EtAc, dried over anhydrous $Na_2SO_4$, filtered and evaporated. 2,2-Difluoro-2-(3-butoxyphenyl)ethylamine (587 mg) is obtained and used as a crude residue in Step E below.

Step E 509 mg (2.22 mmol) of 2,2-difluoro-2-(3-butoxyphenyl)ethylamine in 41 mL of dry THF is stirred at room temperature while di-tert-butyldicarbonate ($Boc_2O$) and $Et_3N$ are added. The mixture is stirred at room temperature for 24 hours. The solvent is evaporated and the crude residue is purified by flash-chromatography using PE/EtAc, 97/3, as an eluant. N-(tert-butoxycarbonyl)-2,2-difluoro-2-(3-butoxyphenyl)ethylamine was obtained as an off-white solid (481 mg, 66%).

Step F 150 mg (0.46 mmol) of N-(tert-butoxycarbonyl)-2,2-difluoro-2-(3-butoxyphenyl)ethylamine are dissolved in dry DMF (2.5 mL) and the solution was cooled to 0° C. NaH (60% in mineral oil; 22 mg; 0.55 mmol) is added and the reaction mixture stirred for 10 minutes at 0° C. and for further 10 minutes at room temperature. The reaction mixture is cooled again at 0° C., then N,N-dimethylchloroacetamide (73 mg; 0.60 mmol) is added and stirring is continued for 24 hours at room temperature. The reaction is quenched with water, extracted three times with EtAc, washed with brine. The organic phases are dried over anhydrous $Na_2SO_4$, filtered and evaporated. The residue is flash-chromatographed on silica gel (eluant: DCM/EtAc, from 98/2 to 95/5). 2-[N'-(tert-butoxycarbonyl)-2,2-difluoro-2-(3-butoxyphenyl)-ethylamino]-N,N-dimethyl-acetamide (165 mg; 87%) is obtained as a white solid.

Step G

2-[N'-(tert-Butoxycarbonyl)-2,2-difluoro-2-(3-butoxyphenyl)-ethylamino]-N,N-dimethyl-acetamide (160 mg; 0.39 mmol) is dissolved in DCM (5 mL) then 0.6 mL (2.4 mmol) of 4M HCl in dioxane are added and the reaction mixture allowed to stand overnight. Further 2 eq (0.2 mL) of 4M HCl in dioxane (total 0.8 mL) are added and the mixture is stirred overnight. The solvent is evaporated, diethyl ether is added and then evaporated to give 139 mg (100%) of white solid 2-[2,2-difluoro-2-(3-butoxyphenyl)-ethylamino]-N,N-dimethyl-acetamide, hydrochloride (Example 1-1).

Examples 1-2 to 1-42

These compounds are prepared according to the same procedure described in Scheme 1 using the suitable reagents.

Example 1-2

2-[2,2-Difluoro-2-(3-pentyloxyphenyl)-ethylamino]-N,N-dimethyl-acetamide, hydrochloride

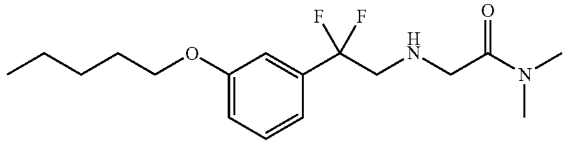 [SMILES: CCCCCOc1cccc(C(F)(F)CNCC(=O)N(C)C)c1]

Formula: $C_{17}H_{26}F_2N_2O_2$
MW: 328.41
Mass/charge ratio: 329.25 (MH+, ESI pos, 3.2KV, 25V, 350° C.)

$^1$H-NMR (300 MHz, DMSO-d6) δ ppm 9.37 (bs, 2H), 7.47 (t, 1H), 7.02-7.24 (m, 3H), 4.06 (s, 2H), 4.03 (t, 2H), 3.83 (t, 2H), 2.93 (s, 3H), 2.90 (s, 3H), 1.74 (q, 2H), 1.28-1.50 (m, 2H), 0.91 (t, 3H).

Example 1-3

2-[2,2-Difluoro-2-(3-butoxyphenyl)-ethylamino]-N,N-dipropyl-acetamide, hydrochloride

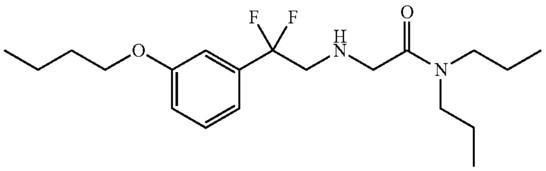 [SMILES: CCCCOc1cccc(C(F)(F)CNCC(=O)N(CCC)CCC)c1]

Formula: $C_{20}H_{32}F_2N_2O_2$
MW: 370.49
Mass/charge ratio: 371.10 (MH+, ESI pos, 3.2KV, 25V, 350° C.)

$^1$H-NMR (300 MHz, DMSO-d6) δ ppm 8.84 (bs, 2H), 7.48 (t, 1H), 7.02-7.26 (m, 3H), 4.03 (s, 2H), 3.94 (s, 2H), 3.78 (t, 2H), 3.21-3.29 (m, 2H), 3.06-3.19 (m, 2H), 1.64-1.79 (m, 2H), 1.37-1.61 (m, 2H), 0.95 (t, 3H), 0.86 (t, 3H), 0.64 (t, 3H).

Example 1-4

2-[2,2-Difluoro-2-(3-butoxy-4-methylphenyl)-ethylamino]-N,N-dimethyl-acetamide, hydrochloride

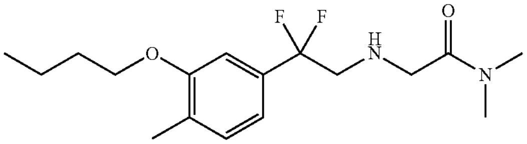 [SMILES: CCCCOc1cc(C(F)(F)CNCC(=O)N(C)C)ccc1C]

Formula: $C_{17}H_{26}F_2N_2O_2$
MW: 328.41
Mass/charge ratio: 329.08 (MH+, ESI pos, 3.2KV, 25V, 350° C.)

$^1$H-NMR (300 MHz, DMSO-d6) δ ppm 9.44 (bs, 2H), 7.15-7.17 (tdd, 3H), 4.03 (s, 2H), 4.03 (t, 2H), 3.81 (s, 2H), 3.09 (s, 2H), 2.80 (s, 3H), 2.78 (s, 3H), 2.13 (s, 3H), 1.77 (tt, 2H), 1.40 (tq, 2H), 0.88 (t, 3H).

Example 1-5

2-[2,2-Difluoro-2-(3-butoxyphenyl)-ethylamino]-N,N-dibutyl-acetamide, hydrochloride

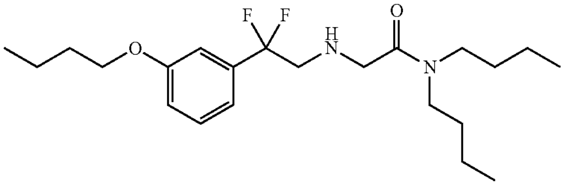 [SMILES: CCCCOc1cccc(C(F)(F)CNCC(=O)N(CCCC)CCCC)c1]

Formula: $C_{22}H_{36}F_2N_2O_2$
MW: 398.54
Mass/charge ratio: 399.33 (MH+, ESI pos, 3.2KV, 25V, 350° C.)

Example 1-6

2-[2,2-Difluoro-2-(3-hexyloxyphenyl)-ethylamino]-N,N-dimethyl-acetamide, hydrochloride

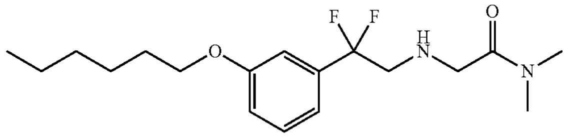 [SMILES: CCCCCCOc1cccc(C(F)(F)CNCC(=O)N(C)C)c1]

Formula: $C_{18}H_{28}F_2N_2O_2$
MW: 342.43
Mass/charge ratio: 343.31 (MH+, ESI pos, 3.2KV, 25V, 350° C.)

$^1$H-NMR (300 MHz, DMSO-d6) δ ppm 9.47 (bs, 2H), 7.47 (t, 1H), 7.03-7.24 (m, 3H), 4.03 (s, 2H), 3.84 (t, 2H), 3.83 (s, 2H), 2.93 (s, 3H), 2.90 (s, 3H), 1.64-1.81 (m, 2H), 1.36-1.54 (m, 2H), 1.22-1.37 (m, 4H); 0.89 (t, 3H).

Example 1-7

2-{2,2-Difluoro-2-[3-(4,4,4-trifluorobutoxy)-phenyl]-ethylamino}-N,N-dimethyl-acetamide, hydrochloride

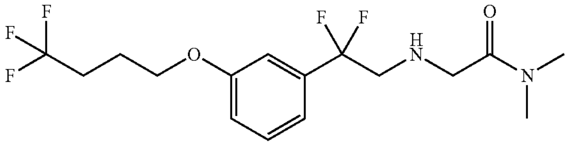 [SMILES: CN(C)C(=O)CNCC(F)(F)c1cccc(OCCCC(F)(F)F)c1]

Formula: $C_{16}H_{21}F_5N_2O_2$
MW: 368.35
Mass/charge ratio: 369.20 (MH+, ESI pos, 3.2KV, 25V, 400° C.)

$^1$H-NMR (300 MHz, DMSO-d6) δ ppm 9.41 (bs, 2H), 7.43-7.58 (m, 1H), 6.99-7.29 (m, 3H), 4.11 (t, 2H), 4.06 (t, 2H), 3.84 (t, 2H), 2.93 (s, 3H), 2.90 (s, 3H), 2.31-2.48 (m, 2H), 1.86-2.09 (m, 2H), 1.22-1.37 (m, 4H); 0.89 (t, 3H).

Example 1-8

2-[2,2-Difluoro-2-(3-pentyloxyphenyl)-ethylamino]-N,N-dipropyl-acetamide, hydrochloride

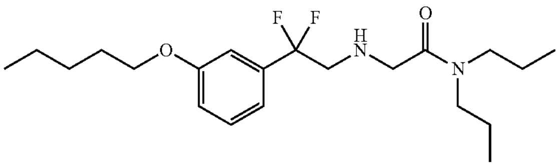 [SMILES: CCCCCOc1cccc(C(F)(F)CNCC(=O)N(CCC)CCC)c1]

Formula: $C_{21}H_{34}F_2N_2O_2$
MW: 384.51
Mass/charge ratio: 385.22 (MH+, ESI pos, 3.2KV, 25V, 350° C.)

$^1$H-NMR (300 MHz, DMSO-d6) δ ppm 8.82 (bs, 1H), 7.48 (t, 1H), 7.03-7.29 (m, 3H), 4.04 (s, 2H), 3.91 (s, 2H), 3.80 (t, 2H), 3.21-3.28 (m, 2H), 3.06-3.19 (m, 2H), 1.64-1.79 (m, 2H), 1.37-1.61 (m, 4H), 0.92 (t, 3H), 0.87 (t, 3H), 0.63 (t, 3H).

Example 1-9

2-{2,2-Difluoro-2-[3-(3-(3-fluorophenyl)-propoxy)-phenyl]-ethylamino}-N,N-dimethyl-acetamide, hydrochloride

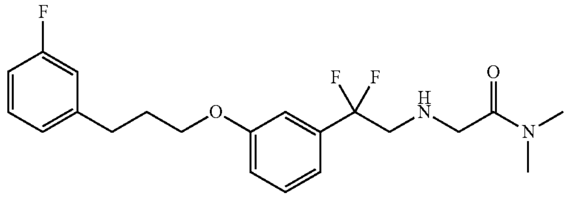 [SMILES: CN(C)C(=O)CNCC(F)(F)c1cccc(OCCCc2cccc(F)c2)c1]

Formula: $C_{21}H_{25}F_3N_2O_2$

MW: 394.44

Mass/charge ratio: 395.19 (MH+, ESI pos, 3.2KV, 25V, 400° C.).

Example 1-10

2-{2,2-Difluoro-2-[3-(3-(3-chlorophenyl)-propoxy)-phenyl]-ethylamino}-N,N-dimethyl-acetamide, hydrochloride

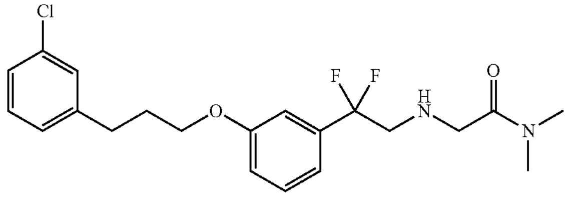

Formula: $C_{21}H_{25}ClF_2N_2O_2$

MW: 410.90

Mass/charge ratio: 411.75 (MH+, ESI pos, 3.2KV, 25V, 400° C.).

Example 1-11

2-[2,2-Difluoro-2-(3-butoxy-2-fluorophenyl)-ethylamino]-N,N-dimethyl-acetamide, hydrochloride

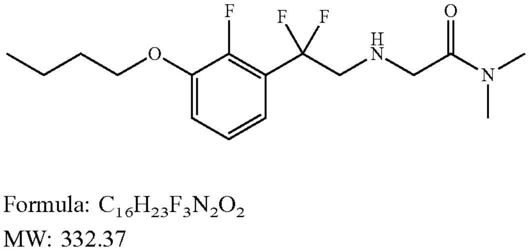

Formula: $C_{16}H_{23}F_3N_2O_2$

MW: 332.37

Mass/charge ratio: 33.15 (MH+, ESI pos, 3.2KV, 25V, 350° C.).

Example 1-12

2-{2,2-Difluoro-2-[3-(3-phenylpropoxy)-phenyl]-ethylamino}-N,N-dimethyl-acetamide, hydrochloride

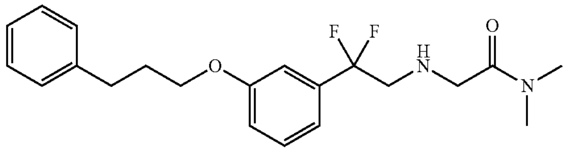 [SMILES: CN(C)C(=O)CNCC(F)(F)c1cccc(OCCCc2ccccc2)c1]

Formula: $C_{21}H_{26}F_2N_2O_2$

MW: 376.45

Mass/charge ratio: 377.28 (MH+, ESI pos, 3.2KV, 25V, 400° C.).

Example 1-13

2-{2,2-Difluoro-2-[3-(3-thiazol-2-yl-propoxy)-phenyl]-ethylamino}-N,N-dimethyl-acetamide, hydrochloride

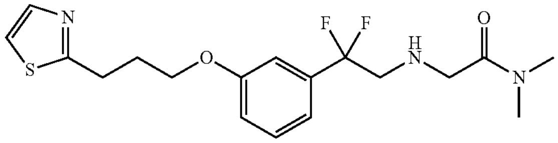 [SMILES: CN(C)C(=O)CNCC(F)(F)c1cccc(OCCCc2nccs2)c1]

Formula: $C_{18}H_{23}F_2N_3O_2S$

MW: 383.46

Mass/charge ratio: 384.22 (MH+, ESI pos, 3.2KV, 25V, 350° C.).

Example 1-14

2-[2,2-Difluoro-2-(3-benzyloxyphenyl)-ethylamino]-N,N-dimethyl-acetamide, hydrochloride

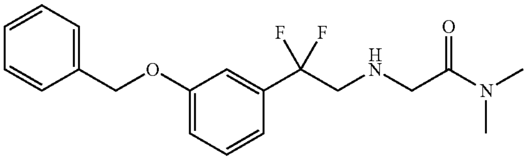 [SMILES: CN(C)C(=O)CNCC(F)(F)c1cccc(OCc2ccccc2)c1]

Formula: $C_{19}H_{22}F_2N_2O_2$

MW: 348.40

Mass/charge ratio: 349.22 (MH+, ESI pos, 3.2KV, 15V, 400° C.).

$^1$H-NMR (300 MHz, DMSO-d6) δ ppm 9.40 (bs, 1H), 7.29-7.60 (m, 6H), 7.09-7.29 (m, 3H), 5.18 (s, 2H), 4.04 (s, 2H), 3.83 (t, 2H), 2.93 (s, 3H), 2.90 (s, 3H).

Example 1-15

2-[2,2-Difluoro-2-(3-butoxyphenyl)-ethylamino]-1-(pyrrolidin-1-yl)-ethanone, hydrochloride

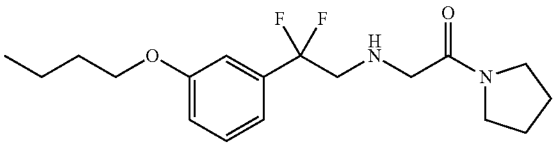 [SMILES: CCCCOc1cccc(C(F)(F)CNCC(=O)N2CCCC2)c1]

Formula: $C_{18}H_{26}F_2N_2O_2$

MW: 340.42

Mass/charge ratio: 341.02 ($MH^+$, ESI pos, 3.2KV, 25V, 400° C.).

$^1$H-NMR (300 MHz, DMSO-d6) δ ppm 9.34 (bs, 1H), 7.47 (t, 1H), 7.07-7.21 (m, 3H), 4.03 (t, 2H), 3.94 (s, 2H), 3.84 (t, 2H), 3.36 (t, 4H), 1.85-2.01 (m, 2H), 1.76-1.85 (m, 2H), 1.64-1.76 (m, 2H), 1.45 (m, 2H), 0.95 (t, 3H).

Example 1-16

2-[2,2-Difluoro-2-(3-butoxyphenyl)-ethylamino]-N-methyl-N-phenyl-acetamide, hydrochloride

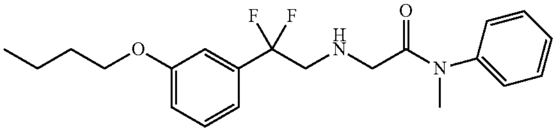 [SMILES: CCCCOc1cccc(C(F)(F)CNCC(=O)N(C)c2ccccc2)c1]

Formula: $C_{21}H_{26}F_2N_2O_2$

MW: 376.45

Mass/charge ratio: 347.23 ($MH^+$, ESI pos, 3.2KV, 25V, 400° C.).

Example 1-17

2-{2,2-Difluoro-2-[3-(3-phenylpropoxy)-phenyl]-ethylamino}-1-(pyrrolidin-1-yl)-ethanone, hydrochloride

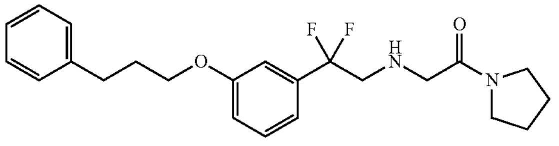 [SMILES: O=C(CNCC(F)(F)c1cccc(OCCCc2ccccc2)c1)N1CCCC1]

Formula: $C_{23}H_{28}F_2N_2O_2$

MW: 402.49

Mass/charge ratio: 403.26 ($MH^+$, ESI pos, 3.2KV, 15V, 400° C.).

Example 1-18

2-{2,2-Difluoro-2-[3-(4,4,4-trifluorobutoxy)-phenyl]-ethylamino}-1-(pyrrolidin-1-yl)-ethanone

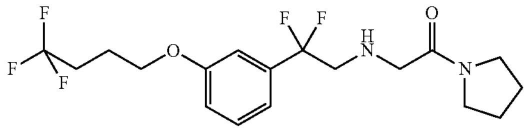 [SMILES: O=C(CNCC(F)(F)c1cccc(OCCCC(F)(F)F)c1)N1CCCC1]

Formula: $C_{18}H_{23}F_5N_2O_2$

MW: 394.39

Mass/charge ratio: 395.23 ($MH^+$, ESI pos, 3.2KV, 25V, 400° C.).

$^1$H-NMR (300 MHz, DMSO-d6) δ ppm 9.48 (bs, 2H), 7.35-7.61 (m, 1H), 7.01-7.26 (m, 3H), 4.11 (t, 2H), 3.96 (s, 2H), 3.86 (t, 2H), 3.28-3.40 (m, 4H), 2.33-2.48 (m, 2H), 1.68-2.04 (m, 6H).

Example 1-19

2-[2,2-Difluoro-2-(3-benzyloxy-phenyl)-ethylamino]-1-(morpholin-4-yl)-ethanone, hydrochloride

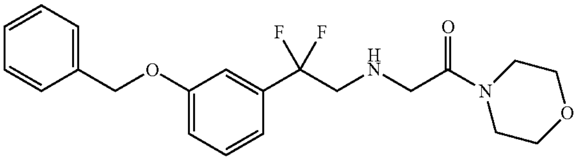 [SMILES: O=C(CNCC(F)(F)c1cccc(OCc2ccccc2)c1)N1CCOCC1]

Formula: $C_{21}H_{24}F_5N_2O_3$

MW: 390.43

Mass/charge ratio: 391.22 ($MH^+$, ESI pos, 3.2KV, 25V, 400° C.).

Example 1-20

2-{2,2-Difluoro-2-[3-(3-phenylpropoxy)-phenyl]-ethylamino}-1-(morpholin-4-yl)-ethanone, hydrochloride

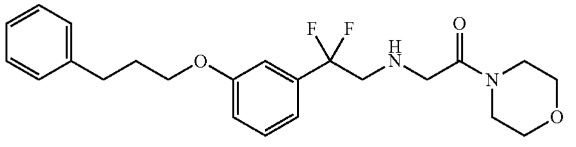 [SMILES: O=C(CNCC(F)(F)c1cccc(OCCCc2ccccc2)c1)N1CCOCC1]

Formula: $C_{23}H_{28}F_2N_2O_3$

MW: 418.49

Mass/charge ratio: 419.18 ($MH^+$, ESI pos, 3.2KV, 25V, 400° C.).

Example 1-21

2-{2,2-Difluoro-2-[3-(4,4,4-trifluorobutoxy)-phenyl]-ethylamino}-1-(morpholin-4-yl)-ethanone, hydrochloride

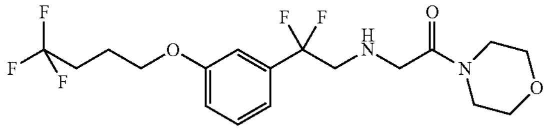 [SMILES: O=C(CNCC(F)(F)c1cccc(OCCCC(F)(F)F)c1)N1CCOCC1]

Formula: $C_{18}H_{23}F_5N_2O_3$

MW: 410.39

Mass/charge ratio: 411.22 ($MH^+$, ESI pos, 3.2KV, 15V, 400° C.).

$^1$H-NMR (300 MHz, DMSO-d6) δ ppm 9.70 (bs, 2H), 7.50 (t, 1H), 6.88-7.37 (m, 3H), 4.15 (s, 2H), 4.12 (t, 2H), 3.87 (t, 2H), 3.54-3.67 (m, 4H), 3.44-3.54 (m, 2H), 3.32-3.44 (m, 2H), 2.32-2.47 (m, 2H), 1.86-2.06 (m, 2H).

Example 1-22

2-[2,2-Difluoro-2-(3-butoxyphenyl)-ethylamino)1-(2H-benzo[b][1,4]oxazin-4(3H)-yl)-ethanone, hydrochloride

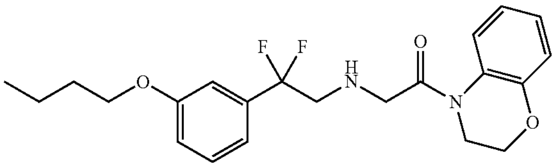 [SMILES: CCCCOc1cccc(C(F)(F)CNCC(=O)N2CCOc3ccccc32)c1]

Formula: $C_{22}H_{26}F_2N_2O_3$

MW: 404.46

Mass/charge ratio: 405.29 ($MH^+$, ESI pos, 3.2KV, 25V, 400° C.).

Example 1-23

2-[2,2-Difluoro-2-(3-benzyloxyphenyl)-ethylamino]-1-(pyrrolidin-1-yl)-ethanone, hydrochloride

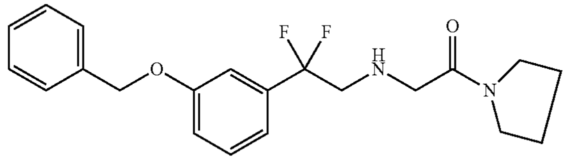 [SMILES: O=C(CNCC(F)(F)c1cccc(OCc2ccccc2)c1)N1CCCC1]

Formula: $C_{21}H_{24}F_2N_2O_2$

MW: 374.43

Mass/charge ratio: 375.27 ($MH^+$, ESI pos, 3.2KV, 25V, 350° C.).

Example 1-24

2-{2,2-Difluoro-2-[3-(3-phenylpropoxy)-phenyl]-ethylamino}-N-methyl-N-phenyl-acetamide, hydrochloride

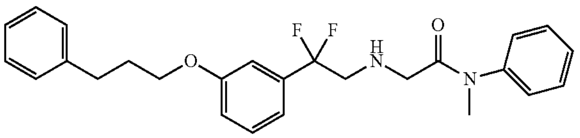 [SMILES: CN(C(=O)CNCC(F)(F)c1cccc(OCCCc2ccccc2)c1)c1ccccc1]

Formula: $C_{26}H_{28}F_2N_2O_2$

MW: 438.52

Mass/charge ratio: 439.38 ($MH^+$, ESI pos, 3.2KV, 25V, 350° C.).

Example 1-25

2-{2,2-Difluoro-2-[3-(4,4,4-trifluorobutoxy)-phenyl]-ethylamino}-N-methyl-N-phenyl-acetamide, hydrochloride

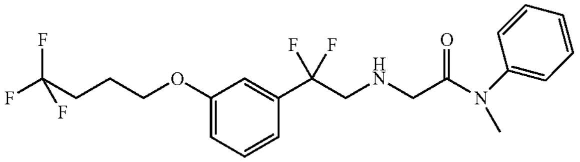 [SMILES: CN(C(=O)CNCC(F)(F)c1cccc(OCCCC(F)(F)F)c1)c1ccccc1]

Formula: $C_{21}H_{23}F_5N_2O_2$

MW: 430.42

Mass/charge ratio: 431. 29 ($MH^+$, ESI pos, 3.2KV, 25V, 350° C.).

Example 1-26

2-[2,2-Difluoro-2-(3-butoxyphenyl)-ethylamino]-1-(4-methylpiperazin-1-yl)-ethanone, hydrochloride

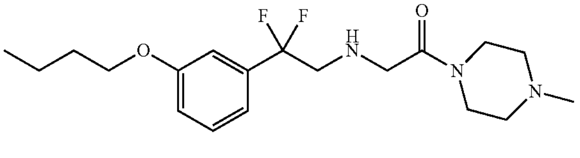 [SMILES: CCCCOc1cccc(C(F)(F)CNCC(=O)N2CCN(C)CC2)c1]

Formula: $C_{19}H_{29}F_2N_3O_2$

MW: 369.46

Mass/charge ratio: 370.07 ($MH^+$, ESI pos, 3.2KV, 15V, 400° C.).

$^1$H-NMR (300 MHz, DMSO-d6) δ ppm 7.28-7.49 (m, 1H), 6.92-7.18 (m, 3H), 4.04 (t, 2H), 3.62-3.85 (m, 1H), 3.52 (s, 2H), 3.32 (t, 2H), 2.87-3.19 (m, 8H), 2.69 (s, 3H), 1.61-1.84 (m, 2H), 1.48 (dq, 2H), 0.96 (t, 3H).

Example 1-27

2-{2,2-Difluoro-2-[3-(3-phenylpropoxy)-phenyl)-ethylamino}-1-(4-methylpiperazin-1-yl)-ethanone, hydrochloride

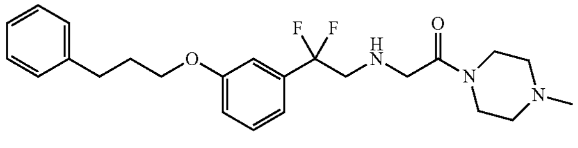 [SMILES: CN1CCN(C(=O)CNCC(F)(F)c2cccc(OCCCc3ccccc3)c2)CC1]

Formula: $C_{24}H_{31}F_2N_3O_2$

MW: 431.53

Mass/charge ratio: 431.37 ($MH^+$, ESI pos, 3.2KV, 15V, 400° C.).

Example 1-28

2-{2,2-Difluoro-2-[3-(4,4,4-trifluorobutoxy)-phenyl)-ethylamino}-1-(4-methylpiperazin-1-yl)-ethanone, hydrochloride

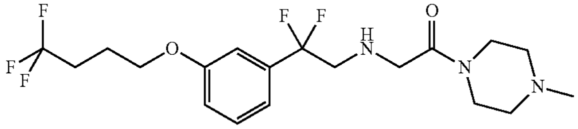 [SMILES: CN1CCN(C(=O)CNCC(F)(F)c2cccc(OCCCC(F)(F)F)c2)CC1]

Formula: $C_{19}H_{26}F_5N_3O_2$

MW: 423.43

Mass/charge ratio: 424.28 ($MH^+$, ESI pos, 3.2KV, 25V, 400° C.).

$^1$H-NMR (300 MHz, DMSO-d6) δ ppm 11.56 (bs, 1H), 9.57 (bs, 1H), 7.37-7.60 (m, 1H), 6.99-7.28 (m, 3H), 4.29-4.59 (m, 1H), 4.16-4.30 (m, 1H), 4.11 (t, 2H), 3.80 (t, 2H), 2.87-3.94 (m, 8H), 2.77 (s, 3H), 2.33-2.47 (m, 2H), 1.85-2.06 (m, 2H).

Example 1-29

2-[2,2-Difluoro-2-(3-butoxyphenyl)-ethylamino]-1-(piperidin-1-yl)-ethanone, hydrochloride

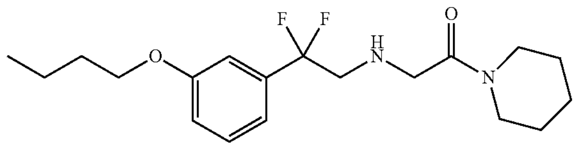 [SMILES: CCCCOc1cccc(C(F)(F)CNCC(=O)N2CCCCC2)c1]

Formula: $C_{19}H_{28}F_2N_2O_2$

MW: 354.44

Mass/charge ratio: 355.03 ($MH^+$, ESI pos, 3.2KV, 15V, 400° C.).

$^1$H-NMR (300 MHz, DMSO-d6) δ ppm 9.37 (bs, 2H), 7.47 (t, 1H), 7.04-7.21 (m, 3H), 4.07 (s, 2H), 3.84 (t, 2H), 3.45-3.54 (m, 2H), 3.21-3.32 (m, 2H), 1.66-1.81 (m, 2H), 1.33-1.66 (m, 8H), 0.95 (t, 3H).

Example 1-30

2-{2,2-Difluoro-2-[3-(3-phenylpropoxy)-phenyl]-ethylamino}-1-(piperidin-1-yl)-ethanone, hydrochloride

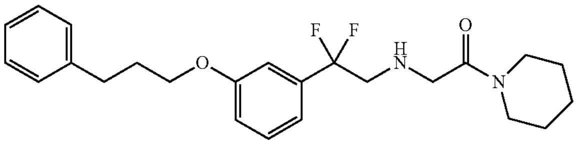 [SMILES: O=C(CNCC(F)(F)c1cccc(OCCCc2ccccc2)c1)N1CCCCC1]

Formula: $C_{24}H_{30}F_2N_2O_2$

MW: 416.52

Mass/charge ratio: 417.34 ($MH^+$, ESI pos, 3.2KV, 15V, 350° C.).

Example 1-31

2-{2,2-Difluoro-2-[3-(4,4,4-trifluorobutoxy)-phenyl]-ethylamino}-1-(piperidin-1-yl)-ethanone, hydrochloride

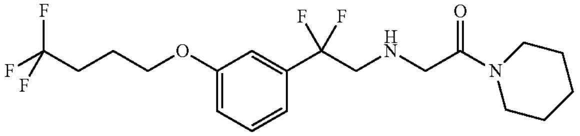 [SMILES: O=C(CNCC(F)(F)c1cccc(OCCCC(F)(F)F)c1)N1CCCCC1]

Formula: $C_{19}H_{25}F_5N_2O_2$

MW: 408.41

Mass/charge ratio: 408.07 ($MH^+$, ESI pos, 3.2KV, 15V, 350° C.).

Example 1-32

2-[2,2-Difluoro-2-(3-butoxyphenyl)-ethylamino]-N,N-diethyl-acetamide, hydrochloride

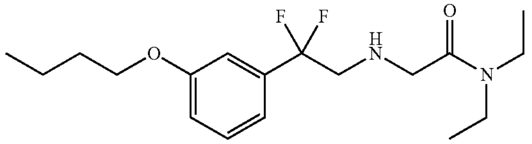 [SMILES: CCCCOc1cccc(C(F)(F)CNCC(=O)N(CC)CC)c1]

Formula: $C_{18}H_{28}F_2N_2O_2$

MW: 342.43

Mass/charge ratio: 343.05 (MH+, ESI pos, 3.2KV, 15V, 350° C.)

$^1$H-NMR (300 MHz, DMSO-d6) δ ppm 7.47 (t, 1H), 7.07-7.20 (m, 3H), 4.03 (t, 2H), 4.02 (s, 2H), 3.84 (t, 2H), 3.34 (q, 2H), 3.24 (q, 2H), 1.64-1.82 (m, 2H), 1.36-1.55 (m, 2H), 1.12 (t, 3H), 1.07 (t, 3H), 0.95 (t, 3H).

Example 1-33

2-{2,2-Difluoro-2-[3-(2-fluorobenzyloxy)-phenyl]-ethylamino}-N,N-dimethyl-acetamide, hydrochloride

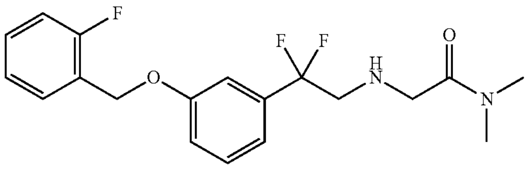 [SMILES: CN(C)C(=O)CNCC(F)(F)c1cccc(OCc2ccccc2F)c1]

Formula: $C_{19}H_{21}F_3N_2O_2$

MW: 366.39

Mass/charge ratio: 367.18 (MH+, ESI pos, 3.2KV, 15V, 400° C.).

Example 1-34

2-[2,2-Difluoro-2-(3-butoxyphenyl)-ethylamino]-1-(cis-3,5-dimethylpiperidin-1-yl)-ethanone, hydrochloride

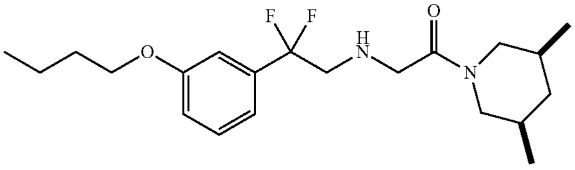 [SMILES: CCCCOc1cccc(C(F)(F)CNCC(=O)N2C[C@H](C)C[C@H](C)C2)c1]

Formula: $C_{21}H_{32}F_2N_2O_2$

MW: 382.50

Mass/charge ratio: 383.34 ($MH^+$, ESI pos, 3.2KV, 15V, 350° C.).

Example 1-35

2-[2,2-Difluoro-2-(3-butoxyphenyl)-ethylamino]-1-(3,4-dihydroisoquinolin-2(1H)-yl)-ethanone, hydrochloride

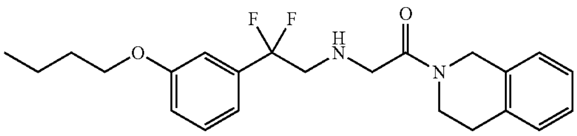 [SMILES: CCCCOc1cccc(C(F)(F)CNCC(=O)N2CCc3ccccc3C2)c1]

Formula: $C_{23}H_{28}F_2N_2O_2$

MW: 402.49

Mass/charge ratio: 403.22 ($MH^+$, ESI pos, 3.2KV, 25V, 350° C.).

Example 1-36

2-[2,2-Difluoro-2-(3-butoxyphenyl)-ethylamino]-N,N-diisopropyl-acetamide, hydrochloride

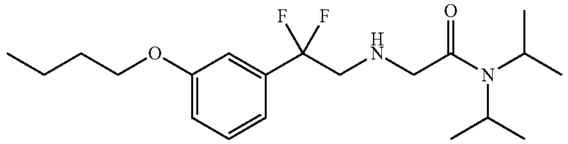 [SMILES: CCCCOc1cccc(C(F)(F)CNCC(=O)N(C(C)C)C(C)C)c1]

Formula: $C_{20}H_{32}F_2N_2O_2$

MW: 370.49

Mass/charge ratio: 371.19 ($MH^+$, ESI pos, 3.2KV, 25V, 350° C.).

Example 1-37

2-[2,2-Difluoro-2-(3-butoxyphenyl)-ethylamino]-N-cyclohexyl-N-methyl-acetamide, hydrochloride

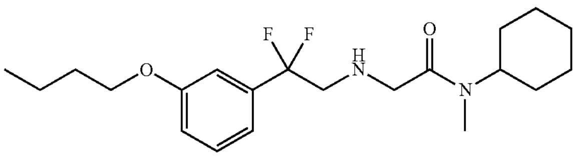 [SMILES: CCCCOc1cccc(C(F)(F)CNCC(=O)N(C)C2CCCCC2)c1]

Formula: $C_{21}H_{32}F_2N_2O_2$

MW: 382.50

Mass/charge ratio: 383.31 ($MH^+$, ESI pos, 3.2KV, 25V, 400° C.).

Example 1-38

2-[2,2-Difluoro-2-(3-benzyloxyphenyl)-ethylamino]-1-(piperidin-1-yl)-ethanone, hydrochloride

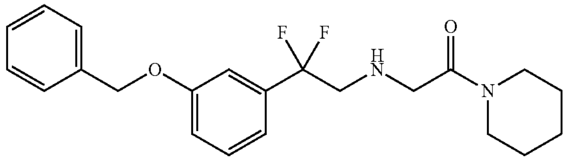 [SMILES: O=C(CNCC(F)(F)c1cccc(OCc2ccccc2)c1)N1CCCCC1]

Formula: $C_{21}H_{32}F_2N_2O_2$

MW: 388.46

Mass/charge ratio: 389.21 ($MH^+$, ESI pos, 3.2KV, 25V, 400° C.).

Example 1-39

2-[2,2-Difluoro-2-(3-butoxyphenyl)-ethylamino]-1-[4-(phenylsulfonyl)-piperazin-1-yl]-ethanone, hydrochloride

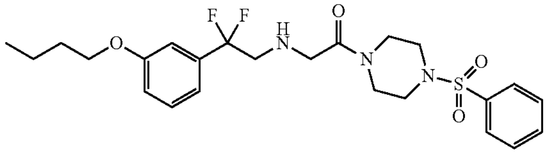 [SMILES: CCCCOc1cccc(C(F)(F)CNCC(=O)N2CCN(S(=O)(=O)c3ccccc3)CC2)c1]

Formula: $C_{24}H_{31}F_2N_3O_4S$

MW: 495.59

Mass/charge ratio: 496.24 ($MH^+$, ESI pos, 3.2KV, 25V, 400° C.).

Example 1-40

2-[2,2-Difluoro-2-(3-butoxyphenyl)-ethylamino]-1-(indolin-1-yl)-ethanone, hydrochloride

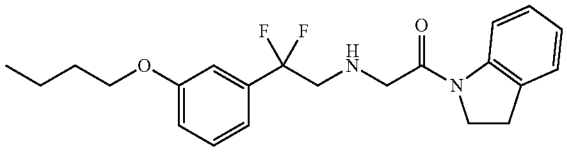 [SMILES: CCCCOc1cccc(C(F)(F)CNCC(=O)N2CCc3ccccc32)c1]

Formula: $C_{22}H_{26}F_2N_2O_2$

MW: 388.46

Mass/charge ratio: 389.25 ($MH^+$, ESI pos, 3.2KV, 25V, 350° C.).

Example 1-41

2-[2,2-Difluoro-2-(3-butoxyphenyl)-ethylamino]-1-(4-benzylpiperazin-1-yl)-ethanone, dihydrochloride

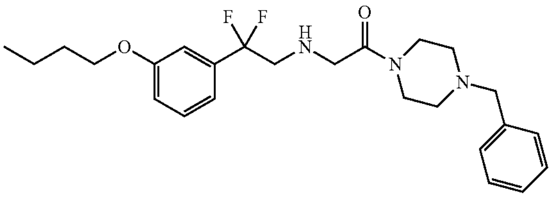 [SMILES: CCCCOc1cccc(C(F)(F)CNCC(=O)N2CCN(Cc3ccccc3)CC2)c1]

Formula: $C_{25}H_{33}F_2N_3O_2$

MW: 445.56

Mass/charge ratio: 446.34 ($MH^+$, ESI pos, 3.2KV, 25V, 400° C.).

Example 1-42

2-[2,2-Difluoro-2-(3-butoxyphenyl)-ethylamino)-1-(azetidin-1-yl)-ethanone, hydrochloride

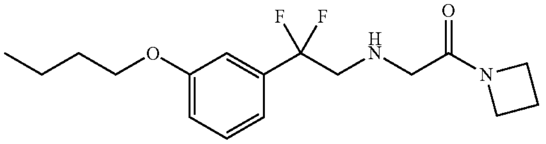 [SMILES: CCCCOc1cccc(C(F)(F)CNCC(=O)N2CCC2)c1]

Formula: $C_{17}H_{24}F_2N_2O_2$

MW: 326.39

Mass/charge ratio: 327.13 ($MH^+$, ESI pos, 3.2KV, 25V, 400° C.).

$^1$H-NMR (300 MHz, DMSO-d6) δ ppm 7.31-7.46 (m, 1H), 6.95-7.13 (m, 3H), 4.01 (t, 4H), 3.84 (t, 2H), 3.14-3.24 (m, 2H), 3.104 (dq, 2H), 2.18 (dt, 2H), 1.63-1.79 (m, 2H), 1.45 (dq, 2H), 0.94 (t, 3H).

Example 2-1

2-[2,2-Difluoro-2-(3-butoxyphenyl)-ethylamino]-N,N-dimethyl-propanamide, hydrochloride

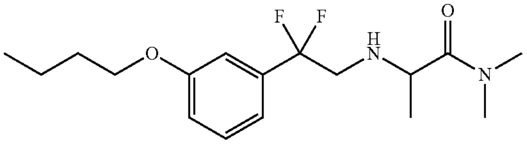 [SMILES: CCCCOc1cccc(C(F)(F)CNC(C)C(=O)N(C)C)c1]

Formula: $C_{17}H_{26}F_2N_2O_2$

MW: 328.41

Mass/charge ratio: 329.02 (MH+, ESI pos, 3.2KV, 25V, 350° C.)

$^1$H-NMR (300 MHz, DMSO-d6) δ ppm 9.48 (bs, 1H), 7.47 (t, 1H), 7.04-7.24 (m, 3H), 4.24-4.51 (m, 1H), 4.03 (t, 2H), 3.71-3.95 (m, 1H), 3.51-3.71 (m, 1H), 2.98 (s, 3H), 2.89 (s, 3H), 1.62-1.82 (m, 2H), 1.42 (d, 3H), 1.34-1.54 (m, 2H), 0.95 (t, 3H).

The above compound was synthesized according to Scheme 2

Scheme 2

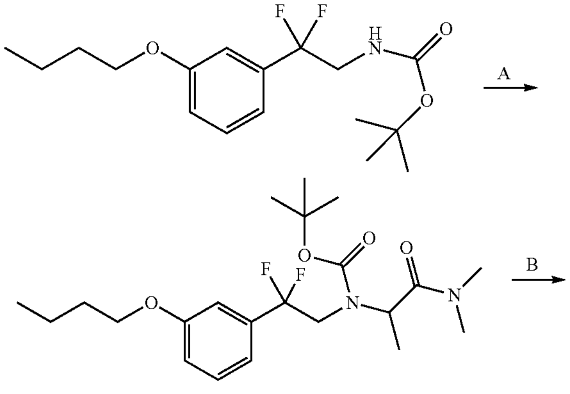

-continued

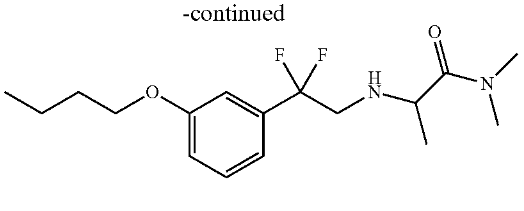

Step A 75 mg (0.23 mmol) of N-tert-butoxycarbonyl-2,2-difluoro-2-(3-butoxyphenyl)-ethylamine are dissolved in dry DMF (5 mL). The solution is cooled to 0° C. and NaH (6.7 mg; 1.2 eq) is added. The solution is stirred at RT for 10 min, then cooled again to 0° C. and 2-chloro-N,N-dimethylpropanamide (31 mg; 0.23 mmol) are added. After 4 hours a further 1.2 eq of NaH (6.7 mg) are added. The reaction mixture is stirred overnight at RT, then quenched with water, evaporated, the residue taken up with water and EtAc. The organic layer is separated and the water layer extracted three times with EtAc. The combined organic phases are dried over anhydrous $Na_2SO_4$, filtered and evaporated. The resulting crude residue is flash-chromatographed (eluant: petroleum ether/EtAc, 9/1 to 8/2). 2-[N-tert-butoxycarbonyl-2,2-difluoro-2-(3-butoxyphenyl)-ethylamino]-N,N-dimethylpropanamide (84 mg; 81%) is obtained as pale yellow oil.

Step B 84 mg (0.196 mmol) of 2-[N-tert-butoxycarbonyl-2,2-difluoro-2-(3-butoxyphenyl)-ethylamino]-N,N-dimethylpropanamide are dissolved in 3 mL of DCM and 0.49 mL (1.96 mmmol; 10 eq) of a 4M HCl solution in dioxane are added. After 8 hours, further 10 eq (0.49 mL) of 4M HCl 1 dioxane are added and the mixture is stirred overnight. Further 5 eq (0.245 mL) of 4M HCl in dioxane are the added and the mixture stirred for further 24 hours. The solution is evaporated, the white residue suspended in diethyl ether and then evaporated twice. The residue is flash-chromatographed on silica gel (DCM/MeOH 1/1 as an eluant followed by MeOH/conc. NH3 95/5). and the free base 2-[2,2-difluoro-2-(3-butoxyphenyl)-ethylamino]-N,N-dimethylpropanamide is isolated as a pale yellow fluid. The compound is dissolved in DCM (3 mL) and 4M HCl in dioxane is added to bring the solution to pH 2. The mixture is stirred for 10 minutes and then evaporated. The white residue is taken up with ether and evaporated twice. 45 mg (49%) of 2-[2,2-difluoro-2-(3-butoxyphenyl)-ethylamino]-N,N-dimethylpropanamide, hydrochloride (Example 2-1) are obtained.

Examples 2-2 to 2-5

These compounds are prepared according to the procedure described in Scheme 2.

Example 2-2

2-[2,2-Difluoro-2-(3-butoxyphenyl)-ethylamino]-3-methoxy-N,N-dimethyl-propanamide

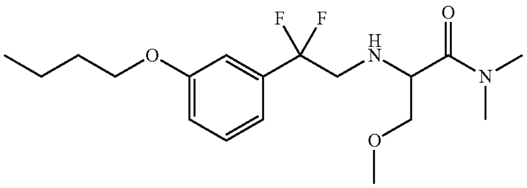 [SMILES: CCCCOc1cccc(C(F)(F)CNC(COC)C(=O)N(C)C)c1]

Formula: $C_{18}H_{28}F_2N_2O_3$

MW: 358.43

Mass/charge ratio: 359.40 ($MH^+$, ESI pos, 3.2KV, 15V, 400° C.).

$^1$H-NMR (300 MHz, DMSO-d6) δ ppm 7.39-7.59 (m, 1H), 7.06-7.21 (m, 3H), 4.64 (t, 1H), 4.03 (t, 2H), 3.58-3.87 (m, 4H), 3.30 (s, 3H), 3.02 (s, 3H), 2.91 (s, 3H), 1.59-1.81 (m, 2H), 1.36-1.57 (m, 2H), 0.94 (t, 3H).

Example 2-3

2-[2,2-Difluoro-2-(3-butoxyphenyl)-ethylamino]-3-(4-methoxyphenyl)-N,N-dimethyl-propanamide, hydrochloride

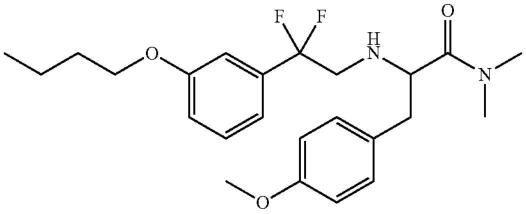 [SMILES: CCCCOc1cccc(C(F)(F)CNC(Cc2ccc(OC)cc2)C(=O)N(C)C)c1]

Formula: $C_{24}H_{32}F_2N_2O_3$

MW: 434.53

Mass/charge ratio: 435.36 ($MH^+$, ESI pos, 3.2KV, 25V, 400° C.).

Example 2-4

2-[2,2-Difluoro-2-(3-butoxyphenyl)-ethylamino]-2-N,N-trimethyl-propanamide, hydrochloride

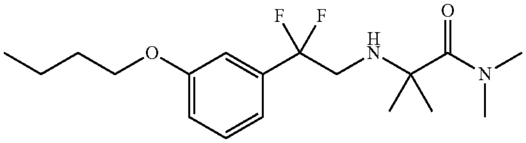 [SMILES: CCCCOc1cccc(C(F)(F)CNC(C)(C)C(=O)N(C)C)c1]

Formula: $C_{18}H_{28}F_2N_2O_2$

MW: 342.43

Mass/charge ratio: 342.31 (MH+, ESI pos, 3.2KV, 25V, 350° C.).

Example 2-5

2-[2,2-Difluoro-2-(3-butoxyphenyl)-ethylamino]-4-N,N-trimethyl-pentanamide, hydrochloride

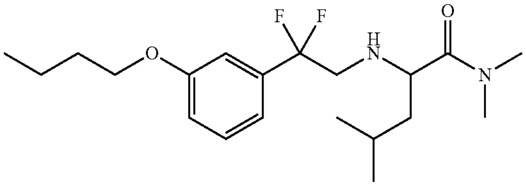 [SMILES: CCCCOc1cccc(C(F)(F)CNC(CC(C)C)C(=O)N(C)C)c1]

Formula: $C_{20}H_{32}F_2N_2O_2$

MW: 370.49

Mass/charge ratio: 371.33 (MH+, ESI pos, 3.2KV, 25V, 350° C.).

Example 3-1

2-{[2,2-Difluoro-2-(3-butoxyphenyl)-ethyl]-methyl-amino}-N,N-dimethyl-acetamide, hydrochloride

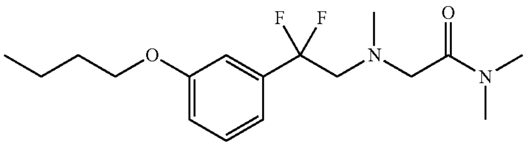 [SMILES: CCCCOc1cccc(C(F)(F)CN(C)CC(=O)N(C)C)c1]

Formula: $C_{17}H_{26}F_2N_2O_2$
MW: 328.41

Mass/charge ratio: 329.17 ($MH^+$, ESI pos, 3.2KV, 25V, 400° C.).

$^1$H-NMR (300 MHz, DMSO-d6) δ ppm 7.45 (t, 1H), 7.04-7.18 (m, 3H), 4.03 (t, 2H), 3.73-3.91 (m, 2H), 3.70-4.13 (m, 2H), 2.86 (s, 3H), 2.84 (s, 3H), 2.80 (s, 3H), 1.62-1.82 (m, 2H), 1.37-1.57 (m, 2H), 0.94 (t, 3H).

The above compound is synthesized according to Scheme 3

Scheme 3

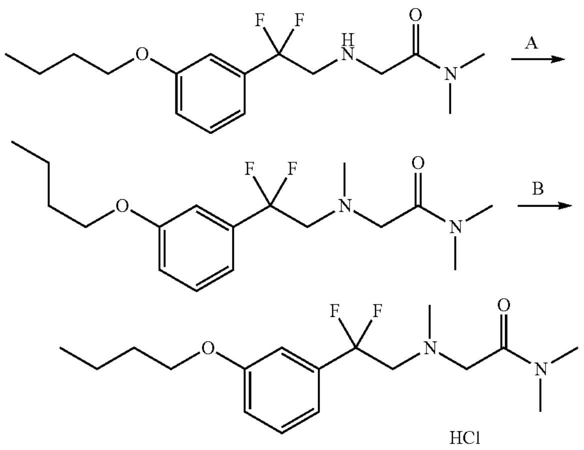

Examples 3-2 to 3-3

These compounds are prepared according to the procedure described in Scheme 3.

Step A 107.5 mg (0.34 mmol) of the free base of 2-[2,2-difluoro-2-(3-butoxyphenyl)-ethylamino]-N,N-dimethyl-acetamide (see Example 1-1) are dissolved in dry THF (10 mL). To this solution, formaldehyde (36.5% water solution, 52.1 μL; 0.69 mmol), acetic acid (2.5 mL), and MP-$CNBH_3$ (2.3 mmol/g; 325 mg; 0.75 mmol) are added sequentially. After stirring 1 hour the reaction is completed. After further stirring for 1.5 hours, the reaction mixture is evaporated. The crude residue is flash-chromatographed on silica gel using DCM/MeOH (99.5/0.5) as an eluant. 73.1 mg (65%) of pale yellow fluid 2-{[2,2-difluoro-2-(3-butoxyphenyl)-ethyl]-methylamino}-N,N-dimethyl-acetamide are obtained.

Step B

A solution of 73.1 mg of 2-{[2,2-difluoro-2-(3-butoxyphenyl)-ethyl]-methylamino}-N,N-dimethyl-acetamide in DCM (3 mL) is stirred and few drops of 4M HCl in dioxane are added until reaching pH 2. The reaction mixture is stirred for 5 minutes and then evaporated. The white solid residue is suspended in $Et_2O$ and evaporated twice to yield 77.4 mg (96%) of white solid 2-{[2,2-difluoro-2-(3-butoxyphenyl)-ethyl]-methylamino}-N,N-dimethyl-acetamide, hydrochloride (Example 3-1).

Example 3-2

2-{[2,2-Difluoro-2-(3-butoxyphenyl)-ethyl]-(3-methoxypropyl)-amino}-N,N-dimethyl-acetamide, hydrochloride

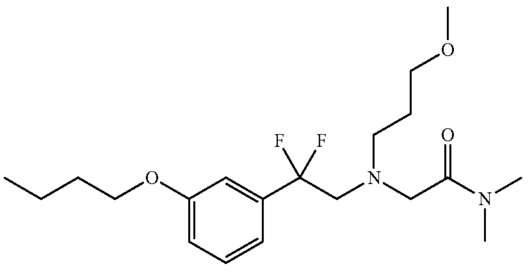 [SMILES: CCCCOc1cccc(C(F)(F)CN(CCCOC)CC(=O)N(C)C)c1]

Formula: $C_{20}H_{32}F_2N_2O_3$
MW: 386.49

Mass/charge ratio: 387.28 ($MH^+$, ESI pos, 3.2KV, 25V, 400° C.).

$^1$H-NMR (300 MHz, DMSO-d6+TFA) δ ppm 7.38-7.50 (m, 1H), 7.08-7.17 (m, 3H), 3.98-4.11 (m, 4H), 3.85 (t, 2H), 3.33 (t, 2H), 3.21 (s, 3H), 3.12-3.20 (m, 2H), 2.88 (s, 3H), 2.86 (s, 3H), 1.78-1.91 (m, 2H), 1.65-1.78 (m, 2H), 1.36-1.54 (m, 2H), 0.94 (t, 3H).

Example 3-3

2-{[2,2-Difluoro-2-(3-butoxyphenyl)-ethyl]-(2-methoxyethyl)-amino}-N,N-dimethyl-acetamide, hydrochloride

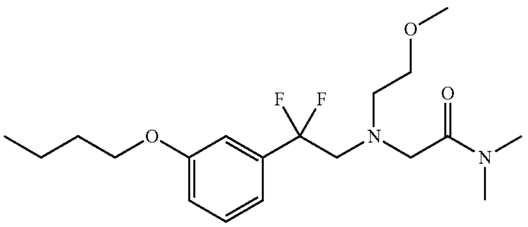 [SMILES: CCCCOc1cccc(C(F)(F)CN(CCOC)CC(=O)N(C)C)c1]

Formula: $C_{19}H_{30}F_2N_2O_3$
MW: 372.46

Mass/charge ratio: 373.30 ($MH^+$, ESI pos, 3.2KV, 25V, 400° C.).

$^1$H-NMR (300 MHz, DMSO-d6+TFA) δ ppm 7.38 (t, 1H), 6.95-7.11 (m, 3H), 4.01 (t, 2H), 3.50 (s, 2H), 3.42 (t, 2H), 3.28 (t, 2H), 2.85 (s, 3H), 2.79 (s, 3H), 2.76 (s, 3H), 1.63-1.79 (m, 2H), 1.35-1.52 (m, 2H), 0.94 (t, 3H).

Example 4-1

2-[2-Fluoro-2-(3-butoxyphenyl)-ethylamino]-N,N-dimethyl-acetamide, hydrochloride

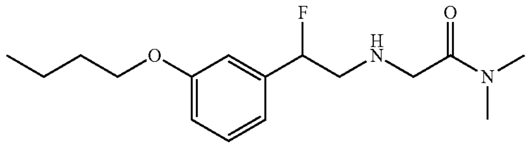 [SMILES: CCCCOc1cccc(C(F)CNCC(=O)N(C)C)c1]

Formula: $C_{16}H_{25}FN_2O_2$

MW: 296.39

Mass/charge ratio: 297.04 (MH+, ESI pos, 3.2KV, 25V, 350° C.)

$^1$H-NMR (300 MHz, DMSO-d6) δ ppm 9.35 (bs, 2H), 7.22-7.487 (m, 1H), 6.83-7.07 (m, 3H), 5.97 (ddd, 1H), 4.10 (s, 2H), 4.004 (t, 2H), 3.55 (td, 1H), 3.33-3.47 (m, 1H), 2.95 (s, 3H), 2.91 (s, 3H), 1.56-1.78 (m, 2H), 1.29-1.54 (m, 2H), 0.94 (t, 3H).

The above compound is synthesized according to Scheme 4

Scheme 4

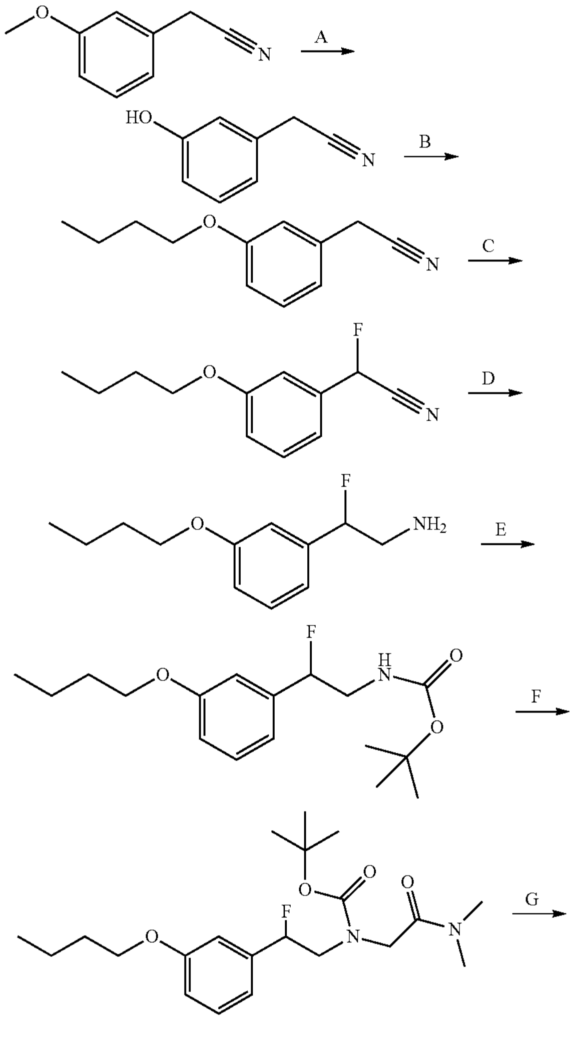

-continued

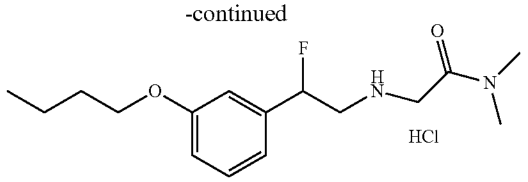

Step A

To a solution of 2-(3-methoxyphenyl)acetonitrile (2 g; 13.59 mmol) in 13 mL of dry dichloromethane (DCM) cooled at 0° C. under an inert atmosphere, a 1M solution of $BBr_3$ in DCM (28.54 mmol; 28.54 mL) is slowly added dropwise. The mixture is stirred at room temperature for 20 hours. The reaction mixture is then poured into ice, water is added and the organic phase is extracted three times with dichloromethane, washed with brine and dried over anhydrous $Na_2SO_4$. After evaporation, the crude mixture is purified by flash-chromatography on silica gel using petroleum ether/EtAc (80/20) as an eluant, affording 1.28 g (71%) of 2-(3-hydroxyphenyl)acetonitrile.

Step B

To a solution of 2-(3-hydroxyphenyl)acetonitrile (2.29 g; 17.11 mmol) in dry DMF (25 mL), $K_2CO_3$ (7.08 g; 51.33 mmol), KI (0.61 g; 3.70 mmol) and 1-bromobutane (4.69 g; 3.69 mL; 34.22 mmol) are added and the mixture is stirred at 60° C. for 5 hours and then at room temperature overnight. A TLC (DCM/EtAc 95/5) shows no presence of starting material. After evaporation, the reaction mixture is extracted with ethyl acetate (150 mL) and washed with brine (150 mL twice): the aqueous phase is acidified with 0.1N HCl and extracted again with ethyl acetate. The combined organic layers are dried over anhydrous $Na_2SO_4$, filtered and evaporated. The crude mixture is purified by flash-chromatography (eluant: petroleum ether/ethyl acetate 99/1) yielding, after evaporation, 3.07 g (95%) of 2-(3-butoxyphenyl)acetonitrile as a pale yellow oil.

Step C

Tert-butyllithium (1268 uL; 2.16 mmol) is added dropwise to a solution of 2-(3-butoxyphenyl)acetonitrile (371 mg; 1.96 mmol) in THF (16 mL) at −78° C., under nitrogen atmosphere. The light yellow solution turned into orange and stirring is continued for 1 hour. A solution of N-fluorobenzenesulfonimide (618 mg; 1.96 mmol) in THF (2 mL) is added dropwise and the reaction is stirred at −78° C. for 2 hours. TLC (petroleum ether/EtAc 9:1) reveals no presence of starting material and two more apolar spots. The reaction is then quenched by adding 0.01N HCl, then more water is added and extracted with DCM (three times). The combined organic layers are dried over $Na_2SO_4$, filtered and evaporated. The crude residue is purified by flash chromatography (petroleum ether/EtAc, 99/1) affording 217 mg (53%) of 2-(3-butoxyphenyl)-2-fluoroacetonitrile as a colorless oil.

Step D

To a solution of 2-(3-butoxyphenyl)-2-fluoroacetonitrile (109 mg: 0.53 mmol) in dry THF (5 mL), borane tetrahydrofurane complex (2.10 mL; 2.10 mmol) is added and the reaction is stirred at 0° C. for 2 hours and then at RT for 6 hours. An LC/MS shows almost complete conversion. The reaction is quenched adding slowly few drops of EtOH and few drops of conc. HCl/EtOH (1:5) and stirring is continued for 5 min. DCM was then added, followed by 5% aqueous $NaHCO_3$. The two phases are separated and the aqueous phase is extracted twice with DCM. The combined organic layers are dried over $Na_2SO_4$, filtered and evaporated. The crude residue is purified using a SCX cartridge (eluant: DCM/MeOH 1/1 to MeOH/conc. aq. $NH_3$ 95/5) affording 2-(3-butoxyphenyl)-2-fluoroethanamine (92 mg; 0.43 mmol; 83%) as a pale yellow oil.

Step E

DIPEA (0.106 mL; 0.61 mmol) is added to a solution of 2-(3-butoxyphenyl)-2-fluoroethanamine (92 mg; 0.43 mmol) and $Boc_2O$ (0.121 mL; 0.52 mmol) in dry THF (6 mL) and the reaction is stirred at RT for 2 hours. An LC/MS shows complete conversion. DCM is added and the solution is washed with 5% aq. $NaHCO_3$ and 1N HCl, dried over anhydrous $Na_2SO_4$, filtered and evaporated to give tert-butyl 2-(3-butoxyphenyl)-2-fluoroethylcarbamate (136 mg; 0.437 mmol; 100%) as a pale yellow oil.

Step F

A solution of tert-butyl 2-(3-butoxyphenyl)-2-fluoroethylcarbamate (136 mg; 0.44 mmol) in dry DMF (4 mL) under nitrogen atmosphere is cooled to 0° C. and sodium hydride (22.7 mg; 0.57 mmol) is added. The mixture is stirred at RT for 10 min, then is cooled again to 0° C. and 2-chloro-N,N-dimethyl-acetamide (0.054 mL; 0.524 mmol) is added. The reaction mixture is stirred at RT for 4 hours. An LC/MS shows very low conversion. Additional sodium hydride (38 mg; 0.96 mmol) is added followed after 10 min by 2-chloro-N,N-dimethyl-acetamide (0.09 mL; 0.87 mmol). Stirring is continued for 12 hours. An LC/MS shows almost complete conversion. The solvent is evaporated, EtAc is added and the solution is washed with brine, then dried over anhydrous $Na_2SO_4$, filtered and evaporated. The crude residue is purified by flash-chromatography (DCM/EtAc from 96/4 to 95/5) yielding tert-butyl N-[2-(3-butoxyphenyl)-2-fluoroethyl]-N-[(2-dimethylamino)-2-oxoethyl)]-carbamate (100 mg; 0.25 mmol; 58%) as a colourless oil.

Step G

A mixture of tert-butyl N-[2-(3-butoxyphenyl)-2-fluoroethyl]-N-[(2-dimethylamino)-2-oxoethyl)]-carbamate (96 mg; 0.24 mmol) and 4M HCl in dioxane (363 uL; 1.45 mmol) in dry DCM (6 mL) is stirred at RT for 4 hours. An LC/MS show complete conversion. The solvent is evaporated affording 2-[2-(3-butoxyphenyl)-2-fluoroethylamino)]-N,N-dimethyl-acetamide (50 mg; 0.17 mmol; 70%) as a pale yellow amorphous solid which is triturated with EtAc, filtered and dried to give 22.2 mg (0.067 mmol; 44%) of white solid 2-[2-(3-butoxyphenyl)-2-fluoroethylamino]-N,N-dimethyl-acetamide, hydrochloride.

Example 4-1

Examples 4-2 to 4-3

These compounds were prepared according to the procedure described in Scheme 4.

Example 4-2

2-{2-Fluoro-2-[3-(3-chlorobenzyloxy)-phenyl]-ethylamino}-N,N-dimethyl-acetamide, hydrochloride Example 4-3

2-{2-Fluoro-2-[3-(3-fluorobenzyloxy)-phenyl]-ethylamino}-N,N-dimethyl-acetamide, hydrochloride Example 5

N-Type Calcium Channel Influx Assay

IMR32 human neuroblastoma cells constitutively express both L- and N-type channels. Under differentiating conditions, IMR32 cells preferentially express on the membrane surface N-type calcium channels. The remaining L-type calcium channels are blocked using the selective L-type blocker nifedipine. In these experimental conditions only N-type channels can be detected.

IMR32 cells are differentiated using 1 mM dibutyryl-cAMP and 2.5 μM bromodeoxyuridine for 8 days (4 times) in 225 $cm^2$ flask, then detached, seeded at 200,000 cells/well on 96 poly-L-lysine-coated plates and further incubated for 18-24 h in the presence of differentiating buffer before use.

The $Ca^{2+}$ Kit Assay (Molecular Devices, CA—USA), based on a fluorescent calcium indicator and able to detect the calcium influx determined by depolarizing conditions, is used for the assay.

Differentiated cells are incubated with dye loading for 30 minutes at 37° C. then, nifedipine alone (1 μM) or in the presence of ω-conotoxin (as reference standard) or test compounds are added for further 15 minutes.

The fluorescence (excitation: 485 nm, emission: 535 nm wavelength) is measured before and after (30-40 s) the automated injection of 100 mM KCl depolarizing solution using a Victor plate reader (Perkin Elmer, MA—USA).

The inhibition curves are calculated from 5 concentrations, each in triplicate, and the $IC_{50}$ determined using a linear regression analysis.

The compounds of the present invention inhibit N-type calcium channels with pharmacologically significant $IC_{50}$ values.

Example 6

TTXs-Sodium Channel Influx Assay

ND7/23 rat dorsal root ganglion-derived cell line endogenously expresses a mixed population of TTXs sodium channels (such as Nav1.3, Nav1.2, Nav1.1, Nav1.6). These cells lack of TTXr sodium channels as shown by the absence of their respective transcripts. ND7/23 cells are grown in Dulbecco's Modified Eagle Medium (DMEM, Invitrogen, CA—USA) supplemented with 10% Foetal Bovine Serum (FBS, Invitrogen, CA—USA) and 1 mM sodium piruvate. The cells are seeded at 50,000 cells/well on 96 poly-L-lysine-coated plates and further incubated for 18-24 h before use.

The Membrane Potential Kit Assay (Molecular Devices, CA—USA), based on a negatively charged fluorescent dye able to monitor changes in membrane potential caused by the sodium influx due to the channel opening, is used for the assay.

Cells are incubated with the dye loading for 30 minutes at 25° C. Then, 100 nM of the toxin *Anemonia sulcata* (used as enhancer of the channel opener response) alone or in the presence of TTX (as reference standard) or test compound are added for further 15 minutes.

The fluorescence (excitation: 530 nm, emission: 565 nm wavelength) is measured before and after (40-45 s) the automated injection of the sodium channel opener veratridine (100 μM) using a Victor plate reader (Perkin Elmer, MA—USA).

The inhibition curves are calculated from 5 concentrations, each in triplicate, and the $IC_{50}$ determined using a linear regression analysis.

The compounds of the present invention inhibit TTXs sodium channels with pharmacologically significant $IC_{50}$ values.

The results, obtained with some compounds which are representative of the entire class of compounds of the invention are reported in Table 1.

TABLE 1

| COMPOUND | $IC_{50}$ [μM] |
|---|---|
| 2-[2,2-Difluoro-2-(3-butoxyphenyl)-ethylamino]-N,N-dimethyl-acetamide, hydrochloride (Example 1-1) | 1.0 |
| 2-[2,2-Difluoro-2-(3-pentyloxyphenyl)-ethylamino]-N,N-dimethyl-acetamide, hydrochloride (Example 1-2) | 1.3 |
| 2-[2,2-Difluoro-2-(3-butoxyphenyl)-ethylamino]-N,N-dipropyl-acetamide, hydrochloride (Example 1-3) | 0.58 |
| 2-[2,2-Difluoro-2-(3-hexyloxyphenyl)-ethylamino]-N,N-dimethyl-acetamide, hydrochloride (Example 1-6) | 0.14 |
| 2-{2,2-Difluoro-2-[3-(4,4,4-trifluorobutoxy)-phenyl]-ethylamino}-N,N-dimethyl-acetamide, hydrochloride (Example 1-7) | 3.6 |
| 2-[2,2-Difluoro-2-(3-benzyloxyphenyl)-ethylamino]-N,N-dimethyl-acetamide, hydrochloride (Example 1-14) | 1.2 |
| 2-[2,2-Difluoro-2-(3-butoxyphenyl)-ethylamino]-1-(pyrrolidin-1-yl)-ethanone, hydrochloride (Example 1-15) | 1.1 |
| 2-{2,2-Difluoro-2-[3-(4,4,4-trifluorobutoxy)-phenyl]-ethylamino}-1-(pyrrolidin-1-yl)-ethanone (Example 1-18) | 0.95 |
| 2-{2,2-Difluoro-2-[3-(4,4,4-trifluorobutoxy)-phenyl]-ethylamino}-1-(morpholin-4-yl)-ethanone, hydrochloride (Example 1-21) | 7.2 |
| 2-[2,2-Difluoro-2-(3-butoxyphenyl)-ethylamino]-1-(4-methylpiperazin-1-yl)-ethanone, hydrochloride (Example 1-26) | 23.2 |
| 2-{2,2-Difluoro-2-[3-(4,4,4-trifluorobutoxy)-phenyl]-ethylamino}-1-(4-methylpiperazin-1-yl)-ethanone, hydrochloride (Example 1-28) | 3.2 |
| 2-[2,2-Difluoro-2-(3-butoxyphenyl)-ethylamino]-1-(piperidin-1-yl)-ethanone, hydrochloride (Example 1-29) | 1.8 |
| 2-[2,2-Difluoro-2-(3-butoxyphenyl)-ethylamino]-N,N-diethyl-acetamide, hydrochloride (Example 1-32) | 2.8 |
| 2-[2,2-Difluoro-2-(3-butoxyphenyl)-ethylamino]-1-(azetidin-1-yl)-ethanone, hydrochloride (Example 1-42) | 5.0 |
| 2-[2,2-Difluoro-2-(3-butoxyphenyl)-ethylamino]-N,N-dimethyl-propanamide, hydrochloride (Example 2-1) | 20.0 |
| 2-[2,2-Difluoro-2-(3-butoxyphenyl)-ethylamino]-3-methoxy-N,N-dimethyl-propanamide (Example 2-2) | 6.2 |
| 2-{[2,2-Difluoro-2-(3-butoxyphenyl)-ethyl]-methylamino}-N,N-dimethyl-acetamide, hydrochloride (Example 3-1) | 2.3 |
| 2-{[2,2-Difluoro-2-(3-butoxyphenyl)-ethyl]-(3-methoxypropyl)-amino}-N,N-dimethyl-acetamide, hydrochloride (Example 3-2) | 2.4 |
| 2-{[2,2-Difluoro-2-(3-butoxyphenyl)-ethyl]-(2-methoxyethyl)-amino}-N,N-dimethyl-acetamide, hydrochloride (Example 3-3) | 1.4 |
| 2-[2-Fluoro-2-(3-butoxyphenyl)-ethylamino]-N,N-dimethyl-acetamide, hydrochloride (Example 4-1) | 1.5 |

Example 7

Patch Clamp Studies of Calcium Currents Inhibition

Cells and Methods:

Functional inhibition of the N-type Ca currents is studied using whole cell patch clamp methods (Hamill O. P., Marty A., Neher E., Sakmann B., Sigworth F. J. Pflugers Arch. 391: 85-100 (1981)) on HEK293 cells expressing recombinant human N-type channels, obtained after transient transfection of h α1B (hCav2.2)+β1b+α2δ-1 subunits.

Membrane currents are recorded and filtered at 5 kHz with an Axon Axopatch 200B amplifier and digitized with an Axon Digidata 1322A (Axon Instruments, CA, USA). Voltage clamping of membrane potentials and data acquisition are controlled online with Axon pClamp8 software. Measuring and reference electrodes are AgCl—Ag electrodes. Cells have initial seal resistances of >1 GΩ and access resistances of 4.2±0.2 MΩ. Cells are continuously superfused with extracellular solutions using a Biologic RSC-200 (Biologic SAS, France).

For calcium currents recording the control bath solution contained (mM): choline chloride (70), $MgCl_2$ (1), $BaCl_2$ (20), TEA.Cl (50), Hepes (10), glucose (10). Internal pipette solution consists of (mM): CsCl (140), EGTA (10), $MgCl_2$ (2), Hepes (10), MgATP (1), GTP Tris (0.3).

Compounds are dissolved as 20 mM stock solutions in DMSO and then diluted to the final concentration in the external solutions.

Voltage Protocols and Data Analyses:

A two-step protocol is used to determine the voltage dependence of the block:

N-type current is activated by a 600 ms step pulse to +10 mV (test pulse) from a 5000 ms preconditioning potential of −110 mV (resting condition) or −50/−55 mV (half maximal steady-state inactivated condition), respectively.

The amplitude of calcium current peaks evoked by the respective test pulses at a frequency of 0.06 Hz are measured before and after exposure to the test substance. Tonic block of currents is calculated as the difference between the peak calcium current measured at the end of a stabilization period in the control external bath solution and peak currents measured at the end of test substance perfusion period (when steady state is reached) divided by control peaks. Drug concentration-inhibition curves are obtained by plotting tonic blocks versus drug concentrations. Dose-response curves are fitted to the tonic block data, according to the logistic equation: $y=A2+(A1-A2)/[1+(x/IC_{50})^p]$. A1 and A2 are fixed values of 0 and 1 corresponding to 0 and 100% current inhibition, x is the drug concentration, $IC_{50}$ is the drug concentration resulting in 50% current inhibition and p is the corresponding slope factor.

The compounds of the present invention inhibit N-type calcium channels with pharmacologically significant $IC_{50}$ values.

Example 8

Patch Clamp Studies of Sodium Currents Inhibition

Cells and methods: Functional inhibition of the sodium currents is studied using whole cell patch clamp methods (Hamill O. P., Marty A., Neher E., Sakmann B., Sigworth F. J., Pflugers Arch. 391 (2): 85-100 (1981)) on the hybrid cell line ND7/23 (Wood J N, Bevan S J, Coote P R, Dunn P M, Harmar A, Hogan P, Latchman D S, Morrison C, Rougon G, Theveniau M.: "Novel cell lines display properties of nociceptive sensory neurons". Proc. Biol. Sci. Sep 22; 241 (1302):187-94 (1990)), that express a mixed population of voltage gated sodium channels.

Membrane currents are recorded as described in the example above.

For sodium current recording control bath solution contained (mM): NaCl (80), choline chloride (38), $CaCl_2$ (1.3), $MgCl_2$ (2), KCl (2), $CdCl_2$ (0.4), $NiCl_2$ (0.3), TEA.Cl (20), Hepes (10), glucose (10). Internal pipette solution consists of (mM): CsF (65), CsCl (65), NaCl (10), $CaCl_2$ (1.3), $MgCl_2$ (2), Hepes (10), EGTA (10), MgATP (1).

Compounds are dissolved as 20 mM stock solutions in DMSO and then diluted to the final concentration in the external solutions.

Voltage protocols and data analyses: A two-step protocol is used to determine the voltage dependence of the block: sodium current is activated by a 30 ms step pulse to 0 mV (test pulse) from a 2000 ms preconditioning potential of −100 mV (resting condition) or −70 mV (half maximal steady-state inactivated condition), respectively.

Drug concentration-inhibition curves are obtained by plotting tonic blocks in the resting and depolarized condition, versus drug concentrations. Dose-response curves are fitted to the tonic block data, according to the logistic equation: $y=A2+(A1-A2)/[1+(x/IC_{50})_p]$. A1 and A2 are fixed values of 0 and 1 corresponding to 0 and 100% current inhibition, x is the drug concentration, $IC_{50}$ is the drug concentration resulting in 50% current inhibition and p is the corresponding slope factor.

Besides the voltage dependent block calculated as $IC_{50}$ s from the resting and the depolarized membrane potential, respectively, a better evaluation of the apparent affinity of drug for the inactivated state is done by calculating the Ki according to the equation 1/Kdep=h/Kr+(1−h)/Ki where Kr is the affinity of drug for the resting/closed state; Kdep is the $IC_{50}$ in the depolarized condition, h and (1−h) are the fractions of channels present at the rest and dep potentials, respectively (De Luca et al. "Optimal requirements for high affinity and use-dependent block of skeletal muscle sodium channel by N-benzyl analogs of tocamidelike compounds". Mol Pharmacol 64:932-945. (2003)). In fact although the $IC_{50}$ value at resting (condition of maximal availability current=Imax) can be considered as the affinity constant for closed/resting (Kr) channels, the $IC_{50}$ from depolarized potential (the specific Vhalf was used as preconditioning depolarized potential) is influenced by the relative proportion of resting channels in equilibrium with inactivated ones and by the ability of the drug to influence such an equilibrium based on its affinity for inactivated state.

Ki represents a better estimation of the inactivated-state block, cleaned from the closed/resting state block.

The results, obtained with compounds which are representative of the entire class of compounds of the invention are reported in Table 2.

TABLE 2

| COMPOUND | $K_i$ [μM] |
|---|---|
| 2-[2,2-Difluoro-2-(3-butoxyphenyl)-ethylamino]-N,N-dimethyl-acetamide, hydrochloride (Example 1-1) | 0.1 |
| 2-[2,2-Difluoro-2-(3-hexyloxyphenyl)-ethylamino]-N,N-dimethyl-acetamide, hydrochloride (Example 1-6) | 0.1 |
| 2-{2,2-Difluoro-2-[3-(4,4,4-trifluorobutoxy)-phenyl]-ethylamino}-N,N-dimethyl-acetamide, hydrochloride (Example 1-7) | 0.1 |
| 2-[2,2-Difluoro-2-(3-benzyloxyphenyl)-ethylamino]-N,N-dimethyl-acetamide, hydrochloride (Example 1-14) | 0.5 |
| 2-[2,2-Difluoro-2-(3-butoxyphenyl)-ethylamino]-1-(pyrrolidin-1-yl)-ethanone, hydrochloride (Example 1-15) | 0.2 |
| 2-{2,2-Difluoro-2-[3-(4,4,4-trifluorobutoxy)-phenyl]-ethylamino}-1-(pyrrolidin-1-yl)-ethanone (Example 1-18) | 0.2 |
| 2-[2,2-Difluoro-2-(3-butoxyphenyl)-ethylamino]-1-(piperidin-1-yl)-ethanone, hydrochloride (Example 1-29) | 0.7 |
| 2-[2,2-Difluoro-2-(3-butoxyphenyl)-ethylamino]-N,N-diethyl-acetamide, hydrochloride (Example 1-32) | 0.3 |
| 2-{[2,2-Difluoro-2-(3-butoxyphenyl)-ethyl]-(2-methoxyethyl)-amino}-N,N-dimethyl-acetamide, hydrochloride (Example 3-3) | 1.7 |
| 2-[2-Fluoro-2-(3-butoxyphenyl)-ethylamino]-N,N-dimethyl-acetamide, hydrochloride (Example 4-1) | 1.1 |

Data expressed as $K_i$ values at μM concentration demonstrate that the compounds of the invention are potent as inhibitors of sodium channels.

Example 9

Inhibition of Sodium Currents in Cortical Neurons

Cell Preparation and culturing: cortical neurons are prepared from embryonic Wistar rats (E17-E19). Brains of E17/E19 rats are removed and placed in ice-cold Hank's solution (Hank's solution (Invitrogen, CA—USA)+glucose 30%+Pen-Strep 100× (Invitrogen, CA—USA) 100 U-100 μg/ml and Hepes-NaOH 5 mM).

Cortex are isolated, cut in small parts and washed twice with Hank's solution. The solution is removed except 1-2 ml and the tissue is mechanically dissociated. After the mechanical dissociation, 5 ml of complete DMEM (Dulbecco's modified Eagle medium) (Invitrogen, CA—USA)+FBS (Invitrogen, CA—USA) 10%+Glutamine (Invitrogen, CA—USA) 2 mM+Pen-Strep 100 U-100 μg/ml are added, and cell suspension is centrifuged for 5 min at 1000 rpm. Supernatant is removed and 5 ml of complete Neurobasal (Invitrogen, CA—USA) medium is added+B27 supplement (code 17504044, Invitrogen, CA—USA) 2%+Glutamine 2 mM+Pen-Strep 100 U-100 μg/ml).

Cells are counted and diluted in Neurobasal medium to a concentration of 400000 cells per poly-D-lysine 5 μg/ml treated Petri dish.

Cortical neurons are used from day $6^{th}$ till day $11^{th}$ after plating, and once a week Neurobasal medium is changed.

Whole Cell Patch Clamp Recordings: Experiments on cortical neurons are carried out using standard whole cell patch clamp methods (Hamill O. P., Marty A., Neher E., Sakmann B., Sigworth F. J., Pflugers Arch. 391 (2): 85-100 (1981)). Membrane currents are recorded and filtered at 5 kHz with an Axon Axopatch 200B amplifier and data digitized with an Axon Digidata 1322A (Axon Instruments, CA, USA). Protocol playing and data acquisition are controlled online with Axon pClamp8 software. Measuring and reference electrodes are AgCl—Ag electrodes. A Sutter Instrument (Sutter Instrument, CA, USA) P-87 Puller is used for pulling patch clamp pipettes with a resistance of 2-3 MΩ from Harward borosilicate glass tubes. Cells are continuously superfused with extracellular solutions, using a solution changer Biologic RSC-200 (Bio-Logic Sas, France).

Solutions: Sodium current recording control bath solution contains (mM): NaCl (60), cholineCl (60), $CaCl_2$ (1.3), $MgCl_2$ (2), KCl (2), $CdCl_2$ (0.4), $NiCl_2$ (0.3), TEACl (20), Hepes (10), glucose (10). Internal pipette solution consists of (mM): CsF (65), CsCl (65), NaCl (10), $CaCl_2$ (1.3), $MgCl_2$ (2), Hepes (10), EGTA (10), MgATP (1).

Voltage protocols and data analyses: cells are clamped at −90 mV, then a two step protocol is used to determine the voltage dependence of the block. Sodium currents are activated by a 30 ms step pulse to −10 mV (test pulse) from a 2000 ms preconditioning potential of −110 mV (resting condition) and a potential of ~−50 mV (half maximal steady-state condition).

Drug concentration-inhibition curves are obtained by plotting tonic blocks in the resting and depolarized condition, versus drug concentrations. Dose-response curves are fitted to the tonic block data, according to the logistic equation: $y=A2+(A1-A2)/[1+(x/IC_{50})_p]$. A1 and A2 are fixed values of 0 and 1 corresponding to 0 and 100% current inhibition, x is the drug concentration, $IC_{50}$ is the drug concentration resulting in 50% current inhibition and p is the corresponding slope factor.

The compounds of the present invention inhibit sodium currents of cortical neurons with pharmacologically significant $IC_{50}$ values.

Example 10

Inhibition of Cytochrome P4502D6 (CYP2D6)

The inhibition of Cytochrome P4502D6 (CYP2D6) is assessed by performing in vitro inhibition studies using Supersomes, microsomes derived from baculovirus infected insect cells; the baculoviruses are engineered to express one or more drug metabolizing enzyme cDNAs. Supersomes catalyze the same enzymatic reactions as human liver microsome enzymes, but they contain much higher enzyme activity than other microsome sources (Crespi C. L. and Penman B. W., Advances Pharmacology, 43, 171-188 (1997); Crespi C. L. and Miller V. P., Analytical Biochemistry, 248, 188-190 (1997)).

Kits with Supersomes are Supplied by GENTEST (MA, USA).

Serial Dilution of Test Compound and Positive Control in a 96-Well Plate

Test compound is dissolved in DMSO 500× the highest final concentration desired in the $IC_{50}$ assay. 30 ml of deionized water is pre-warmed to 37° C. and all kit components are placed on ice. For each well of column 1, 149.4 µL of NADPH-Cofactor Mix, (187.5 µl of Cofactors, 150 µl of G6PDH, 100 µl of Control Protein and 14.56 ml of 37° C. water) are added.

In each well from Column 2 to 12, 100 µl of Cofactor/DMSO mix (40 µL DMSO in 9.96 ml of NADPH-Cofactor Mix) are added. To each well of column 1, 0.6 µl of test compound or positive control are added. 50 µl from each well of column 1 are serially diluted to column 8. The extra 50 µl from column 8 are discarded. The plate is covered and pre-incubated at 37° C. for 10 minutes.

Preparation of enzyme/substrate mix: 7.92 ml of pre-warmed deionized water, 75 µl of enzyme, 3 µl of 10 mM AMMC and 2 ml of pre-warmed buffer are mixed.

Reaction Initiation and Termination

After the pre-incubation time (10'), 100 µl of enzyme/substrate mix to each well from column 1 to 10 are added. The plate is incubated at 37° C. for 30 minutes. After this time, 75 µl of Stop Reagent to each well are added. For blank controls, 100 µl of enzyme/substrate mix are added to columns 11 and 12.

Reading the Results

Plates are read at the Victor plate reader (Perkin Elmer, MA—USA) at 390 nm excitation and 460 nm emission wavelengths.

The results, obtained with some compounds which are representative of the entire class of compounds of the invention are reported in Table 3, compared with the corresponding de-fluorinated reference standards of the closest prior art.

TABLE 3

| Fluorinated derivative | $IC_{50}$ [µM] | Corresponding de-fluorinated derivative | $IC_{50}$ [µM] |
|---|---|---|---|
| 2-[2,2-Difluoro-2-(3-butoxyphenyl)-ethylamino]-N,N-dimethyl-acetamide, hydrochloride (Example 1-1) | >40 | 2-[2-(3-Butoxyphenyl)-ethylamino]-N,N-dimethyl-acetamide, hydrochloride | 5.8 |
| 2-[2,2-Difluoro-2-(3-butoxyphenyl)-ethylamino]-1-(pyrrolidin-1-yl)-ethanone, hydrochloride (Example 1-15) | >40 | 2-[2-(3-Butoxyphenyl)-ethylamino]-1-(pyrrolidin-1-yl)-ethanone, hydrochloride | 3.0 |
| 2-[2-Fluoro-2-(3-butoxyphenyl)-ethylamino]-N,N-dimethyl-acetamide, hydrochloride (Example 4-1) | >40 | 2-[2-(3-Butoxyphenyl)-ethylamino]-N,N-dimethyl-acetamide, hydrochloride | 5.8 |
| 2-[2,2-Difluoro-2-(3-butoxyphenyl)-ethylamino]-N,N-diethyl-acetamide, hydrochloride (Example 1-32) | 34.0 | 2-[2-(3-Butoxyphenyl)-ethylamino]-N,N-diethyl-acetamide, hydrochloride | 2.5 |

TABLE 3-continued

| Fluorinated derivative | $IC_{50}$ [µM] | Corresponding de-fluorinated derivative | $IC_{50}$ [µM] |
|---|---|---|---|
| 2-[2,2-Difluoro-2-(3-butoxyphenyl)-ethylamino]-N,N-dipropyl-acetamide, hydrochloride (Example 1-3) | 23.9 | 2-[2-(3-Butoxyphenyl)-ethylamino]-N,N-dipropyl-acetamide, hydrochloride | 0.7 |
| 2-[2,2-Difluoro-2-(3-butoxyphenyl)-ethylamino]-1-(piperidin-1-yl)-ethanone, hydrochloride (Example 1-29) | 38.3 | 2-[2-(3-Butoxyphenyl)-ethylamino]-1-(piperidin-1-yl)-ethanone, hydrochloride | 1.1 |
| 2-{[2,2-Difluoro-2-(3-butoxyphenyl)-ethyl]-(3-methoxypropyl)-amino}-N,N-dimethyl-acetamide, hydrochloride (Example 3-2) | >40 | 2-{[2-(3-Butoxyphenyl)-ethyl]-(3-methoxypropyl)-amino}-N,N-dimethyl-acetamide, hydrochloride | 7.3 |
| 2-[2,2-Difluoro-2-(3-butoxyphenyl)-ethylamino]-N,N-dimethyl-propanamide, hydrochloride (Example 2-1) | >40 | 2-[2-(3-Butoxyphenyl)-ethylamino]-N,N-dimethyl-propanamide, hydrochloride | 5.8 |
| 2-[2,2-Difluoro-2-(3-pentyloxyphenyl)-ethylamino]-N,N-dimethyl-acetamide, hydrochloride (Example 1-2) | >40 | 2-[2-(3-Pentyloxyphenyl)-ethylamino]-N,N-dimethyl-acetamide, hydrochloride | 3.5 |
| 2-[2,2-Difluoro-2-(3-hexyloxyphenyl)-ethylamino]-N,N-dimethyl-acetamide, hydrochloride (Example 1-6) | 37.8 | 2-[2-(3-Hexyloxyphenyl)-ethylamino]-N,N-dimethyl-acetamide, hydrochloride | 0.9 |
| 2-{2,2-Difluoro-2-[3-(4,4,4-trifluorobutoxy)-phenyl]-ethylamino}-1-(pyrrolidin-1-yl)-ethanone (Example 1-18) | >40 | 2-{2-[3-(4,4,4-trifluorobutoxy)-phenyl]-ethylamino}-1-(pyrrolidin-1-yl)-ethanone, hydrochloride | 5.0 |
| 2-{2,2-Difluoro-2-[3-(4,4,4-trifluorobutoxy)-phenyl]-ethylamino}-1-(morpholin-4-yl)-ethanone, hydrochloride (Example 1-21) | >40 | 2-{2-[3-(4,4,4-trifluorobutoxy)phenyl]-ethylamino}-1-(morpholin-4-yl)-ethanone, hydrochloride | 1.8 |
| 2-[2,2-Difluoro-2-(3-benzyloxyphenyl)-ethylamino]-N,N-dimethyl-acetamide, hydrochloride (Example 1-14) | >40 | 2-[2-(3-Benzyloxyphenyl)-ethylamino]-N,N-dimethyl-acetamide, hydrochloride | 10.6 |
| 2-{[2,2-Difluoro-2-(3-butoxyphenyl)-ethyl]-(2-methoxyethyl)]-amino}-N,N-dimethyl-acetamide, hydrochloride (Example 3-3) | >40 | 2-{[2-(3-Butoxyphenyl)-ethyl]-(2-methoxyethyl)-amino}-N,N-dimethyl-acetamide, hydrochloride | 3.4 |

From the data presented in Table 3 it is apparent the difluoro-substituted derivatives always display inhibitory activity on CYP2D6 with $IC_{50}$ values above 20 µm and, in most cases, near or above 40 µM, whilst the corresponding unsubstituted analogs from the prior art are endowed with inhibitory activities, most often in the single digit micromolar range.

Example 11

Complete Freund's Adjuvant Model of Chronic Inflammatory Pain

Monoarthritis is induced in rats (200 g weight) by an intra-plantar injection into the left hind paw of 100 µl of complete Freund's adjuvant (CFA) containing heat-killed and dried *Mycobacterium tubercolosis* in a mixture of paraffin oil and an emulsifying agent, mannite monooleate. The CFA injection produces an area of localized edema and inflammation starting from few hours after injection, with a progressive reduction in the mechanical withdrawal threshold.

Each animal is allowed to develop the arthritis over a period of 8-9 days before testing.

Mechanical Allodynia

Mechanical allodynia thresholds is determined according to the method of Chaplan et al. (Chaplan S. R., Bach F. W., Pogrel J. W., Chung J. M., Yaksh T. L. J. Neurosci. Methods 53: 55-63 (1994)). Rats are placed in individual plastic boxes of 24×10×15 cm on a mesh metal floor and allowed to acclimate for about 30 minutes before testing. A series of calibrated von Frey hairs (Stoelting, Wood Dale, Ill., USA) with logarithmically incremental stiffness ranging from 2.83 to 5.88 expressed $Log_{10}$ of [10×force in (mg)] are applied to the paw with a modified up-down method (Dixon W. J. Am. Stat. Assoc. 60: 967-978 (1965)). In the absence of a paw withdrawal response to the initially selected hair, a thicker hair corresponding to a stronger stimulus is presented until a sharp withdrawal is recorded. The procedure is repeated twice. Each hair is presented perpendicularly against the paw, with sufficient force to cause slight bending, and held 2-3 s. The stimulation of the same intensity is applied five/six times to the hind paw at intervals of few seconds. The mechanical threshold is expressed as $Log_{10}$ of [10×force in (mg)] indicating the force of the von Frey hair to which the animal react (paw withdrawn, licking or shaking).

The mechanical allodynia thresholds are measured before (pre-drug) and at 30, 60, 90, 120, 240 and 360 minutes after the treatment. A 24 h threshold is also measured.

The compounds of the invention are administered in a range of doses of 0.1-100 mg/kg.

Example 12

Bennett Model of Neuropathic Pain in Rats

Effects on neuropathic pain are tested in the chronic constriction injury model in the rat (Bennett, G. J. and Xie, Y. K., "A peripheral mononeuropathy in rat that produces disorders of pain sensation like those seen in man". Pain, 33, 87-107 (1988)). Under pentobarbital anesthesia (Nembutal, 50 mg/kg, i.p.), unilateral multiple ligations are performed on male Sprague-Dawley rats (140-160 g) at the right common sciatic nerve. The sciatic nerve is exposed by blunt dissection at the level of mid-thigh and four loose ligatures (5-0 chromic catgut) are placed around the nerve taking care not to interrupt the epineural circulation. After operation, animals are allowed to recover for one week. Animals develop a cold allodynia which is stable for at least five weeks. Cold allodynia is tested on a metal plate cooled by a water bath to a constant temperature of 4° C. The animals, randomly assigned to groups of 10 for each test dose and vehicle, are observed for periods of 2 minutes before and after application of test compound and the number of brisk withdrawal reactions is counted. Several time points after application are tested. Percent maximal possible effect (% MPE) and standard error of the mean (SEM) of each time point is determined with the pre-test value used as 100% MPE. The area under the data (AUD) is calculated for the observation period and expressed as percent inhibition of vehicle control. Significance is calculated by paired t-test on the percent AUD values.

Example 13

Maximal Electroshock Test (MES) in Mice

The maximal electroshock test (MES) is used commonly in the screening of anti-epileptic drugs in rodent models.

Animals and Apparatus: Male CD1 mice weighing 25 g are used. The procedure described by White et al. (White H. S., Woodhead J. H., Franklin M. R., Swinyard E. A., and Wolf H. H. Antiepileptic Drugs 4th ed: 99-110 (1995), Raven Press, Ltd., New York) is followed. An Ugo Basile electroconvulsive generator Model ECT UNIT 7801 (Ugo Basile, Italy) is used to deliver an electrical stimulus sufficient to produce a hindlimb tonic extensor response in at least 97% of control animals. The stimulus is delivered intra-aurally through clip electrodes in mice (0.7 s of a 40 mA shock, with a pulse train of 80 Hz having a pulse duration of 0.4 ms). The acute effect of compounds administered intraperitoneally or orally 15-60 minutes before MES induction are examined and compared with a vehicle control group. Ten mice are studied per group. Complete suppression of the hindlimb tonic extensor component of seizures is taken as evidence of anticonvulsant activity.

The compounds of the invention are administered intravenously (iv), orally (os) or intraperitoneally (ip) at the doses of 0.1-100 mg/kg.

The results, obtained with a compound representative of the entire chemical class of the invention, administered iv and/or po, 15 minutes before testing, and reported in Table 4, demonstrate that these compounds are active as anticonvulsant drugs.

TABLE 4

| COMPOUND | 50% Protection |
|---|---|
| 2-[2,2-Difluoro-2-(3-butoxyphenyl)-ethylamino]-N,N-dimethyl-acetamide, hydrochloride (Example 1-1) | (9.8 mg/kg, po) |
| 2-[2-Fluoro-2-(3-butoxyphenyl)-ethylamino]-N,N-dimethyl-acetamide, hydrochloride (Example 4-1) | (4.0 mg/kg, iv) |

Example 14

Amphetamine and Chlordiazepoxide-Induced Hyperlocomotion in Mice

In this model, mice are treated with a mixture of d-amphetamine plus an anxiolytic dose of the benzodiazepine, chlordiazepoxide (Rushton R., Steinberg H. "Combined effects of chlordiazepoxide and d-amphetamine on activity of rats in an unfamiliar environment". Nature 211:1312-3 (1966); Arban R., Maraia G., Brackenborough K., Winyard L., Wilson A., Gerrard P., Large C. "Evaluation of the effects of lamotrigine, valproate and carbamazepine in a rodent model of mania". Behavioural Brain Research, 158: 123-132 (2005)). The model has been claimed to mimic some aspects of mania in bipolar disorder. Importantly, the hyperactivity induced by the mixture of d-amphetamine and chlordiazepoxide could be prevented by prior administration of the established mood stabilizer, lithium, as well as other mood stabilizers drugs (e.g. magnesium valproate and carbamazepine). Therefore, this model has face and predictive validity as a model of bipolar disorder and represents a valuable tool to determine, if a test compound could be a potential mood stabilizer drug candidate.

Amphetamine (AMP) (2.5 mg/kg) plus chlordiazepoxide hydrochloride (CDZ) (3 mg/kg/ip) are administered to male Albino Swiss mice (25-32 g) in a volume of 10 ml/kg. The locomotor activity is recorded using Opto-M3 System (Columbus Instruments, OH—USA) which is multi-channel activity monitor. Opto-M3 system has 10 infrared emitters and respective amount of receivers (0.5" beam spacing), attached to the PC computer and calculating both ambulatory activity and total counts. Thus the system differentiates forward locomotion (ambulation) from stereotyped like movement (total counts). Mice are pretreated with the test compound (5 mg/kg) and 10 min later, with AMP (2.5 mg/kg) or AMP jointly with CDZ (3 mg/kg). After successive 30 min. the mice are treated again with the same dose of the test compound and are placed individually in the motor activity cages. The locomotor activity (ambulation and total activity count) is evaluated for 30 min. Each group consists of 8-10 mice.

Statistical analysis: the data are evaluated by an analysis of variance (ANOVA), followed, when appropriate, by individual comparison with the control using Dunnett's test. Amphetamine-chlordiazepoxide administration induces a significant increase in locomotor activity.

Example 15

Model of Cognitive Impairment in Schizophrenia

Cognitive impairment is often associated with schizophrenia and it has come to be recognized as a core element of the disorder, bearing on patient's recovery and re-integration into society.

Particular interest has recently attracted a pharmacological model of cognitive dysfunctions in schizophrenia, which is based on the effects of glutamate NMDA receptor antagonists such as phencyclidine (PCP) and ketamine (Javitt D C, Zukin S R. Am. J. Psychiatry. 148:1301-1308. (1991)) which impair attention and increase "impulsivity" and "compulsive" preservation in mice performing a complex task (Greco B, Invernizzi R W, Carli M. Psychopharmacology (Berl) 179(1):68-76 (2005)).

Materials and Methods

Animals: Male DBA/2N mice (Charles River, Italy) are used. The mice weigh 25-30 g at the start of the experiments, and are housed under temperature-controlled conditions (21° C.) with a 12 hours light 12 hours dark cycle (light on 7:00 am-7:00 pm). Food (Rieper, Italy) is available ad libitum. The animals have two hours of access to water at the end of each day's testing.

The five-choice serial reaction time task apparatus: The test apparatus consists of four 21.6×17.8×12.7 cm chambers (Med Associates Inc. GA—USA), as previously described (Greco B, Invernizzi R W, Carli M. Psychopharmacology (Berl) 179(1):68-76 (2005)). Stimuli and recording of responses, are managed by a SmartCtrl™ Package 8 In/16 Out (Med Associates Inc. GA—USA) with additional interfacing by MED-PC for Windows (Med Associates Inc. GA—USA). The running program for the 5-Choice Serial Reaction Time (5-CSRT) task is custom-written.

Behavioural procedures: habituation to liquid reinforcer and nose poking in the holes. Mice are handled for one week and their body weight recorded. They are then water-deprived by allowing them 2-hours access to water in the early evening until their body weight has stabilised (8 days). Then, over the next two days the mice are habituated in their home cages to the reinforcer (10% sucrose solution) used afterwards in the operant procedures. On the following two days mice are habituated to the operant boxes. During this stage, 10% sucrose solution is available in a small bowl placed below the receptacle hole of the box. First, mice have to learn that every 5 seconds the liquid reward is available in a small cup in the receptacle hole. During this period head entries are recorded. During the next period, mice are trained to poke their noses into the illuminated holes. Immediately after a poke in the water receptacle a LED at the rear of one of the holes is turned on. A nose-poke in the lighted hole extinguishes the light stimulus and the liquid dipper provides a 0.01 mL liquid reward in the receptacle hole. Any response in one of the other four holes have no consequence and is not recorded. The light stimulus is presented in all five holes in random order. A mouse is switched to the 5-CSRT task after it has completed at least 50 rewarded nose-poke trials in one 30-min session.

The five-choice serial reaction time task. The start of the session is signalled by illumination of the house-light and the delivery of a 0.01 mL liquid reward. Nose poking in the receptacle hole begins the first trial. After a fixed delay (the inter-trial interval, ITI), the LED at the rear of one of the holes comes on for a short period. The LED stimulus is presented the same number of times in each hole during a complete session, with the order of presentation randomised by the computer. While the light is on, and for a short period afterwards (the limited hold), responses in the hole that is illuminated (correct response) result in the liquid reward. Responses in the holes that have not been illuminated (incorrect responses) or failure to respond within the limited hold (omissions) cause the house-lights to be turned off for a short period (time out). Responses in the holes while the house-light is off restart the time out. After the delivery of the liquid reward, or at the end of time out, the mouse starts the next trial by poking its nose into the receptacle hole. Responses made in the holes after a correct response (preservative responses), or after the end of time out before nose-poking into the receptacle hole, result in a period of time out. Responses in the holes during the ITI (anticipatory responses) also result in a period of time out. After anticipatory responses a nose-poke into the receptacle hole restart the current trial. Each daily session consists of 100 trials or 30 min of testing, whichever is completed sooner, after which all lights are turned off and further responses have no effect. In the first session of the test schedule, the stimulus and limited hold each last 1 minute and, depending on individual performance, they are progressively reduced to 1 second. The stimulus duration is reduced in the following sequence: 60, 30, 10, 5, 2.5, 2, 1.5 and 1 second (baseline). The ITI and time out both lasts 2 seconds during the first session and the ITI is raised to 5 seconds in subsequent sessions; time out is not changed. Throughout the whole period of training and experiments each mouse has one session per day on a 5-CSRT task.

Drugs and Treatment Schedules. The test compound is dissolved in water and is administered intraperitoneally (IP) at the dose of 10 mg/kg. Five minutes after the treatment mice are injected with vehicle (saline) or PCP (1.5 mg/kg) and 10 minutes later they start the test session. In each experiment the various combination of the test compound with vehicle or PCP are administered according to a Latin-square design. At least 48 hours are left between the drug testing days. During these intervening days the mice are tested on the 5-CSRT task to re-establish baseline performance and to check for any residual effects of drugs.

Statistical Analysis: The main dependent variables selected for analysis are: (a) the percentage of correct responses (total correct responses/total correct+total incorrect responses×100); (b) percentage of omissions (total omissions/total correct responses+total incorrect responses+total omissions×100); (c) the number of anticipatory responses in the holes during the ITI; (d) the number of preservative responses in the holes after a correct response. Correct responses and omissions, as percentages, are transformed according to the formula 2 arcsin (SQRT (%x/100)), to normalize the distributions in accordance with the ANOVA model.

The effects of the test compound (n=12) on PCP induced deficits in the 5-CSRT task are analysed independently by a within subjects 2×2 ANOVA with factors Drug (test compound) and PCP. Subsequently the treatment group means are compared using a post-hoc Tukey-Kramer test. Statistical software (SAS Institute Inc., NC—USA) is run on Micro VAX 3500 computer (Digital, MA—USA).

Example 16

Cocaine-Induced Behavioural Sensitization Test

Drug addiction is a pathological behaviour characterized by compulsive drug seeking and intake. One animal model of these behavioral changes is the long-lasting increase in locomotor activity induced by repeated administration of psychostimulant drugs in rodents (Robinson T. E. and Berridge K. C. Brain Res. Brain Res. Rev. 18, 247-91 (1993)) known as drug-induced behavioural sensitization. The effect of test compounds are evaluated in a model of cocaine-induced behavioral sensitization in rat.

Locomotor activity apparatus: Male Wistar rats weighing 200-250 g upon arrival are used. Locomotor activity is measured in sixteen identical metal wire hanging cages each measuring 36 cm (L)×25 cm (W)×20 cm (H). Each cage contains two sets of infrared emitter-detector photocells positioned along the long axis 1 cm above the grid floor and 8 cm from the front and back of the cage. Background noise is provided by a white noise generator. Movement within the cages produces photocell interruptions, which are automatically recorded by an IBM-compatible computer.

Sensitization procedure and treatment: Animals are habituated to the locomotor activity chambers for 2-3 consecutive days before the experiment. Rats receive 5 daily i.p. injections of cocaine (15 mg/kg) or saline and either the test compound (0.1-100 mg/kg) or its vehicle and locomotor activity is recorded for 3 h. Ten days after the last injection of cocaine or saline (day 15), the animals are challenged with 15 mg/kg of cocaine in absence of the test compound and locomotor activity is again monitored for 3 hours.

By the fifth day of treatment with cocaine, animals pretreated i.p. with vehicle show an increased locomotor response (20% higher then the first day, $p<0.05$). Ten days after the last injection of cocaine or saline, the animals are challenged with 15 mg/kg of cocaine in absence of the test compound and locomotor activity is again monitored for 3 h. The rats previously treated with cocaine and that have not received the test compound are expected to show an increased locomotor activity response to cocaine (30% higher then first day, $p<0.05$). If the rats that have been pretreated with the test compound during the 5 day-cocaine treatment do not show an increase in locomotor activity the test compound is considered to have an effect in preventing psychostimulant drugs addiction. (Koob G. F., Sanna P. P., Bloom F. E. Neuron 21: 467-476 (1998); Robinson T. E., Berridge K. C. Brain Res. Brain Res. Rev. 18: 247-291 (1993))

Statistical analysis: Data (total number of beam breaks in 3 hours) are analyzed using a two way ANOVA with repeated measures on one factor including the four experimental groups (i.e., saline/vehicle, saline/test compound, cocaine/vehicle and cocaine/test compound) and two time points (day 1 and day 5) followed by a simple effects analysis. A second two way ANOVA with repeated measures on one factor is used to compare day 1 and the challenge day followed by a Newman-Keuls post hoc test.

Example 17

Acute Bladder Irritation by Acetic Acid in Rats

Experiments are performed using adult anesthetized female Sprague Dawley rats (170-200 g). A catheter (PE-50) is inserted via a midline abdominal incision into the bladder through the bladder dome, and then intravescical pressure is measured to monitor bladder activity during continuous infusion of 0.15% of acetic acid. Continuous intravesical infusion of acetic acid irritates the bladder and reduces the intercontraction intervals (ICI) in anesthetized rats. ICIs, maximal contraction pressure, and pressure thresholds inducing reflex bladder contraction are measured before and after intravesical infusion of acetic acid in rats treated with compounds of the invention.

Example 18

Intermediate Bladder Irritation by Cyclophosphamide (CYP) in Rats

Experiments are performed using both adult awake and anesthetized female Sprague Dawley rats (170-200 g). Chemical cystitis is induced by CYP, which is metabolized to acrolein, an irritant eliminated in the urine. CYP (150 mg/kg/i.p.) is administered one day before the experiment. Pre-treatment with CYP causes bladder irritation and very frequent voidings with an ICI of about 150-200 seconds between voids.

Active compounds increase the ICI in both awake and anesthetized rats used in this experimental model.

Example 19

Migraine Test in Rats

Animals and Surgery: Male Wistar rats (250-350 g) are anesthetized with sodium pentobarbital (50 mg/kg i.p.) dissolved in saline.

The trachea and left femoral artery are cannulated for artificial ventilation (55 strokes/minute) and for measurement of mean blood pressure (MBP) respectively. The femoral vein is cannulated for the intravenous administration of test agents.

Body temperature is maintained at 37-38° C. by automatic control of a heating pad. Animals are placed in a stereotaxic frame and a longitudinal incision is made in the scalp. A burr hole is drilled in the skull and a stainless steel bipolar electrode Plastics One MS 306 (Plastics One Inc. VA—USA) is lowered into left ophthalmic branch of the trigeminal ganglion (3.8 mm dorsal to bregma, 2.5 mm lateral from the midline and 9.5 mm below the dural surface) and secured with dental cement. Correct placement of the electrode is confirmed by a brief electrical stimulation, which cause movement of the jaw due to activation of the trigeminal fiber. Following removal of the brain, the correct position of the electrode into the fiber, is visually checked at the end of each experiment.

A second hole is drilled ipsilateral of the electrode (1.5 mm rostral to bregma, and 1.5 mm lateral from the sagittal suture) and a needle probe (tip diameter 0.8 mm) of a laser doppler flowmeter is fixed pointing with its tip onto a branch of the middle cerebral artery (MCA) and Cerebral Blood Flow (CBF) change recorded on-line by the PeriFlux 4001 Laser Doppler system (Perimed, Italy).

Artefacts of the laser Doppler reading during electrical stimulation of the trigeminal ganglion due to muscular movements are prevented by a bolus of iv injection of the neuromuscular blocker pancuronium bromide (0.6 mg/kg iv).

Anesthesia and neuromuscular blockade are maintained all over the experiment with an infusion of sodium pentobarbital and pancuronium (12.5 mg/kg/h+2.4 mg/kg/h, respectively).

Experimental Protocol: At the end of the surgery, a pause of thirty minutes is taken in order to stabilize the measured parameters.

Rest CBF is increased by electrical stimulation with rectangular pulse of 0.5 ms length, 1-10 Hz, 0.5-1 mA for periods of 30 s. After two averaged pre-drug stimulations, vehicle or drugs are administered.

Active compounds reduce the increase in blood flow induced by trigeminal stimulation.

The invention claimed is:

1. A compound of general formula I

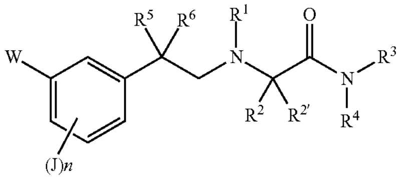

I wherein:

W is a group A—[$(CH_2)_m$—O]— wherein: m is 1, or 2;
A is ($C_1$-$C_4$)alkyl optionally substituted with one to three fluorine atoms; or phenyl;

J is hydrogen;

n is 1

$R^1$ is hydrogen; ($C_1$-$C_4$)alkyl optionally substituted with a ($C_1$-$C_4$)alkoxy group;

$R^2$ is hydrogen; or methyl;

$R^{2'}$ is hydrogen;($C_1$-$C_4$)alkyl optionally substituted with a methoxy group;

$R^3$ is hydrogen; or ($C_1$-$C_4$)alkyl;

$R^4$ is hydrogen; or ($C_1$-$C_4$)alkyl; $R^3$ and $R^4$, taken together with the adjacent nitrogen atom, form an azetidinyl, pyrrolidinyl, morpholinyl, piperidinyl or piperazinyl ring, the piperidinyl ring being optionally substituted on the other N-atom with a methyl group;

$R^5$ is hydrogen or fluoro; and $R^6$ is fluoro;

if the case, either as single optical isomer in the isolated form or as a mixture thereof in any proportion and its pharmaceutically acceptable salt.

2. A compound of claim 1, selected from:

2-[2,2-Difluoro-2-(3-butoxyphenyl)-ethylamino]-N,N-dimethyl-acetamide;

2-[2,2-Difluoro-2-(3-pentyloxyphenyl)-ethylamino]-N, N-dimethyl-acetamide

2-[2,2-Difluoro-2-(3-butoxyphenyl)-ethylamino]-N,N-dipropyl-acetamide

2-[2,2-Difluoro-2-(3-butoxyphenyl)-ethylamino]-N,N-dibutyl-acetamide;

2-[2,2-Difluoro-2-(3-hexyloxyphenyl)-ethylamino]-N,N-dimethyl-acetamide;

2-{2,2-Difluoro-2-[3-(4,4,4-trifluorobutoxy)-phenyl]-ethylamino}-N,N-dimethyl-acetamide;

2-[2,2-Difluoro-2-(3-pentyloxyphenyl)-ethylamino]-N, N-dipropyl-acetamide;

2-[2,2-Difluoro-2-(3-benzyloxyphenyl)-ethylamino]-N, N-dimethyl-acetamide;

2-[2,2-Difluoro-2-(3-butoxyphenyl)-ethylamino]-1-(pyrrolidin-1-yl)-ethanone;

2-{2,2-Difluoro-2-[3-(4,4,4-trifluorobutoxy)-phenyl]-ethylamino}-1-(pyrrolidin-1-yl)-ethanone;

2-[2,2-Difluoro-2-(3-benzyloxyphenyl)-ethylamino]-1-(morpholin-4-yl)-ethanone;

2-{2,2-Difluoro-2-[3-(4,4,4-trifluorobutoxy)-phenyl]-ethylamino}-1-(morpholin-4-yl)-ethanone;

2-[2,2-Difluoro-2-(3-benzyloxyphenyl)-ethylamino]-1-(pyrrolidin-1-yl)-ethanone;

2-[2,2-Difluoro-2-(3-butoxyphenyl)-ethylamino]-1-(4-methylpiperazin-1-yl)-ethanone;

2-{2,2-Difluoro-2-[3-(4,4,4-trifluorobutoxy)-phenyl]-ethylamino}-1-(4-methylpiperazin-1-yl)-ethanone;

2-[2,2-Difluoro-2-(3-butoxyphenyl)-ethylamino]-1(piperidin-1-yl)-acetamide;

2-{2,2-Difluoro-2-[3-(4,4,4-trifluorobutoxy)-phenyl]-ethylamino}-1-(piperidin-1-yl)-ethanone;

2-[2,2-Difluoro-2-(3-butoxyphenyl)-ethylamino]-N,N-diethyl-acetamide;

2-[2,2-Difluoro-2-(3-butoxyphenyl)-ethylamino]-N,N-diisopropyl-acetamide;

2-[2,2-Difluoro-2-(3-benzyloxyphenyl)-ethylamino]-1-(piperidin-1-yl)-ethanone;

2-[2,2-Difluoro-2-(3-butoxyphenyl)-ethylamino]-1-(azetidin-1-yl)-ethanone;

2-[2,2-Difluoro-2-(3-butoxyphenyl)-ethylamino]-N,N-dimethyl-propanamide;

2-[2,2-Difluoro-2-(3-butoxyphenyl)-ethylamino]-3-methoxy-N,N-dimethyl-propanamide;

2-[2,2-Difluoro-2-(3-butoxyphenyl)-ethylamino]-2-N,N-trimethyl-propanamide;

2-{[2,2-Difluoro-2-(3-butoxyphenyl)-ethyl]-methyl-amino}-N,N-dimethyl-acetamide;

2-{[2,2-Difluoro-2-(3-butoxyphenyl)-ethyl]-(3-methoxy-propyl)-amino}-N,N-dimethyl-acetmide;

2-{[2,2-Difluoro-2-(3-butoxyphenyl)-ethyl]-(2-methoxy-ethyl)-amino}-N,N-dimethyl-acetamide;

2-[2-Fluoro-2-(3-butoxyphenyl)-ethylamino]-N,N-dimethyl-acetamide;

if the case, either as single optical isomer in the isolated form or a mixture thereof in any proportion, and its pharmaceutically acceptable salt.

3. A compound of claim 2 which is selected from 2-[2,2-difluoro-2-(3-butoxyphenyl)-ethylamino]-N,N-dimethyl-acetamide, 2-[2-fluoro-2-(3-butoxyphenyl)-etylamino]-N,N-dimethyl-acetamide, its single optical isomer in the isolated form or a mixture thereof in any proportion, and the pharmaceutically acceptable salts thereof.

4. A compound of claim 3 which is 2-[2,2-difluoro-2-(3-butoxyphenyl)-ethylamino]-N,N-dimethyl-acetamide or a pharmaceutically acceptable salt thereof.

5. A compound as in claim 1 wherein the pharmaceutically acceptable salt is the hydrochloride.

6. A pharmaceutical composition containing a compound of claim 1 as active ingredient together with a pharmaceutically acceptable excipient.

7. A pharmaceutical composition of claim 6 containing a further therapeutical agent.

8. A method for the treatment of a disorder caused by dysfunctions of voltage gated sodium and/or calcium channels in a patient, said method comprising the administration to a patient in need thereof an effective amount of a sodium and/or calcium channel modulating amount of a compound of claim 1.

9. A method as in claim 8 wherein the disorder caused by dysfunctions of voltage gated sodium and/or calcium channels is selected from neuropathic pain, chronic pain, acute pain, headaches, neurological conditions, neurogenerative disorders, cognitive disorders, psychiatric disorders, vertigo, tinnitus, muscle spasm, cardiovascular diseases, endocrine disorders involving excessive or hypersecretory or otherwise inappropriate cellular secretion of an endogenous substance, liver diseases, inflammatory processes affecting all body systems, disorders of the gastrointestinal (GI) tract, disorders of the genito-urinary tract, ophthalmic diseases and eating disorders.

10. A method as in claim 9 wherein the disorder is a neuropathic pain, chronic pain and/or acute pain.

11. A method as in claim 9 wherein the disorder is headache.

12. A method as in claim 9 wherein the disorder is a cognitive and/or psychiatric disorder.

13. A method as in claim 9 wherein the disorder is a neurological condition.

14. A method as in claim 9 wherein the disorder is an inflammatory process affecting all body systems, a disorder of the gastrointestinal tract, a disorder of the genito-urinary tract, an ophthalmic disease, a liver disease, a cardiovascular, and/or neurodegenerative disorder caused by dysfunctions of voltage gated sodium and/or calcium channels.

15. A method as in claim 9 wherein the patient is a poor metabolizer having very little or no CYP2D6 function, or is assuming drug(s) that is(are) CYP2D6 inhibitor(s).

16. A method as in claim 13, wherein the neurological condition is epilepsy.

17. A method as in claim 9, wherein the patient is administered a further therapeutical agent.

18. A pharmaceutical composition of claim 6, wherein the compound is in the form of a pharmaceutically acceptable salt.

19. A pharmaceutical composition of claim 18, wherein the pharmaceutically acceptable salt is the hydrochloride.

20. A method as in claim 8, wherein the compound is in the form of a pharmaceutically acceptable salt.

21. A method as in claim 20 wherein the pharmaceutically acceptable salt is the hydrochloride.

22. A compound of claim 5 which is the hydrochloride salt of 2-[2,2-difluoro-2-(3-butoxyphenyl)-etylamino]-N,N-dimethyl-acetamide.

23. A pharmaceutically composition of claim 19, wherein the compound is the hydrochloride salt of 2-[2,2-difluoro-2-(3-butoxyphenyl)-ethylamino]-N,N-dimethyl-acetamide.

24. A method as in claim 21, wherein the pharmaceutically acceptable salt is the hydrochloride salt of 2-[,2,2-difluoro-2-(3-butoxyphenyl)-ethylamino]-N,N-dimethyl-acetamide.

* * * * *